US009297021B2

(12) United States Patent
Dickstein et al.

(10) Patent No.: US 9,297,021 B2
(45) Date of Patent: Mar. 29, 2016

(54) ***MTNIP* REGULATED PLANTS WITH SIGNIFICANTLY INCREASED SIZE AND BIOMASS**

(71) Applicant: University of North Texas, Denton, TX (US)

(72) Inventors: Rebecca Dickstein, Denton, TX (US); Mohammad Salehin, Denton, TX (US); Rammyani Bagchi, Denton, TX (US)

(73) Assignee: UNIVERSITY OF NORTH TEXAS, Denton, TX (US)

( * ) Notice: Subject to any disclaimer, the term of this patent is extended or adjusted under 35 U.S.C. 154(b) by 594 days.

(21) Appl. No.: 13/667,257

(22) Filed: Nov. 2, 2012

(65) Prior Publication Data

US 2013/0145498 A1 Jun. 6, 2013

Related U.S. Application Data

(60) Provisional application No. 61/554,836, filed on Nov. 2, 2011.

(51) Int. Cl.
*C12N 15/82* (2006.01)
*C07K 14/415* (2006.01)

(52) U.S. Cl.
CPC .......... *C12N 15/8262* (2013.01); *C07K 14/415* (2013.01); *C12N 15/827* (2013.01); *C12N 15/8261* (2013.01)

(58) Field of Classification Search
None
See application file for complete search history.

(56) References Cited

U.S. PATENT DOCUMENTS

| | | | | |
|---|---|---|---|---|
| 5,498,830 | A | 3/1996 | Barry et al. | |
| 6,426,447 | B1 | 7/2002 | Knauf et al. | |
| 6,855,877 | B2 | 2/2005 | Garing | |
| 6,864,409 | B2 | 3/2005 | Cummings | |
| 7,294,760 | B2 | 11/2007 | Ruezinsky | |
| 7,335,812 | B2 | 2/2008 | Fernandes et al. | |
| 7,847,153 | B2 | 12/2010 | Ruezinsky | |
| 7,994,402 | B2 | 8/2011 | Fernandes et al. | |
| 8,049,071 | B2 | 11/2011 | Gao et al. | |
| 8,062,840 | B2 | 11/2011 | Anderson et al. | |
| 2002/0134012 | A1 | 9/2002 | Ding et al. | |
| 2003/0236208 | A1* | 12/2003 | Kmiec et al. | 514/44 |
| 2004/0023801 | A1 | 2/2004 | Asrar et al. | |
| 2004/0023802 | A1 | 2/2004 | Asrar et al. | |
| 2005/0197251 | A1 | 9/2005 | Ding et al. | |
| 2011/0252510 | A1 | 10/2011 | Aasen et al. | |

FOREIGN PATENT DOCUMENTS

| | | |
|---|---|---|
| WO | 2008/142036 | 11/2008 |

OTHER PUBLICATIONS

Sun et al. Nature Mar. 2014, vol. 000 1-5.*
Yendrek et al. (The Plant Journal (2010) 62, 100-112).*
Guo et al (2004, Proc. Natl. Acad. Sci. USA 101: 9205-9210).*
Li et al. (The Plant Cell, vol. 22: 1633-1646, May 2010).*
Bell et al. (Plant Molecular Biology 23:445-451, 1993).*
European Patent Office; Response to First Written Opinion; PCT Application No. PCT/US12/063220; Aug. 30, 2013.
European Patent Office; Second Written Opinion; PCT Application No. PCT/US12/063220; Oct. 11, 2013.
European Patent Office; Response to Second Written Opinion; PCT Application No. PCT/US12/063220; Nov. 21, 2013.
European Patent Office; International Preliminary Report on Patentability; PCT Application No. PCT/US12/063220; Jan. 24, 2014.
Abogadallah GM, Nada RM, Malinowski R, Quick P (2011) Overexpression of HARDY, an AP2/ERF gene from Arabidopsis, improves drought and salt tolerance by reducing transpiration and sodium uptake in transgenic Trifolium alexandrinum L. Planta 233: 1265-1276.
Auriac M-C, Timmers ACJ (2007) Nodulation studies in the model legume Medicago truncatula: Advantages of using the constitutive EF1 a promoter and limitations in detecting fluorescent reporter proteins in nodule tissues. Molecular Plant Microbe Interactions 20: 1040-1047.
Bhatnagar-Mathur P, Vadez V, Sharma KK (2008) Transgenic approaches for abiotic stress tolerance in plants: retrospect and prospects. Plant Cell Reports 27: 411-424.
Bright L, Liang Y, Mitchell DM, Harris JM (2005) LATD, a gene required for both nodule and root development. Molecular Plant-Microbe Interactions 18: 521-532 Gonzalez N, Beemster GT, Inze D (2009) David and Goliath: what can the tiny weed Arabidopsis teach us to improve biomass production in crops? Current Opinion in Plant Biology 12: 157-164.
Flavell R (2005) Model plants, with special emphasis on Arabidopsis thaliana, and crop improvement. In R Tuberosa, RL Phillips, M Gale, eds, Proceedings of the International Congress In the Wake of the Double Helix: From the Green Revolution to the Gene Revolution, May 27-31, 2003, Bologna, Italy. Avenue Media, Bologna, Italy, pp. 365-378.
Gao S, Zhang H, Tian Y, Li F, Zhang Z, Lu X, Chen X, Huang R (2008 ) Expression of TERF1 in rice regulates expression of stress-responsive genes and enhances tolerance to drought and high-salinity. Plant Cell Rep. 27: 1787-1795.
Gonzalez N, De Bodt S, Sulpice R, Jikumaru Y, Chae E, Dhondt S, Van Daele T, De Milde L, Weigel D, Kamiya Y, Stitt M, Beemster GTS, Inze D (2010) Increased leaf size: Different means to an end. Plant Physiology 153: 1261-1279.
Ho C-H, Lin S-H, Hu H-C, Tsay Y-F (2009) CHL1 functions as a nitrate sensor in plants. Cell 138: 1184-1194.
Huang N-C, Chiang C-S, Crawford NM, Tsay Y-F (1996) CHL1 encodes a component of the low-affinity nitrate uptake system in Arabidopsis and shows cell type-specific expression in roots. Plant Cell 8: 2183-2191.
Hussain SS, Kayani MA, Amjad M (2011) Transcription factors as tools to engineer enhanced drought stress tolerance in plants. Biotechnology Progress 27: 297-306.
Jeong J, Suh S, Guan C, Tsay Y-F, Moran N, Jae Oh C, An C-S, Demchenko KN, Pawlowski K, Lee Y (2004) A nodule-specific dicarboxylate transporter from alder is a member of the peptide transporter family. Plant Physiology 134: 969-978.

(Continued)

*Primary Examiner* — Anne Kubelik
*Assistant Examiner* — Charles Logsdon
(74) *Attorney, Agent, or Firm* — Jackson Walker LLP

(57) ABSTRACT

A composition and method for producing plants with increased biomass and growth characteristics, and plants which flower early relative to wild-type plants. The MtNIP gene is over-expressed in plants to increase biomass, growth, and early flowering. Other genes in the NRT1/PTR family may also be over-expressed to increase biomass, growth, and early flowering.

21 Claims, 20 Drawing Sheets

(56) References Cited

OTHER PUBLICATIONS

Jin T, Chang Q, Li W, Yin D, Li Z, Wang D, Liu B, Liu L (2010) Stress-inducible expression of GmDREB1 conferred salt tolerance in transgenic alfalfa. Plant Cell Tissue Organ Cult 100: 219-227.
Katayama H, Mori M, Kawamura Y, Tanaka T, Mori M, Hasegawa H (2009) Production and characterization of transgenic plants carrying a high-affinity nitrate transporter gene (OsNRT2.1) Breeding Science 59:237-243.
Krizek BA (2009) Making bigger plants: key regulators of final organ size. Current Opinion in Plant Biology 12: 17-22.
Krouk G, Lacombe B, Bielach A, Perrine-Walker F, Malinska K, Mounier E, Hoyerova K, Tillard P, Leon S, Ljung K, Zazimalova E, Benkova E, Nacry P, Gojon A (2010) Nitrate-Regulated Auxin Transport by NRT1.1 Defines a Mechanism for Nutrient Sensing in Plants. Developmental Cell 18: 927-937
Liu K-H, Huang C-Y, Tsay Y-F (1999) CHL1 is a dual affinity nitrate transporter of Arabidopsis involved in multiple phases of nitrate uptake. Plant Cell 11.
Manavalan LP, Guttikonda SK, Tran LS, Nguyen HT (2009) Physiological and molecular approaches to improve drought resistance in soybean. Plant and Cell Physiology 50: 1260-1276.
NSF (2002) Beyond the Whole Genome Sequence. In. National Science Foundation, Arlington, VA http://www.nsf.gov/pubs/2002/bio0202/model.htm.
Teillet A, Garcia J, de Billy F, Gherardi M, Huguet T, Barker DG, de Carvalho-Niebel F, Journet E-P (2008) api, a novel Medicago truncatula symbiotic mutant impaired in nodule primordium invasion. Molecular Plant Microbe Interactions 21: 535-546.
Tsay Y-F, Chiu C-C, Tsai C-B, Ho C-H, Hsu P-K (2007) Nitrate transporters and peptide transporters. FEBS Letters 581 2290-2300.
Tsay Y-F, Schroeder JI, Feldmann KA, Crawford NM (1993) The herbicide sensitivity gene CHL1 of Arabidopsis encodes a nitrate-inducible nitrate transporter. Cell 72: 705-713.
Valente MAS, Faria JAQA, Soares-Ramos JRL, Reis PAB, Pinheiro GL, Piovesan ND, Morais AT, Menezes CC, Cano MAO, Fietto LG, Loureiro ME, Aragão FJL, Fontes EPB (2009) The ER luminal binding protein (BiP) mediates an increase in drought tolerance in soybean and delays drought-induced leaf senescence in soybean and tobacco. Journal of Experimental Botany 60: 533-546.
Veereshlingam H, Haynes JG, Sherrier DJ, Penmetsa RV, Cook DR, Dickstein R (2004) nip, a symbiotic Medicago truncatula mutant that forms root nodules with aberrant infection threads and plant defense-like response. Plant Physiol. 136: 3692-3702.
Wang R, Liu D, Crawford NM (1998) The Arabidopsis CHL protein plays a major role in high-affinity nitrate uptake. Proc Natl Acad Sci U S A 95: 15134-15139.
Wang R, Xing X, Wang Y, Tran A, Crawford NM (2009) A genetic screen for nitrate regulatory mutants captures the nitrate transporter gene NRT1.1. Plant Physiology 151: 72-478.
Ware D, Stein L (2003) Comparison of genes among cereals. Current Opinion in Plant Biology 6: 121-127.
Yendrek CR, Lee Y-C, Morris V, Liang Y, Pislariu CI, Burkart G, Meckfessel MH, Salehin M, Kessler H, Wessler H, Lloyd M, Lutton H, Teillet A, Sherrier DJ, Journet E-P, Harris JM, Dickstein R (2010) A putative transporter is essential for integrating nutrient and hormone signaling with lateral root growth and nodule development in Medicago truncatula. The Plant Journal 62: 100-112.
Zhang H, Liu W, Wan L, Li F, Dai L, Li D, Zhang Z, Huang R (2010) Functional analyses of ethylene response factor JERF3 with the aim of improving tolerance to drought and osmotic stress in transgenic rice. Transgenic Res 19: 809-818.
Zhang JZ, Creelman RA, Zhu J-K (2004) Froml aboratory to field. Using information from Arabidopsis to engineer salt, cold, and drought tolerance in crops. Plant Physiology 135: 615-621.
Zhang Z, Huang R (2010) Enhanced tolerance to freezing in tobacco and tomato overexpressing transcription factor TERF2/LeERF2 is modulated by ethylene biosynthesis. Plant Molecular Biology 73: 241-249.
Zhang Z, Li F, Li D, Zhang H, Huang R (2010) Expression of ethylene response factor JERF1 in rice improves tolerance to drought. Planta 232: 765-774.
Almagro A, Lin Sh, Tsay Y-F (2008) Characterization of the Arabidopsis nitrate transporter NRT1.6 reveals a role of nitrate in early embryo development. Plant Cell: doi/10.1105/tpc.1107.056788.
Barbier-Brygoo H, De Angeli A, Filleur S, Frachisse J-M, Gambale F, Thomine S, Wege S (2011) Anion channels/transporters in plants: From molecular bases to regulatory networks. Annu. Rev. Plant Biol. 62: 25-51.
Bekki A, Trinchant J-C, Rigaud J (1987) Nitrogen fixation (C2H2 reduction) by Medicago nodules and bacteroids under sodium chloride stress. Physiol. Plant 71: 61-67.
Benedito VA, Li H, Dai X, Wandrey M, He J, Kaundal R, Torres-Jerez I, Gomez SK, Harrison MJ, Tang Y, Zhao PX, Udvardi MK (2010) Genomic inventory and transcriptional analysis of Medicago truncatula transporters. Plant Physiology 152: 1716-1730.
Boisson-Dernier A, Chabaud M, Garcia F, Becard G, Rosenberg C, Barker DG (2001) Agrobacterium rhizogenestransformed roots of Medicago truncatula for the study of nitrogen-fixing and endomycorrhizal symbiotic associations. Molecular Plant Microbe Interactions 14: 695-700.
Boivin C, Camut S, Malpica CA, Truchet G, Rosenberg C (1990) Rhizobium meliloti genes encoding catabolism of trigonelline are induced under symbiotic conditions. Plant Cell 2: 1157-1170.
Clough SJ, Bent AF (1998) Floral dip: a simplified method for Agrobacterium-mediated transformation of Arabidopsis thaliana. Plant Journal 16: 735-743.
Correa-Aragunde N, Graziano M, Lamattina L (2004) Nitric oxide plays a central role in determining lateral root development in tomato. Planta 218: 900-905.
Crawford NM (1995) Nitrate: nutrient and signal for plant growth. . Plant Cell 7: 859-868.
del Giudice J, Cam Y, Damiani I, Fung-Chat F, Meilhoc E, Bruand C, Brouquisse R, Puppo A, Boscari A (2011) Nitric oxide is required for an optimal establishment of the Medicago truncatula—Sinorhizobium meliloti symbiosis. New Phytologist 191: 405-417.
Doddema H, Hofstra JJ, Feenstra WJ (1978) Uptake of nitrate by mutants of Arabidopsis thaliana, disturbed in uptake or reduction of nitrate. Physiol. Plant 43: 343-350.
Ehrhardt DW, Atkinson EM, Long SR (1992) Depolarization of alfalfa root hair membrane potential by Rhizobium meliloti Nod factors. Science 256 998-1000.
Fan S-C, Lin C-S, Hsua P-K, Lin S-H, Tsay Y-F (2009) The Arabidopsis nitrate transporter NRT1.7, expressed in phloem, is responsible for source-to-sink remobilization of nitrate. The Plant Cell 21: 2750-2761.
Fei H, Vessey JK (2008) Stimulation of nodulation in Medicago truncatula by low concentrations of ammonium: quantitative reverse transcription PCR analysis of selected genes. Physiologia Plantarum 135: 317-330.
Gojon A, Krouk G, Perrine-Walker F, Laugier E (2011) Nitrate transceptor(s) in plants. Journal of Experimental Botany 62: 2299-2308.
Harris JM, Dickstein R (2010) Control of root architecture and nodulation by the LATD/NIP transporter. Plant Signaling & Behavior 5: 1386 - 1390.
Hofgen R, Willmitzer L (1988) Storage of competent cells for Agrobacterium transformation. Nucl. Acids Res. 16: 9877.
Horchani F, Prevot M, Boscari A, Evangelisti E, Meilhoc E, Bruand C, Raymond P, Boncompagni E, Aschi-Smiti S, Puppo A, Brouquisse R (2011) Both plant and bacterial nitrate reductases contribute to nitric oxide production in Medicago truncatula nitrogen-fixing nodules. Plant Physiology 155: 1023-1036.
Kanno Y, Hanada A, Chiba Y, Ichikawa T, Nakazawa M, Matsui M, Koshiba T, Kamiya Y, Seo M (2012) Identification of an abscisic acid transporter by functional screening using the receptor complex as a sensor. Proc Natl Acad Sci U S A 109: 9653-9658.
Kouchi H, Imaizumi-Anraku H, Hayashi M, Hakoyama T, Nakagawa T, Umehara Y, Suganuma N, Kawaguchi M (2010) How many peas in a pod? Legume genes responsible for mutualistic symbioses underground. Plant Cell Physiology 51: 1381-1397.

(56) References Cited

OTHER PUBLICATIONS

Krieg PA, Melton DA (1984) Functional messenger RNAs are produced by SP6 in vitro transcription of cloned cDNAs. Nucl. Acids Res. 12: 7057-7070.
Krouk G, Crawford NM, Coruzzi GM, Tsay YF (2010) Nitrate signaling: adaptation to fluctuating environments. Current Opinion in Plant Biology 13: 266-273.
Li J-Y, Fu Y-L, Pike SM, Bao J, Tian W, Zhang Y, Chen C-Z, Zhang Y, Li H-M, Huang J, Li L-G, Schroeder JI, Gassmann W, Gong J-M (2010) The Arabidopsis nitrate transporter NRT1.8 functions in nitrate removal from the xylem sap and mediates cadmium tolerance. Plant Cell 22: 1633-1646.
Liang Y, Harris JM (2005) Response of root branching to abscisic acid is correlated with nodule formation both in legumes and non-legumes. American Journal of Botany 92: 1675-1683.
Liang Y, Mitchell DM, Harris JM (2007) Abscisic acid rescues the root meristem defects of the Medicago truncatula latd mutant. Developmental Biology 304 297-307.
Lin S-H, Kuo H-F, Canivenc G, Lin C-S, Lepetit M, Hsu P-K, Tillard P, Lin H-L, Wang Y-Y, Tsai C-B, Gojon A, Tsay Y-F (2008) Mutation of the Arabidopsis NRT1.5 nitrate transporter causes defective root-to-shoot nitrate transport. . Plant Cell 20: 2514-2528.
Linkohr BI, Williamson LC, Fitter AH, Leyser HMO (2002) Nitrate and phosphate availability and distribution have different effects on root system architecture of Arabidopsis. Plant Journal 29: 751-760.
Lullien V, Barker DG, de Lajudie P, Huguet T (1987) Plant gene expression in effective and ineffective root nodules of alfalfa (*Medicago sativa*). Plant Molecular Biology 9: 469-478.
Meilhoc E, Boscari A, Bruand C, Puppo A, Brouquisse R (2011) Nitric oxide in legume-rhizobium symbiosis. Plant Science 181: 573-581.
Miller AJ, Fan X, Orsel M, Smith SJ, Wells DM (2007) Nitrate transport and signalling. Journal of Experimental Botany 58: 2297-2306.
Miranda M, Borisjuk L, Tewes A, Dietrich D, Rentsch D, Weber H, Wobus U (2003) Peptide and amino acid transporters are differentially regulated during seed development and germination in faba bean. Plant Physiology 132: 1950-1960.
Morere-Le Paven M-C, Viau L, Hamon A, Vandecasteele C, Pellizzaro A, Bourdin C, Laffont C, Lapied B, Lepetit M, Frugier F, Legros C, Limami AM (2011) Characterization of a dual-affinity nitrate transporter MtNRT1.3 in the model legume Medicago truncatula. Journal of Experimental Botany 62: 5595-5605.
Molter V, Den Herder G, Whitford R, Van de Velde W, Rombauts S, D'haeseleer K, Holsters M, Goormachtig S (2010) CLE peptides control Medicago truncatula nodulation locally and systemically. Plant Physiology 153: 222-237.
Munos S, Cazettes C, Fizames C, Gaymard F, Tillard P, Lepetit M, Lejay L, Gojon A (2004) Transcript profiling in the chl1-5 mutant of Arabidopsis reveals a role of the nitrate transporter NRT1.1 in the regulation of another nitrate transporter, NRT2.1. Plant Cell 16: 2433-2447.
Oldroyd GED, Downie JA (2008) Coordinating nodule morphogenesis with rhizobial infection in legumes. Annu. Rev. Plant Biol. 59 519-546.
Penmetsa RV, Cook DR (1997) A legume ethylene-insensitive mutant hyperinfected by Its rhizobial symbiont. Science 275: 527-530.
Pislariu CI, Dickstein R (2007) An IRE-like AGC Kinase Gene, MtIRE, has unique expression in the invasion zone of developing root nodules in Medicago truncatula. Plant Physiology 144: 682-694.
Quandt HJ, Puhler A, Broer I (1993) Transgenic root nodules of Vicia hirsuta: A fast and efficient system for the study of gene expression in indeterminate-type nodules. Molecular Plant-Microbe Interactions 6: 699-706.
Remans T, Nacry P, Pervent M, Filleur S, Diatloff E, Mounier E, Tillard P, Forde BG, Gojon A (2006) The Arabidopsis NRT1.1 transporter participates in the signaling pathway triggering root colonization of nitrate-rich patches. Proc Natl Acad Sci U S A 103: 19206-19211.
Sato S, Nakamura Y, Kaneko T, Asamizu E, Kato T, Nakao M, Sasamoto S, Watanabe A, Ono A, Kawashima K, Fujishiro T, Katoh M, Kohara M, Kishida Y, Minami C, Nakayama S, Nakazaki N, Shimizu Y, Shinpo S, Takahashi C, Wada T, Yamada M, Ohmido N, Hayashi M, Fukui K, Baba T, Nakamichi T, Mori H, Tabata S (2008) Genome structure of the legume, *Lotus japonicus*. DNA Research 15: 227-239.
Schmutz J, Cannon SB, Schlueter J, Ma J, Mitros T, Nelson W, Hyten DL, Song Q, Thelen JJ, Cheng J, Xu D, Hellsten U, May GD, Yu Y, Sakurai T, Umezawa T, Bhattacharyya MK, Sandhu D, Valliyodan B, Lindquist E, Peto M, Grant D, Shu S, Goodstein D, Barry K, Futrell-Griggs M, Abernathy B, Du J, Tian Z, Zhu L, Gill N, Joshi T, Libault M, Sethuraman A, Zhang X-C, Shinozaki K, Nguyen HT, Wing RA, Cregan P, Specht J, Grimwood J, Rokhsar D, Stacey G, Shoemaker RC, Jackson SA (2010) Genome sequence of the palaeopolyploid soybean. Nature 463: 178-183.
Segonzac C, Boyer J-C, Ipotesi E, Szponarski W, Tillard P, Touraine B, Sommerer N, Rossignol M, Gibrata R (2007) Nitrate efflux at the root plasma membrane: Identification of an Arabidopsis excretion transporter. Plant Cell 19: 3760-3777.
Srivastava AC, Ganesan S, Ismail IO, Ayre BG (2008) Functional characterization of the Arabidopsis AtSUC2 sucrose/H+ symporter by tissue-specific complementation reveals an essential role in phloem loading but not in long-distance transport. Plant Physiology 148: 200-211.
Udvardi MK, Day DA (1997) Metabolite transport across symbiotic membranes of legume nodules. Annual Review of Plant Physiology and Plant Molecular Biology 48: 493-523.
Walch-Liu P, Forde BG (2008) Nitrate signalling mediated by the NRT1.1 nitrate transporter antagonises L-glutamate-induced induced changes in root architecture. Plant Journal doi: 10.1111/j.1365-313X.2008.03443.x.
Walch-Liu P, Liu L-H, Remans T, Tester M, Forde BG (2006) Evidence that L-glutamate can act as an exogenous signal to modulate root growth and branching in Arabidopsis thaliana. Plant Cell Physiol. 47: 1045-1057.
Wang Y-Y, Tsay Y-F (2011) Arabidopsis nitrate transporter NRT1.9 is important in phloem nitrate transport. Plant Cell 23: 1945-1957.
Waterworth WM, Bray CM (2006) Enigma variations for peptides and their transporters in higher plants. Annals of Botany 98: 1-8.
White J, Prell J, James EK, Poole P (2007) Nutrient sharing between symbionts. Plant Physiology 144: 604-614.
Wilkinson JQ, Crawford NM (1991) Identification of the Arabidopsis CHL3 gene as the nitrate reductase structural gene NIA2. Plant Cell 3: 461-471.
Xu G, Fan X, Miller AJ (2012) Plant nitrogen assimilation and use efficiency. Annual Review Plant Biology 63: 5.1-5.30.
Yamashita T, Shimada S, Guo W, Sato K, Kohmura E, Hayakawa T, Takagi T, Tohyama M (1997) Cloning and functional expression of a brain peptide/histidine transporter. Journal of Biological Chemistry 272: 10205-10211.
Yokoyama T, Kodama N, Aoshima H, Izu H, Matsushita K, Yamada M (2001) Cloning of a cDNA for a constitutive NRT1 transporter from soybean and comparison of gene expression of soybean NRT1 transporters. Biochimica et Biophysica Acta 1518: 79-86.
Young ND, Debellé F, Oldroyd GED, Geurts R, Cannon SB, Udvardi MK, Benedito VA, Mayer KFX, Gouzy J, Schoof H, Van de Peer Y, Proost S, Cook DR, Meyers BC, Spannagl M, Cheung F, De Mita S, Krishnakumar V, Gundlach H, Zhou S, Mudge J, Bharti AK, Murray JD, Naoumkina MA, Rosen B, et al. (2011) The Medicago genome provides insight into the evolution of rhizobial symbioses. Nature 480: 520-524.
Zhang H, Jennings AJ, Forde BB (2000) Regulation of Arabidopsis root development by nitrate availability. Journal of Experimental Botany 51: 51-59.
Zhao X, Huang J, Yu H, Wang L, Xie W (2010) Genomic survey, characterization and expression profile analysis of the peptide transporter family in rice (*Oryza sativa* L.). BMC Plant Biology 10 92.
Zhou J-J, Theodoulou FL, Muldini I, Ingemarssoni B, Miller AJ (1998) Cloning and functional characterization of a Brassica napus transporter that is able to transport nitrate and histidine. Journal of Biological Chemistry 273: 12017-2023.

(56) References Cited

OTHER PUBLICATIONS

Zifarelli G, Pusch M (2010) CLC transport proteins in plants. FEBS Letters 584: 2122-2127.
European Patent Office; International Search Report and Written Opinion; PCT Application No. PCT/US2012/063220; Feb. 1, 2013.
Cui, MA, et al; Responses of rice plants of Wuyunjing 7 to nitrate as affected by Over-Expression of OsNRT1 . 2; Zhongguo Shuidao Kexue, vol. 25, No. 4, Jul. 2011, pp. 349-356, XP002690580.
Bagchi, R., et al; Functional Assessment of the Medicago Truncatula NIP/LATD Protein Demonstrates That It Is a High-Affinity Nitrate Transporter; Plant Physiology, vol. 160, No. 2, Oct. 1, 2012, pp. 906-916.
Rosenberg C, Boistard P, Denarie J, Casse-Delbart F (1981) Genes controlling early and late functions in symbiosis are located on a megaplasmid in Rhizobium meliloti. Molecular and General Genetics 184: 326-333.
Salazar C, Armenta JM, Cortés DF, Shulaev V (2012) Combination of an AccQ•Tag-Ultra Performance Liquid Chromatographic Method with Tandem Mass Spectrometry for the Analysis of Amino Acids. In MA Alterman, P Hunziker, eds, Amino Acid Analysis: Methods and Protocols, Methods in Molecular Biology, vol. 828. Humana Press, pp. 13-28.
Streeter J (1988) Inhibition of legume nodule formation and N2 fixation by nitrate. CRC Critical Reviews in Plant Science 7: 1-23.
European Patent Office; European Application No. 12 783 483.6; Office Action; Jul. 7, 2015.

* cited by examiner

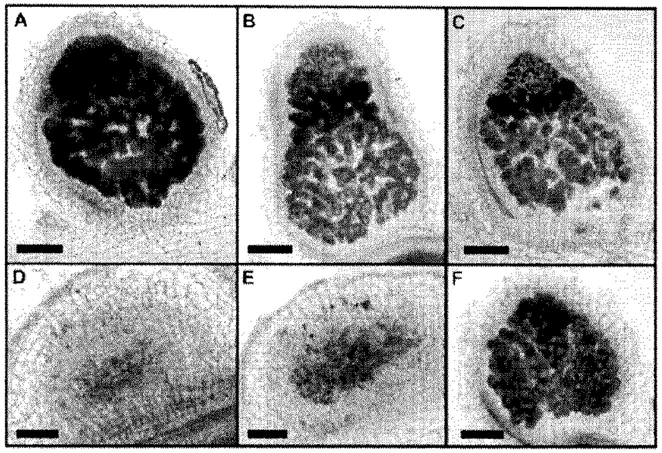

Figure 13

| Replicate | Oocytes | Average Histidine taken up per oocyte per hour (picomoles) |
|---|---|---|
| 1 | *MtNIP/LATD*-injected | 1.03 |
| 1 | water-injected | 1.65 |
| 2 | *MtNIP/LATD*-injected | 0.924 |
| 2 | water-injected | 1.31 |
| 3 | *MtNIP/LATD*-injected | 0.89 |
| 3 | water-injected | 1.35 |

Figure 14

| SEQ ID No.: | Primer Name | Primer Sequence | Purpose |
|---|---|---|---|
| SEQ ID No.: 9 | NIPC2F | 5'-TGAACCATGGAGTACACAAACAGTGATGATGCTAC | MtNIP/LATD cDNA forward primer, for binary vector |
| SEQ ID No.: 10 | NIPCODBstIR | 5'-AAAAAGGTCACCTATGAAGTAGGCAACTCCCTGT | MtNIP/LATD cDNA reverse primer, for binary vector |
| SEQ ID No.: 11 | CHL_1F | 5'-CAAGTCATGACTCTTCCTGAAACTAAATCTGATGATAT | AtNRT1.1 cDNA forward primer, binary vector |
| SEQ ID No.: 12 | CHL_1R | 5'-GAGCTGGTCACCTCAATGACCCATTGGAATACTCGGCTC | AtNRT1.1 cDNA reverse primer, binary vector |
| SEQ ID No.: 13 | NIPcDNANheIF | 5'-GCTAGCTAGCATGGAGTACACAAACAGTGATGATGCTA | Cloning MtNIP/LATD cDNAs in expression vector pcDNA™3.1(-) |
| SEQ ID No.: 14 | NIPcEXP1R | 5'-GTCGGATCCTATGAAGTAGGCAACTCCCTGTAAC | Cloning MtNIP/LATD cDNAs in expression vectors pcDNA™3.1(-) and pSP64T |
| SEQ ID No.: 15 | NIPcExp1F | 5'-CGAGGATCCATGGAGTACACAAACAGTGATGAT | Cloning MtNIP/LATD cDNAs in expression vector pSP64T |
| SEQ ID No.: 16 | PSP64T F1 | 5'- GGGTCTGCTTCAGTAAGCCAGATG | For PCR of T7-NIP from pSP64T-NIP/LATD vector |
| SEQ ID No.: 17 | PSP64T R1 | 5'-GATCCTCTAGAGTCGACCTGCAGG | For PCR of T7-NIP from pSP64T-NIP/LATD vector |
| SEQ ID No.: 18 | NIP 10F | 5'-TAAAATGAAAATCTGATACTAGAATTCAAG | MtNIP/LATD promoter forward primer, has endogenous EcoRI site |
| SEQ ID No.: 19 | NIP P1R | 5'-CACTGTTTGTGTACTTCATGATTCACTCTTCTTTGGTAGCTTCTTC | MtNIP/LATD promoter reverse primer, introduces BspHI site |
| SEQ ID No.: 20 | DC-BglII F | 5'-TCACTAGATCTATGGAGGAAAGCAAGAAGAGTTGC | AgDCAT1 forward primer, introduces BglII site |
| SEQ ID No.: 21 | DC NheI R | 5'-ATGCGCTAGCTCACACTTTTTCTTCTTTACCATT | AgDCAT1 reverse primer,introduces NheI site |

Figure 15

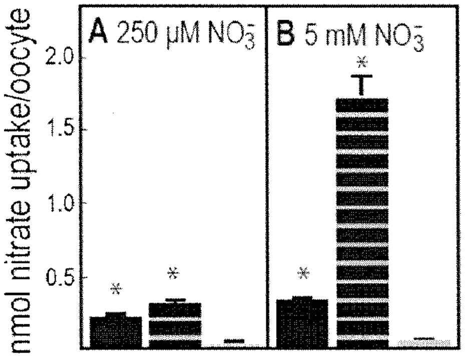
Figure 16
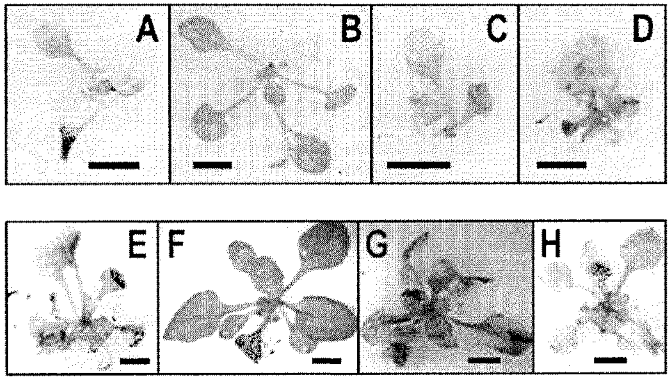
Figure 17
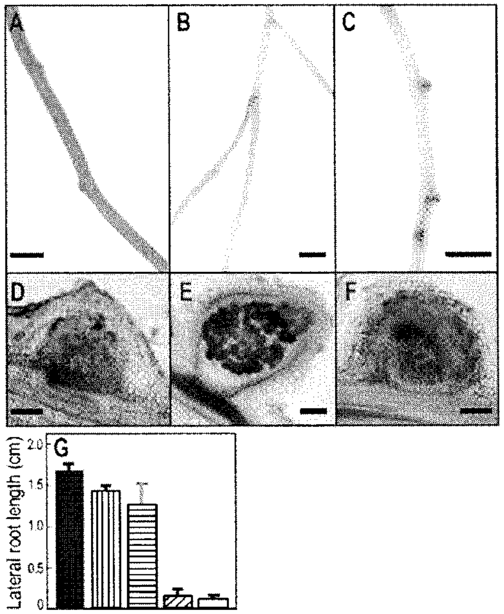
Figure 18
| Experiment | N conditions | A17 nodule number | *Mtnip-1* nodule number |
|---|---|---|---|
| | | | |
| 1 | no $NO_3$ | 31. 9 +/- 3.2 | 20.8 +/- 1.6 |
| 2 | no $NO_3$ | 19.9 +/- 4.1 | 13.25 +/- 0.8 |
| 3 | 1 mM $KNO_3$ | 7.8 +/- 0.7 | 2.2 +/- 0.4 |
| 4 | 1 mM $KNO_3$ | 5.3 +/- 0.6 | 1.1 +/- 0.3 |
| 5 | 5 mM $NH_4NO_3$ | 1.7 +/- 0.6 | 0. 7 +/- 0.2 |
| 6 | 5 mM $NH_4NO_3$ | 5.7 +/- 0.6 | 2.8 +/- 0.5 |
| 7 | 10 mM $KNO_3$ | 3.4 +/- 0.8 | 0.6 +/- 0.3 |
| 8 | 10 mM $KNO_3$ | 4.0 +/- 1.0 | 0.7 +/- 0.4 |
Figure 19

| Genotype | Fresh weight/plant (mg) | Chlorophyll content (mg/g fresh weight) |
|---|---|---|
| | | |
| Col-0 | 18.4 +/- 1.6 | 1.05 +/- 0.07 |
| *chl1-5* | 150.4 +/- 6.7 | 2.08 +/- 0.08 |
| *chl1-5*/p*AtEF1α-AtNRT1.1* | 20.9 +/- 1.5 | 0.92 +/- 0.06 |
| *chl1-5*/p*AtEF1α-MtNIP/LATD* | 21.7 +/- 0.9 | 1.15 +/- 0.15 |

*NIP/LATD* overexpressing lines make more nodules in 0 and 0.2 mM $KNO_3$, but not in 1 mM $KNO_3$ Nodule number is higher in *NIP/LATD* overexpressing lines in the secondary zone in 0 and 0.2 mM $KNO_3$, but not in 1 mM $KNO_3$ Nodule number is higher in *NIP/LATD* overexpressing lines in lateral roots in 0 and 0.2 mM $KNO_3$, but not in 1 mM $KNO_3$

*NIP/LATD* overexpressing lines have more lateral roots in 0 and 0.2 mM $KNO_3$, but not in 1 mM $KNO_3$

*MTNIP* REGULATED PLANTS WITH SIGNIFICANTLY INCREASED SIZE AND BIOMASS

RELATED APPLICATIONS

This application claims priority to U.S. Provisional Patent Application No. 61/554,836, filed Nov. 2, 2011, entitled "MtNIP REGULATED PLANTS WITH SIGNIFICANTLY INCREASED SIZE AND BIOMASS," having Rebecca Dickstein et al., listed as inventors and the entire content of which is hereby incorporated by reference.

FEDERALLY SPONSORED RESEARCH

This invention was made in part during work supported by a grant from the National Science Foundation, grant #IOS-0923756. The government has certain rights in the invention.

JOINT RESEARCH AGREEMENTS

Not Applicable.

SEQUENCE LISTING

Incorporated by reference in its entirety herein is a computer-readable nucleotide sequence listing submitted concurrently herewith and having the following listed sequences: SeqID No.: 1-SeqID No.: 29.

FIELD OF THE INVENTION

One aspect of the present invention relates generally to creating transgenic plants, and more specifically to the expression of the MtNIP (also called MtNIP/LATD and MtLATD/NIP) gene in plants to increase the biomass and size of the plants, and to cause earlier flowering, relative to wild-type plants.

BACKGROUND

All plants require nitrogen (N) as an essential nutrient and are able to acquire N from nitrate ($NO_3^-$) and ammonium ($NH_4^-$) in the soil. Nitrate acquisition begins with its transport into root cells, accomplished by $NO_3^-$ transporters. Soil $NO_3^-$ concentrations can vary by five orders of magnitude and plants have evolved both high-affinity (HATS) and low-affinity (LATS) nitrogen transport systems. These systems are encoded by two distinct gene families: the phylogenetically distinct NRT1(PTR) and NRT2 families. Members of these families also participate in movement of $NO_3^-$ throughout the plant and within plant cells. Proteins in the CLC transporter family also transport $NO_3^-$; these transporters are associated with cytosol to organelle $NO_3^-$ movement.

The nitrogen transporter "NRT1(PTR)" is a large family of transporters, comprising 53 members in *Arabidopsis,* 84 members in rice, with NRT1(PTR) members known in several other species. In addition to transporting $NO_3^-$ coupled to Fr movement, members of the NRT1(PTR) family have been found be a peptide transporter (PTR) capable of transporting di- or tripeptides, amino acids, dicarboxylic acids, auxin, and/or abscisic acid. One aspect of the current invention utilizes transgenic plants constitutively expressing a NRT1 (PTR) proteins to increase the biomass of plants and/or to decreasing the time needed to grow plants from seed until plants are mature enough to reproduce (flowering).

The plant biomass grown for commercial use is derived from a broad range of crops. Although a majority of crops around the world are grown for food resources, one use for the non-food portions a plant biomass is a renewable source of energy. This is typically conducted by converting the plant biomass into a biofuel. Well managed biomass systems continually grow/replace biomaterial. Biomass energy systems use different conversion and processing technologies to produce solid, liquid and gaseous biofuels. The plant from which the biomass is derived impacts which processes can be used to covert it to fuel, and also the efficiency of the resulting fuel. Furthermore, different crops and processes will yield different types and volumes of biofuels.

Because biomass can be used to create biofuels, methods of developing plants with increased biomass are of great interest to agricultural researchers and corporations. Moreover, some genetically modified plants that are expressing recombinant proteins have been shown to produce higher yield of biomass. While the number of crops genetically modified to have increased resistance to herbicide, insects, and drought conditions has grown significantly over the past decades, there has not been a similar increase in plants developed specifically to increase biomass.

In the US, renewable energy contributes around 7% to the national energy consumption, and nearly half of this renewable energy is derived from biomass. Currently, forests provide around 129 m dry tons of biomass annually, while agriculture provides a further 176 m dry tons. However, according to a study by the US Department of Agriculture and the US Department of Energy (DOE) these two sources could provide up to one billion dry tons (around 940,000 dry tons) of feedstock each year. On this basis biomass could supply 15% of US energy consumption by 2030. The US has a goal of generating one-third of all its liquid fuel from renewable resources by the year 2025, which could require up to 1 billion tons of biomass annually.

The *Medicago truncatula* (*Medicago*) MtNIP gene encodes a protein found in plants that is essential for symbiotic nitrogen-fixing root nodule and lateral root development (Veereshlingam et al., 2004; Yendrek et al., 2010). Plants that have defects in the MtNIP gene are able to initiate, but are unable to complete the development of, symbiotic nitrogen-fixing root nodules. These plants also have lateral roots that are incompletely formed (Veereshlingam et al., 2004). FIG. 1 shows the phenotypes observed.

Three mutant alleles of the MtNIP gene have been identified: nip-1, latd (nip-2) (Bright et al., 2005) and nip-3 (Teillet et al., 2008). Using these 3 alleles, one of the present inventors led a team of researchers to carry out a positional, map-based approach to clone the MtNIP gene (also called NIP/LATD or LATD/NIP) (Yendrek et al., 2010).

The MtNIP gene encodes a protein in the NRT1(PTR) transporter family (Yendrek et al., 2010), primarily composed of proton-coupled low affinity nitrate and di- and tri-peptide transporters (Tsay et al., 2007) (FIG. 2). The family also includes a dicarboxylate transporter (Jeong et al., 2004). Recently, the dual affinity nitrate transporter AtNRT1.1, also called CHL1 because of its ability to transport the herbicide chlorate, has been show to function as a nitrate sensor (Ho et al., 2009; Wang et al., 2009) and as an auxin transporter (Krouk et al., 2010).

One aspect of the present invention provides a means of increasing the biomass of plants, as compared to wild-type plants, by over-expressing the MtNIP gene in the plants. Although not wanting to be bound by theory, this finding has implications for genetically engineering crop plants to have greater yield, and also has implications for genetically engineering plants that might be used in production of biofuels, as well as increasing yield for food, fiber and industrial applications.

*Arabidopsis thaliana*, a dicot, was adopted by the scientific community as a plant model, with the underlying assumption that for most physiological, developmental and genetic processes, it would behave like other plants. It is now considered the reference plant (NSF, 2002; Flavell, 2005). Knowledge gained through the use of *Arabidopsis* would be applicable to all plants, including crop plants, even though many crop plants are monocots. This is based on evolutionary principles that state that beneath the diversity present in plants that there are core processes and genetic mechanisms that are conserved among all plants (Flavell, 2005). Large scale genome sequencing of the much larger genomes in crop species has begun to show that these species have conserved genes with *Arabidopsis*, although there are frequent gene rearrangements and gene duplications when one compares *Arabidopsis* to a crop species (Ware and Stein, 2003; Flavell, 2005). There are numerous examples of genes being tested first in *Arabidopsis*, because *Arabidopsis* is fast, and subsequent testing in a crop species, leading to improvement of the crop species: (Bhatnagar-Mathur et al., 2008; Manavalan et al., 2009; Valente et al., 2009; Hussain et al., 2011).

Other examples of *Arabidopsis* genes being used to improve crop plants or *Arabidopsis* research paving the way for translational changes in crop plants can be found in Zhang et al (2004) (Zhang et al., 2004). The article lists specific examples of specific genes that were tested first in *Arabidopsis* and have been used to improve the crop plants *Brassica napus*, tomato, rice, wheat, strawberry, maize and tobacco. More recent examples show that ERF transcription factor genes that are involved in regulating stress responses in *Arabidopsis* have been transformed into crop plants rice (Gao et al., 2008; Zhang et al., 2010; Zhang et al., 2010), tomato, and tobacco (Zhang and Huang, 2010), forage clovers (Abogadallah et al., 2011), and alfalfa (Jin et al., 2010), with benefits to the recipient crop plant. In these cases, the transferred gene did not always come from *Arabidopsis*, but the groundwork experiments were done in *Arabidopsis*. Although not wanting to be bound by theory, the behavior of MtNIP-transformed *Arabidopsis* plants will predict other plants that have MtNIP-transformed into them, or are MtNIP-transformed.

SUMMARY

Broadly, one aspect of the present invention involves creating a transgenic plant, where one or more cells of a parent plant of the transgenic plant have been transformed with a vector containing a certain gene. Another aspect of the present invention pertains to the discovery that over-expression of the MtNIP gene in a plant causes the plant to develop a significant increase in biomass and size, as well as earlier flowering, as compared to those of wild-type plants or parent plants of the transgenic plants. In one embodiment, the MtNIP gene was over-expressed in the model plant *Arabidopsis thaliana*. In another embodiment, the gene has a modified gene sequence of SEQ ID NO:2 or SEQ ID NO:8.

In other embodiments of the invention, other genes in the NRT1(PTR) family may be over-expressed in plants to result in increased biomass, plant growth, and early flowering, as compared to wild-type plants or parent plants. The gene may be one of the 53 members of the NRT1/PTR family *Arabidopsis* or the 80 members in rice or other genes in the NRT1 (PTR) family in other plants.

A first aspect of the current invention includes a transgenic plant having a promoter nucleotide sequence that is capable of initiating transcription of an operably linked heterologous nucleic acid sequence in a plant cell, wherein the operably linked heterologous nucleic acid sequence expresses a protein in the NRT1(PTR) transporter family. Although not wanting to be bound by theory, the promoter need only be capable of initiating transcription of an operably linked heterologous gene in the plant cell, the sequence or origine of the promoter is not vital. However, in a first preferred embodiment the promoter nucleotide sequence has at least 95% identity to SEQ ID NO:22 or SEQ ID NO.: 29. The promoter nucleotide sequence and the operably linked heterologous nucleic acid sequence expressing the NRT1(PTR) transporter family protein have at least 95% identity to SEQ ID NO:23 or SEQ ID No.: 25. In a second preferred embodiment, the operably linked heterologous nucleic acid sequence has at least 95% identity to SEQ ID NO: 2; or SEQ ID NO: 8. In a third preferred embodiment, the plant cell comprises an *Arabidopis thaliana* plant cell; a *M. truncatula* plant cell; or a tobacco plant cell. A quality of the transgenic plant is the biomass of the transgenic plant increases over a period of time when compared to a non-transformed plant of a same plant family phylum for the same period of time. Additionally, a seed of the transgenic plant, or parts thereof are include in the present invention.

A second aspect of the current invention includes a method for increasing the biomass of a plant. Generally, the method comprises transforming the plant with a vector capable of initiating transcription of an operably linked heterologous nucleic acid sequence in a plant cell, wherein the operably linked heterologous nucleic acid sequence expresses a protein in the NRT1(PTR) transporter family. One preferred embodiment of this aspect of the invention includes a step of selecting a promoter nucleotide sequence having at least 95% identity to SEQ ID NO:22 or SeqID No.: 29 to be used for initiating the transcription of the operably linked heterologous nucleic acid sequence. A second preferred embodiment of includes an additional step of selecting the operably linked heterologous nucleic acid sequence to express the NRT1 (PTR) transporter protein having an amino acid comprising at least 95% identity to SEQ ID NO: 2; or SEQ ID NO: 8. Additionally, further steps of selecting the vector comprising at least 95% identity to SEQ ID NO: 26; SEQ ID NO: 27; or SEQ ID NO: 28; have been used. In another preferred embodiment, the method further comprises a step of selecting the plant from an *Arabidopis thaliana* plant family phylum; a *M. truncatula* plant family phylum; or a tobacco plant family phylum. When a step of comparing the biomass of the transgenic plant over a period of time is compared to a non-transformed plant of a same plant family phylum for the same period of time, the biomass of the transgenic plant is increased. Similarly, a flowering event of the transgenic plant occurs at an earlier period of time when compared to a non-transformed plant of a same plant family phylum for the same period of time. Moreover, the number of overall root nodules in the transgenic plant is increased over a period of time when compared to a non-transformed plant of a same plant family phylum for the same period of time, and a proliferation of lateral roots in the transgenic plant grown in low nitrogen conditions is increased over a period of time when compared to a non-transgenic plant of a same plant family phylum for the same period of time.

A third aspect of the current invention is a method for generating transgenic seeds for plants having an increased biomass or early flowering potential. The method comprises the steps o: (a) multiplying plant cells that contain at least one genetic transformation event of interest and which are capable of regeneration; wherein the genetic transformation event comprises incorporating a promoter nucleotide sequence that is capable of initiating transcription of an operably linked heterologous nucleic acid sequence expressing a protein having at least 97% identity to SEQ ID NO 8 into said plant cells; (b) selecting the plant cells that comprise at least one genetic transformation event of interest; (c) regenerating whole transgenic plants, termed primary transformants, or $T_0$ plants, from said plant cells; (d) pollinating said primary transformants with non-transgenic pollen; (e) harvesting the seeds obtained, termed $T_1$, which have integrated at least one transgene of interest; (f) sowing said transgenic $T_1$ seeds and pollinating the plants which result therefrom, either by self-pollination or by free pollination; and (g) harvesting the $T_2$ seeds. A preferred embodiment includes an additional step of carrying out post-harvest phenotypic sorting of the $T_2$ seeds. An additional preferred step includes selecting an *Arabidopis thaliana* plant cell; a *M. truncatula* plant cell; or a tobacco plant cell for genetic transformation.

A fourth aspect of the current invention is an isolated transformation vector construct having a promoter region and an expression region having at least 95% homology with SeqID No.: 23, SeqID No.: 24, or SeqID No.: 25.

A fifth aspect of the current invention uses an isolated transformation vector construct having at least 95% homology with SeqID No.: 26, SeqID No.: 27, or SeqID No.: 28.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 13 shows *Arabidopsis* NRT1.1 does not complement the *Medicago* nip-1 nodule phenotype. *Medicago* nip-1 and control wild-type composite plants transformed with pAtEF1α-AtNRT1.1, empty vector pCAMBIA2301 as negative control, or pAtEF1α-MtNIP/LATD were grown in as in FIG. 11, with *S. meliloti* containing a constitutive lacZ gene. At 15 days post-inoculation, nodule characteristics were evaluated after staining with X-Gal for localization of rhizobia, which stain blue and are shown as black spots. Panel A, A17 transformed with empty vector. Panel B, A17 transformed with pAtEF1α-AtNRT1.1. Panel C. A17 transformed with pAtEF1α-MtNIP/LATD. Panel D, Mtnip-1 transformed with empty vector. Panel E, Mtnip-1 transformed with pAtEF1α-AtNRT1.1. Panel F, Mtnip-1 transformed with pAtEF1α-MtNIP/LATD. Bars=200 μm.

FIG. 14 shows a table having MtNIP/LATD-expressing oocytes do not take up histidine. For each replicate, eight oocytes, injected with either MtNIP/LATD in vitro-transcribed RNA or with water as a control, were incubated with uniformly labeled $^{13}C$-histidine. Supernatants from lysed oocytes were derivatized with 6-aminoquinolyl-N-hydroxysuccinimidyl carbamate. Histidine quantitation was accomplished using ultra performance liquid chromatography-electrospray ionization-tandem mass spectrometry. See Materials and Methods for experimental details.

FIG. 15 shows a table of Sequences of oligonucleotide primers used in this invention.

FIG. 16 shows a Comparison of nitrate uptake in oocytes expressing MtNIP/LATD versus AtNRT1.1. Oocytes were microinjected with MtNIP/LATD mRNA (black bars), AtNRT1.1 mRNA (horizontally striped bars) or water as a negative control (gray bars), incubated for 2 days, then placed in media containing 250 μM or 5 mM $NO_3^-$ at pH 5.5. The oocytes were rinsed, lysed and assayed for $NO_3^-$ uptake. Panel A, 250 μM $NO_3^-$. Panel B. 5 mM $NO_3^-$. Data are shown for one biological replicate plus or minus the standard deviation; n=5 batches of 4-6 oocytes per batch. Asterisks mark $NO_3^-$ uptake significantly different from the negative control, using Student's t-test at $p<0.05$. Similar results were obtained in two repetitions of the experiment.

FIG. 17 shows MtNIP/LATD complements the chlorate insensitivity phenotype of the *Arabidopsis* chl1-5 mutant. *Arabidopsis* chl1-5 plants were transformed with a construct containing MtNIP/LATD cDNA under the control of the *Arabidopsis* ET1αpromoter, pAtEF1α-MtNIP/LATD or a positive control construct containing the *Arabidopsis* AtNRT1.1 gene under the same promoter, pAtEF1α-AtNRT1.1. All plants were treated with chlorate as described in Tsay et al. 1993. Plants in panels A-D were handled together as were plants in panels E-H. A, *Arabidopsis* Col-0. B, *Arabidopsis* chl1-5. C, *Arabidopsis* chl1-5/pAtEF1α-AtNRT1.1 D, *Arabidopsis* chl1-5/pAtEF1α-MtNIP/LATD, transformant 1. E, *Arabidopsis* Col-0. F, *Arabidopsis* chl-5. G, *Arabidopsis* chl1-5/pAtEF1α-MtNIP/LATD-1. H, *Arabidopsis* chl1-5/pAtEF1α-MtNIP/LATD transformant 2. The MtNIP/LATD gene was able to confer chlorate sensitivity on *Arabidopsis* chl1-5 plants, similar to the AtNRT1.1 gene.

FIG. 18 shows AgDCAT1 does not complement the Mtnip-1 mutant. *Medicago* nip-1 and control A17 wild-type composite plants transformed with pMtNIP/LATD-MtNIP/LATD, pMtNIP/LATD-AgDCAT1, or empty vector pCAMBIA as negative control, were grown as in FIG. 5. Panels A and D, Mtnip-1 transformed with empty vector. Panels B and E, Mtnip-1 transformed with pMtNIP/LATD-MtNIP/LATD. Panels C and F, Mtnip-1 transformed with pMtNIP/LATD-AgDCAT1. Panels A-C, roots; bars=5 mm. Panels D-F, nodules; blue but represented as a black color indicates rhizobia stained with X-Gal; bars=200 μm. Panel G. Quantitation of lateral root length. Averaged values with the standard deviation are plotted; n=5. Black bars: A17, empty vector. Vertical striped bars: A17, pMtNIP/LATD-AgDCAT1. Horizontal-stripped bars: Mtnip-1, pMtNIP/LATD-MtNIP/LATD.

Diagonal-stripped bars, Mtnip-1, empty vector. White bars: Mtnip-1, pMtNIP/LATD-AgDCAT1.

FIG. 19 shows a Table of Nodulation in the absence and presence of N sources. In each experiment, wild-type A17 and Mtnip-1 plants were grown in the same aeroponic chamber in the given N regime, as described in Materials and Methods. For each experiment, 7 to 11 plants of each genotype were evaluated. Nodules were counted at 15 days post inoculation (dpi). Data are presented as the mean number of nodules per plant plus or minus the standard error of the mean.

Figures 20, 21:
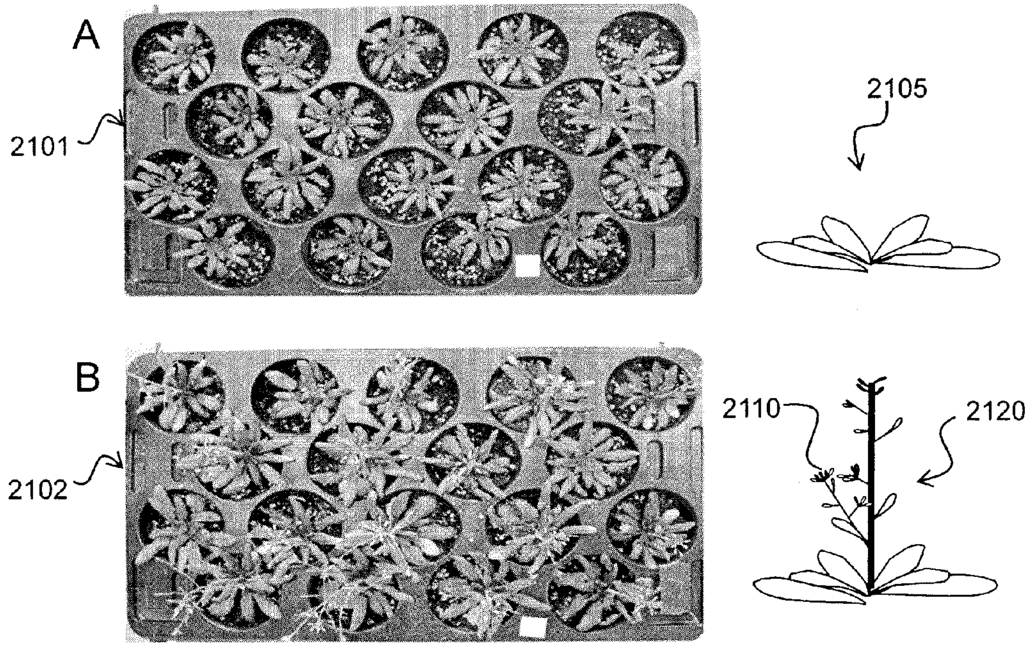

FIG. 20 shows a Table of Fresh weight and chlorophyll content of chlorate treated *Arabidopsis* plants. Plants were grown in vermiculite: perlite (1:1) and irrigated with media containing 5 mM $NO_3^-$ for 5-7 days. Plants were then irrigated with $ClO_3^-$-containing media without $NO_3^-$ for 3 days, and subsequently with media lacking both $ClO_3^-$ and $NO_3^-$. Fresh weight and chlorophyll content were obtained from plants 7-10 days after $ClO_3^-$ treatment. Each data point represents 7-9 plants. Two independent replicates gave similar results.

FIG. 21 shows a comparison of wild-type non-transformed *Arabidopsis* and *Arabidopsis* constitutively expressing MtNIP/LATD using constitutive AtEF1αPromoter.

Figure 22:
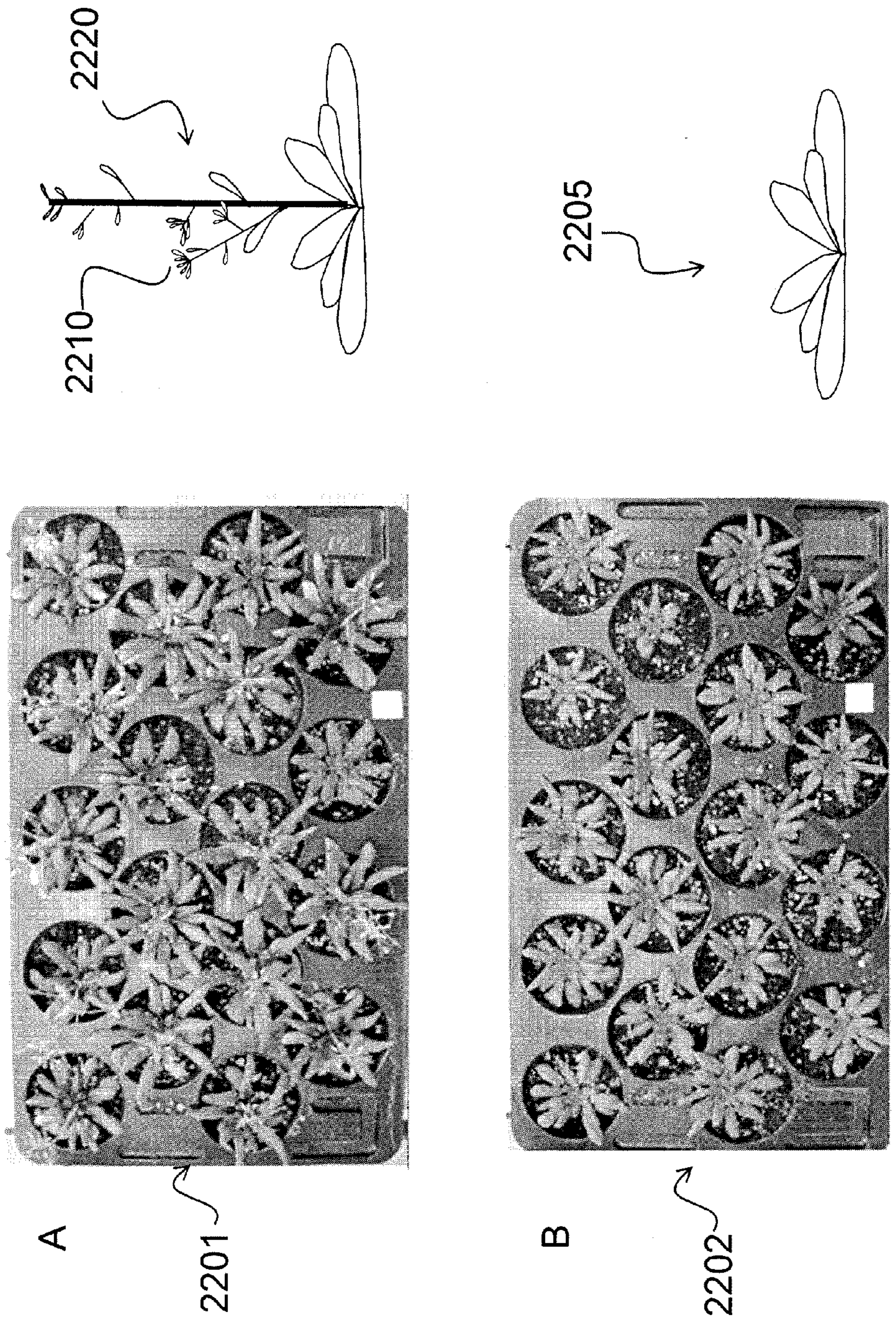

FIG. 22 shows a comparison of an *Arabidopsis* plant constitutively expressing MtNIP-3 and another *Arabidopsis* plant constitutively expressing MtNIP-1 using constitutive AtEF1αPromoter.

Figure 23:
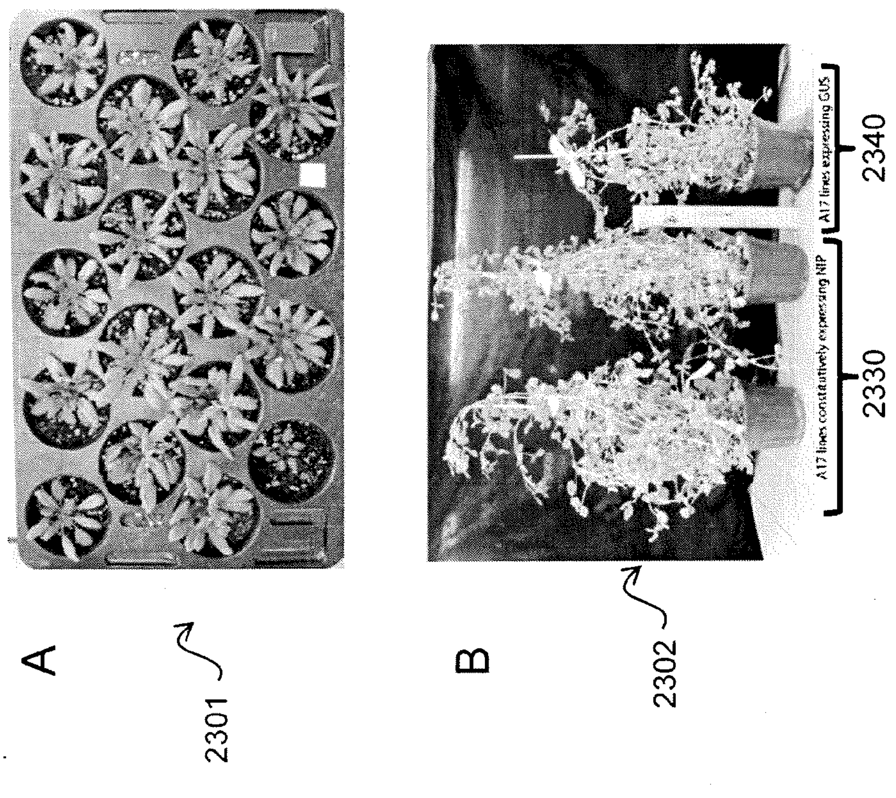

FIG. 23 Panel A shows a comparison of an *Arabidopsis* plant constitutively expressing AtNRT1.1 using constitutive AtEF1αPromoter, which causes slightly larger plants and several of the plants to flower earlier. Panel B shows how two plants constitutively expression gMtNIP/LATD are larger and flowering earlier than the plant on the right expressing an unrelated gene GUS.

Figure 24:
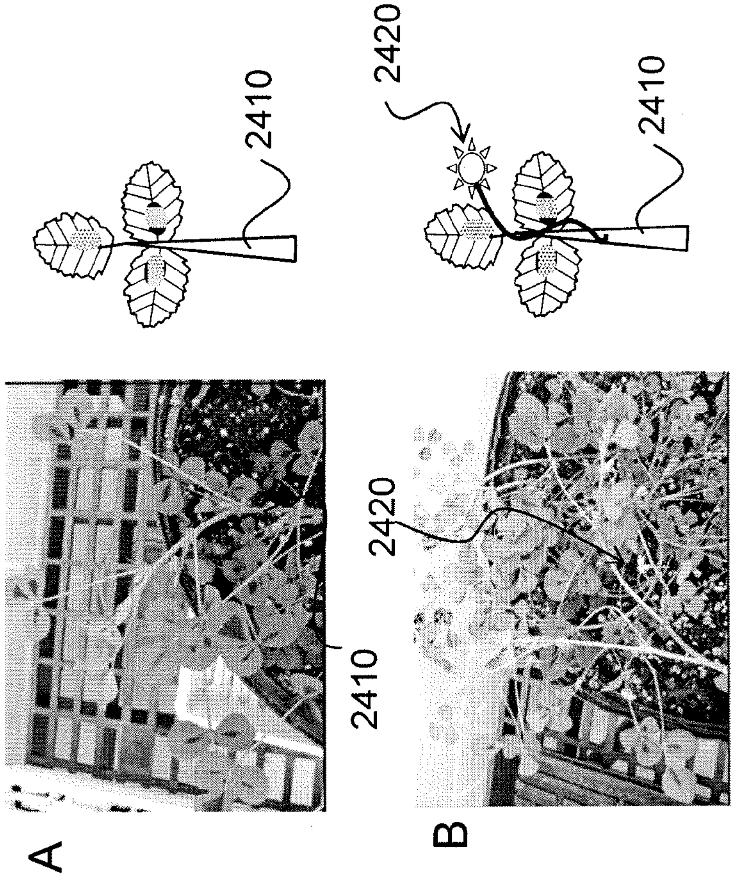

FIG. 24 shows a comparison of *M. Truncatula* plants transformed with GUS and *M. Truncatula* constitutively expressing MtNIP/LATD using constitutive AtEF1αPromoter.

Figure 25:
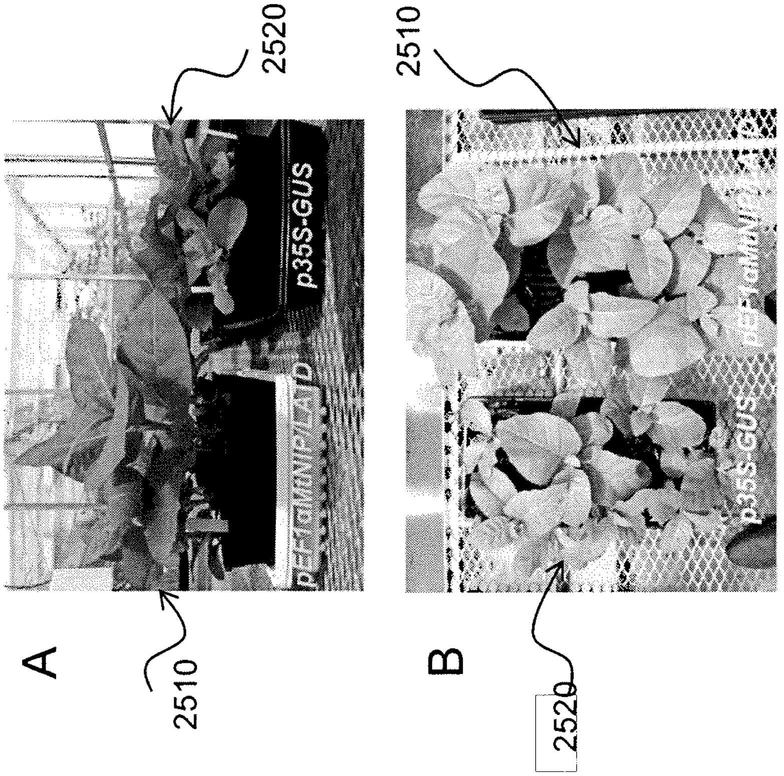

FIG. 25 shows a comparison of tobacco plants transformed with GUS and tobacco plants constitutively expressing MtNIP/LATD.

Figure 26:
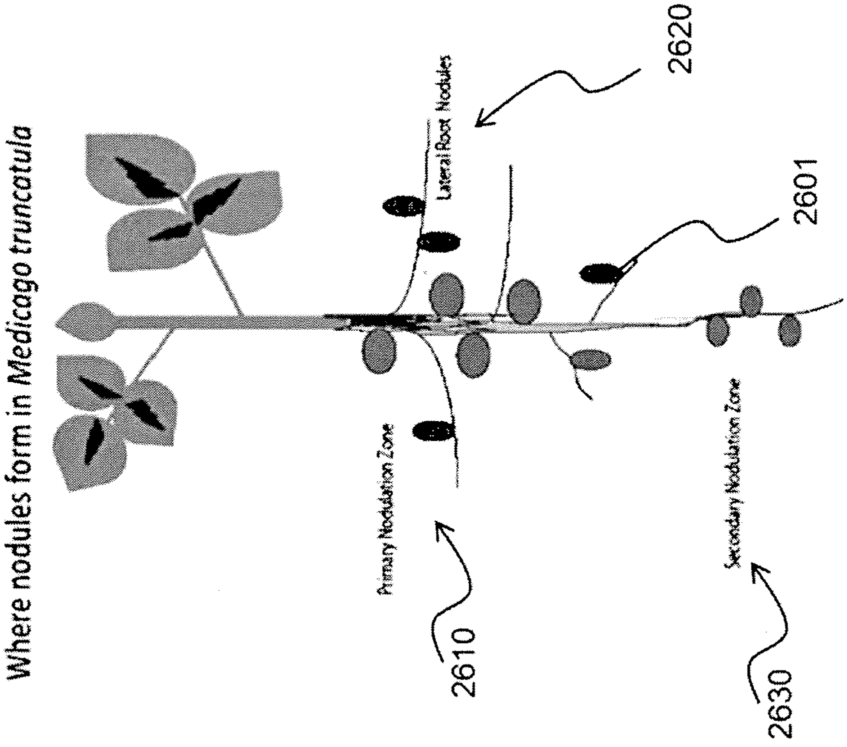

FIG. 26 shows an illustration of locations of nodules in the *M. Truncatula* plant.

Figure 27:
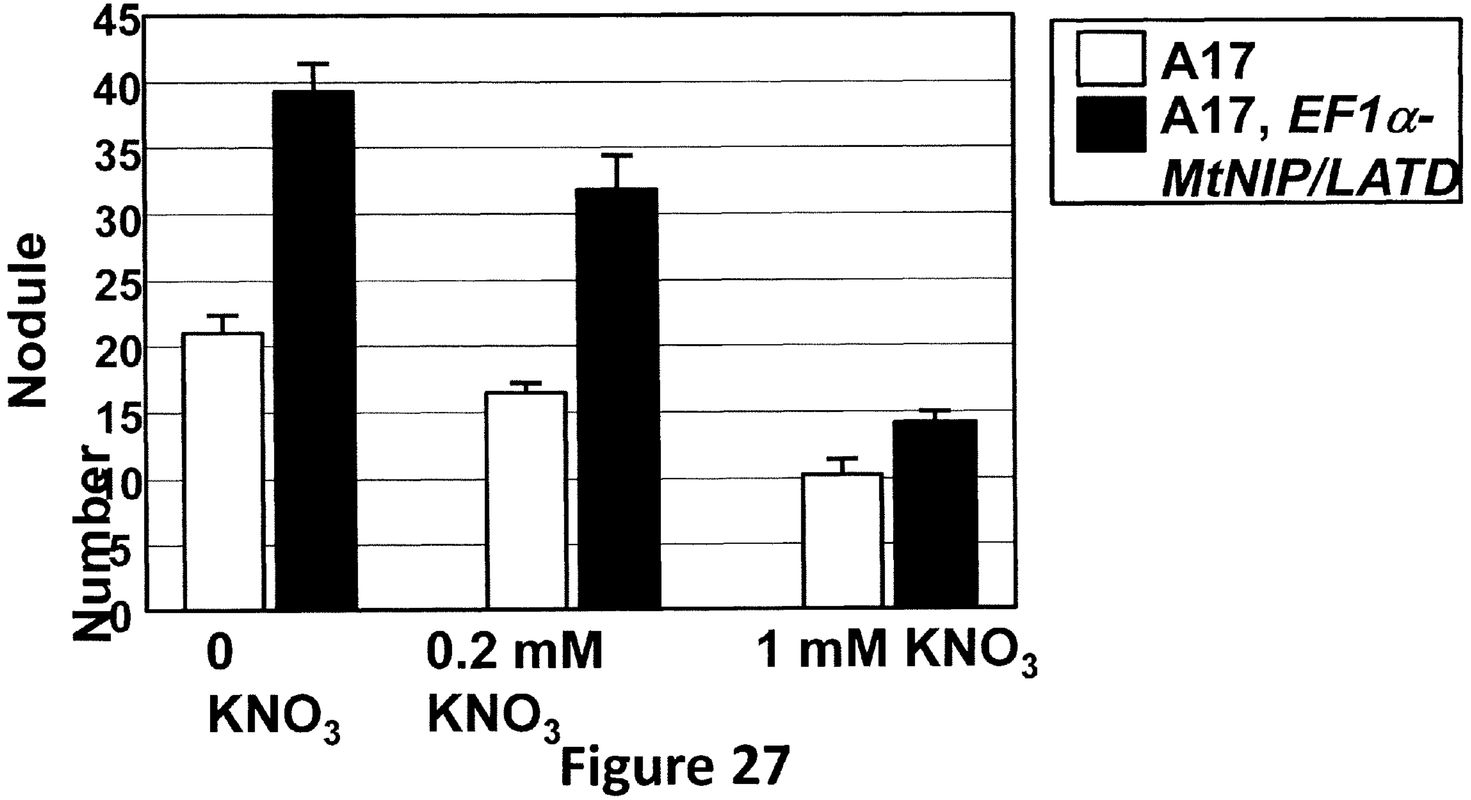

FIG. 27 shows a comparison of total nodule number per plant in wild-type non-transformed *M. Truncatula* and *M. Truncatula* constitutively expressing MtNIP/LATD grown in different concentrations of $KNO_3$.

Figure 28:
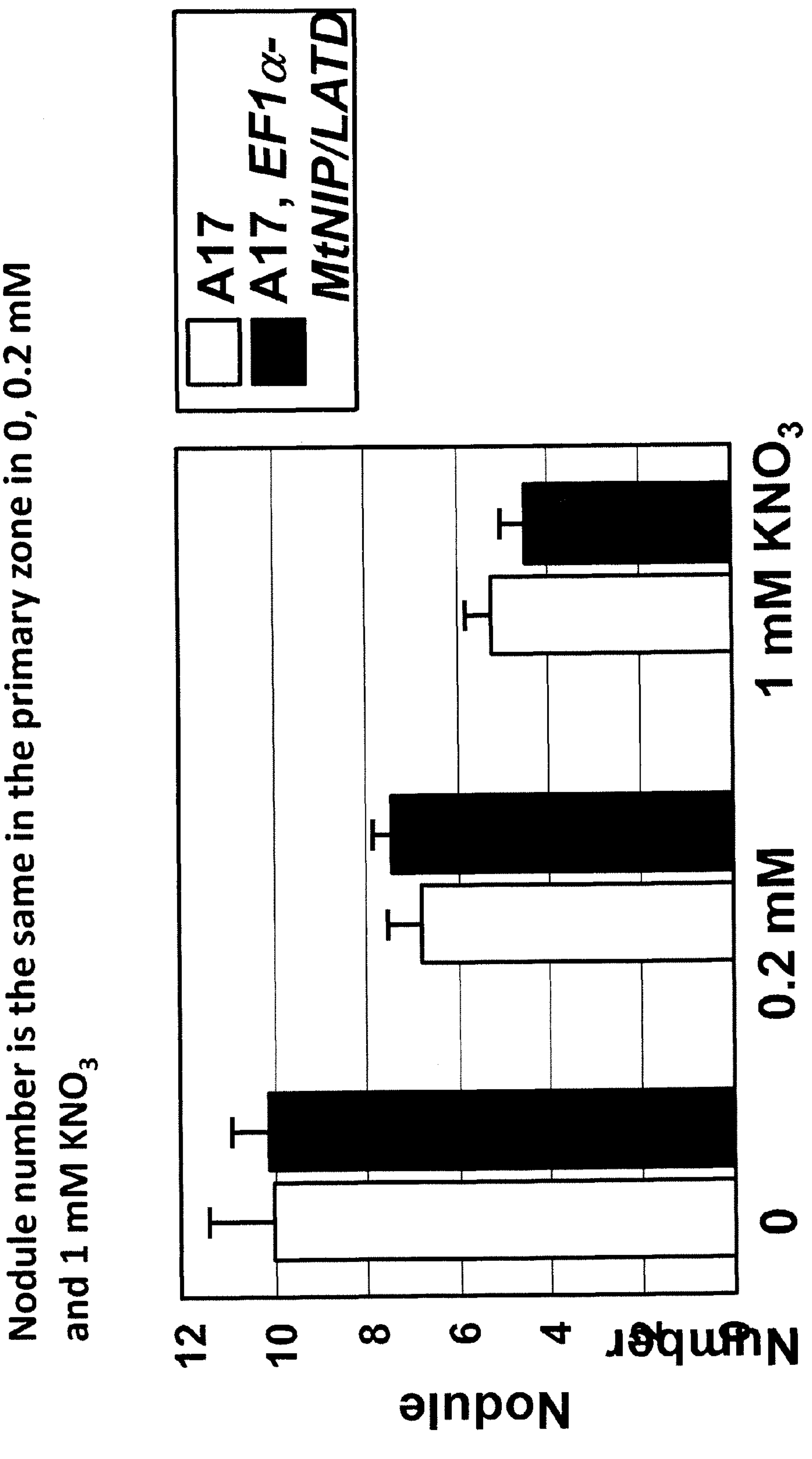

FIG. 28 shows a comparison of average number of nodules located in the primary zone in wild-type non-transformed *M. Truncatula* and *M. Truncatula* constitutively expressing MtNIP/LATD grown in different concentrations of $KNO_3$.

Figure 29:
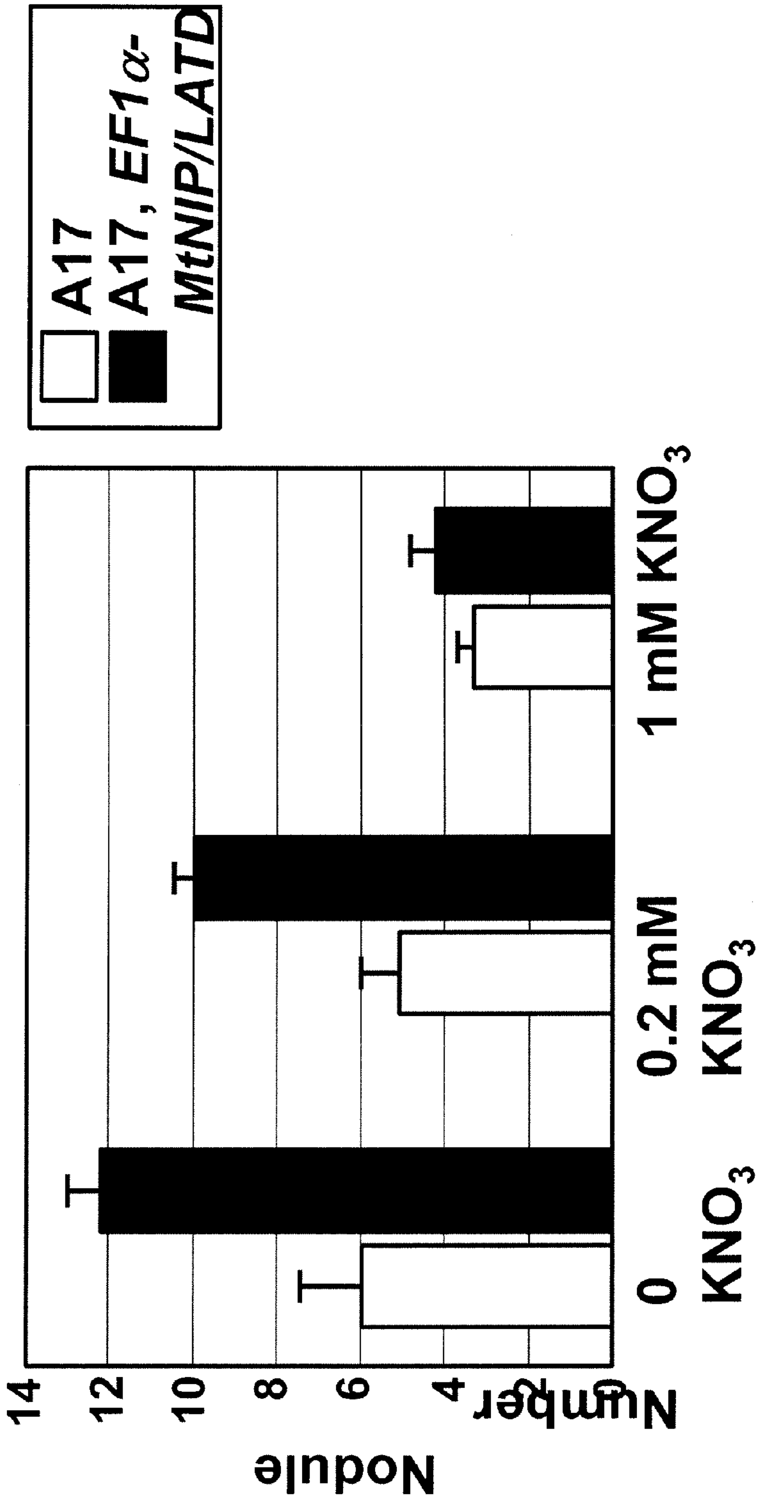

FIG. 29 shows a comparison of average number of nodules located in the secondary zone in wild-type non-transformed *M. Truncatula* and *M. Truncatula* constitutively expressing MtNIP/LATD grown in different concentrations of $KNO_3$.

Figure 30:
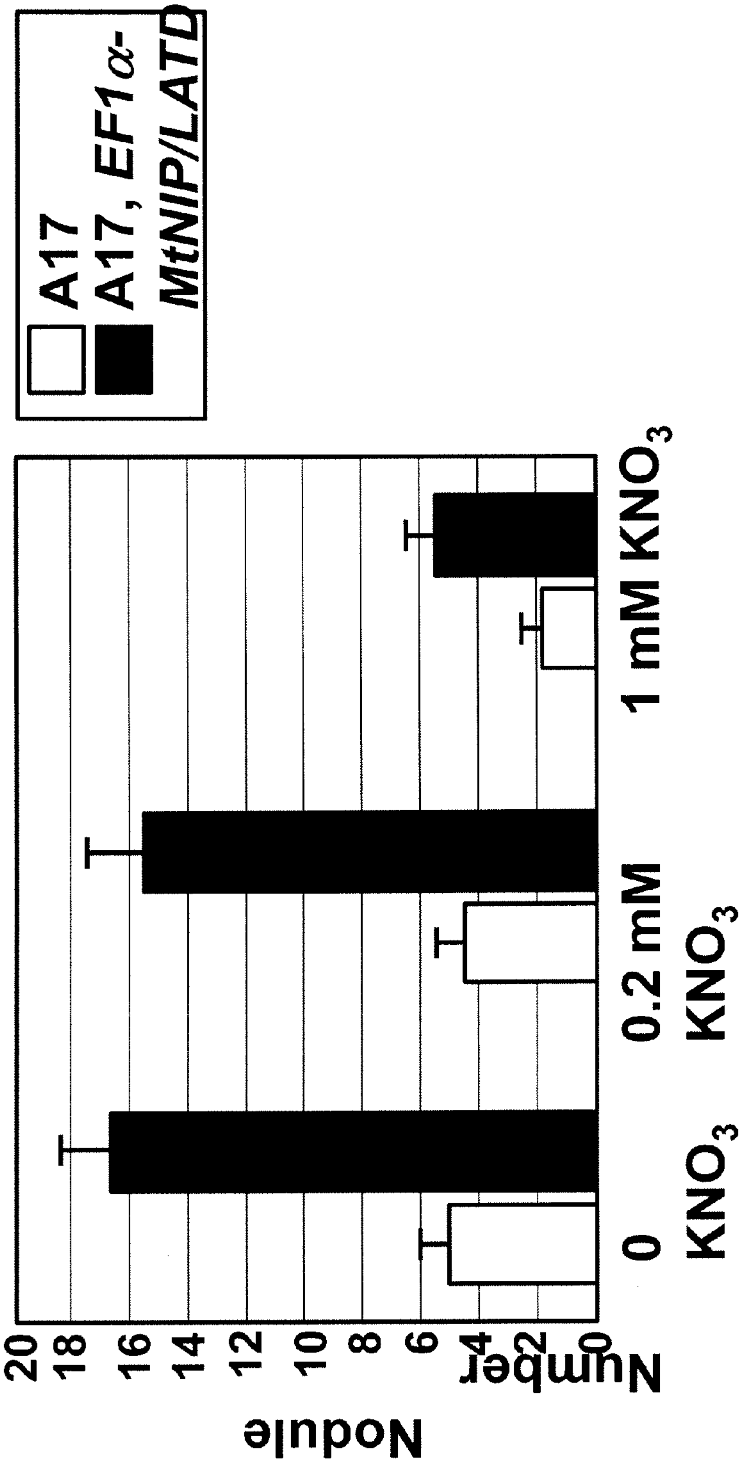
Figure 31:
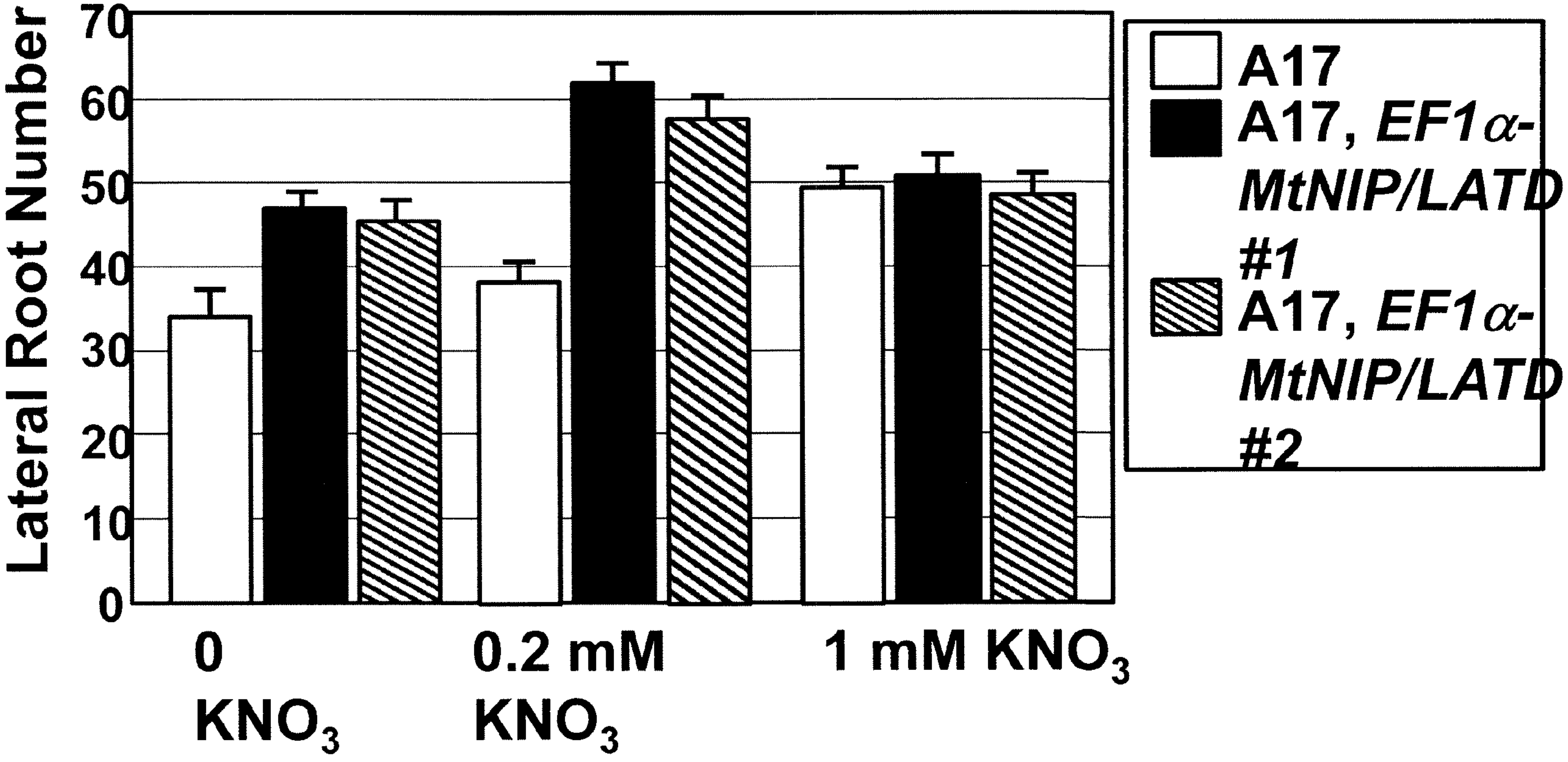

FIG. 30 shows a comparison of average number of nodules located in the lateral roots in wild-type non-transformed *M. Truncatula* and *M. Truncatula* constitutively expressing MtNIP/LATD grown in different concentrations of $KNO_3$ FIG. 31 shows comparison of average number of nodules located in the lateral roots of MtNIP/LATD overexpressing lines and in wild-type non-transformed *M. Truncatula* grown in different concentrations of $KNO_3$.

DETAILED DESCRIPTION OF PREFERRED EMBODIMENTS

Broadly, one aspect of the present invention involves creating a transgenic plant, where one or more cells of a parent plant of the transgenic plant have been transformed with a vector containing a certain gene. Generally, it is believed that the transformation is almost complete. A further aspect of the present invention includes the discovery that over-expression of the MtNIP gene in a plant causes the plant to develop a significant increase in biomass. In one embodiment, the MtNIP gene was over-expressed in the model plant *Arabidopsis thaliana* (*Arabidopsis*). The transgenic plants have modified growth characteristics, such as size, biomass, and flowering time.

In another aspect of the present invention, it is shown that MtNIP protein is a high affinity proton coupled nitrate transporter, and also functions to increase plant biomass as well as size and to promote early flowering, as compared to those of wild-type plants or parent plants of the transgenic plants.

DEFINITIONS

The *Medicago truncatula* (*Medicago*) MtNIP gene (also called NIP/LATD or LATD/NIP) encodes a protein in the NRT1(PTR) transporter family found in plants that is essential for symbiotic nitrogen-fixing root nodule and lateral root development. Plants that have defects in the MtNIP gene are able to initiate, but are unable to complete the development of symbiotic nitrogen-fixing root nodules. The *M. truncatula* NIP/LATD gene sequence (SEQ ID No.: 1) (gi|262181250|gb|GQ401665.1| *Medicago truncatula* LATD/NIP cDNA, complete cds) is as follows:

```
ATGGAGTACACAAACAGTGATGATGCTACAAATGAAAAACTCATTGAAAATGGCAGCTCTTCATCATCTT

CTCAACCGAGAAAGGGTGGTTTAAGAACCATGCCCTTTATCATAGTGAATGAGTGTCTTGAGAAAGTGGC

AAGTTATGGAATAATGCCAAACATGATATTATACTTGAGGGATGATTATAACATGCCTATTGCTAAGGCT

AGTTATGTTCTTTCTACTTGGTCTGCTATGTCCAATGTTTTGTCCATCTTTGGTGCTTTTCTCTCTGATT

CTTACTTGGGTCGCTTCAATGTCATCACTATTGGCTCCTTTTCTAGCCTTCTTGGTTTAACCGTTTTGTG

GTTAACTGCCATGATCCCGGTGCTAAAACCTACCTGTGCATCACTCTTTGAAATCTGTAATTCTGCTACT

TCATCCCAACAAGCAGTTCTGTTCCTTTCCTTAGGATTAATTTCAATTGGAGCTGGTTGTGTTAGACCTT

GTTCCATAGCCTTTGGAGCAGAGCAATTGACTATTAAGGGAAATTCTGGTGATGGGAATGGCAGGATCTT

GGATAGTTACTTTAATTGGTATTATACCTCAATTTCAGTTTCAACCATTATCGCGTTGAGTGTGATTGCT

TACATTCAAGAAAACCTTGGATGGAAAATTGGGTTTGGAGTACCTGCTGTGCTAATGCTCGTATCGGTCA
```

-continued

TCAGTTTCATTATTGGTTCACCGTTATATGTCAAAGTGAAGCCAAGTGAAAGCTTACTCACTAATTTTGC

AAGAGTAGTTGTGGTGGCAACCAAGAACAGAAAACTTAGTCTTCCTGATGACGACTCTGATCGTTACTGT

CAAGGTCATGATTCAAAGCTGAAGGTTCCTACCGATAGCCTTAGGTTTTTGAACAAAGCTTGCGTAATAA

GAAATCCTGAGACAGATCTTAATCGAGATGGGTCAATTTCAAATCCGTGGAACCTATGCACAATAGAACA

GGTGGAGTCACTGAAGTCTTTGCTCAGAGTCATTCCTATGTGGTCAACGGGAATCTTTATGATGGCGACT

CAGAGTTCATTTTCTACTCTTCAAGCCAAAACTTTGAACCGAACGTTATTCGGCAATTTCAATTTTCCTG

CAGGATCGTTCAATCTTATCTTGATATTCACCTTAACAATAGTAATTCCTTTATATGACCGTGTAGGAGT

ACCTCTACTAGCTAAATACGCAGGCCGGCCTAGAGGATTCAGTTTTAAAGTCCGCATCGGGATAGGAATG

CTGTTTGCAATTGTAGCTAAAGCAGTAGCAGCTATTGTTGAAACGGTGAGACGAAATGCAGCGATTGAAC

AAGGGTTTGAGGACCAACCTAATGCTGAAATTAACATGTCGGCTTTATGGCTTGCTCCAGAGTTTATTTT

GTTTGGATTCGCCGAAGCTTTCACACCAGTTGGACTGGTTGAGTTTTTCTACTGTTTTTTCCCTAAGAGT

ATGTCTAGTTTTGCAATGGCTATGTTCACATTGGGACTAGCTTGTTCTGACGTAGTTTCAGGTGTGCTTG

TGAGCATTGTGGACACGGTCACTAGTATTGGAGGGAATGAGAGCTGGTTATCGACTAACATCAATAGGGG

ACATTTGAATTACTACTACGGGCTACTCACTTTCTTAGGCATTCTTAACTACTTCTATTATCTTGTTATT

TGTTGGGCTTATGGACCCATACAGGGAGAGAAACATGAAGATTCGGCCAGAAAGAAAGACGATAAATTTG

GTTACAGGGAGTTGCCTACTTCATAG

The MtNIP gene encodes a protein having the amino acid sequence (SEQ ID No.2):

MetGluTyrThrAsnSerAspAspAlaThrAsnGluLysLeuIleGluAsnGlySerSer

SerSerSerSerGlnProArgLysGlyGlyLeuArgThrMetProPheIleIleValAsn

GluCysLeuGluLysValAlaSerTyrGlyIleMetProAsnMetIleLeuTyrLeuArg

AspAspTyrAsnMetProIleAlaLysAlaSerTyrValLeuSerThrTrpSerAlaMet

SerAsnValLeuSerIlePheGlyAlaPheLeuSerAspSerTyrLeuGlyArgPheAsn

ValIleThrIleGlySerPheSerSerLeuLeuGlyLeuThrValLeuTrpLeuThrAla

MetIleProValLeuLysProThrCysAlaSerLeuPheGluIleCysAsnSerAlaThr

SerSerGlnGlnAlaValLeuPheLeuSerLeuGlyLeuIleSerIleGlyAlaGlyCys

ValArgProCysSerIleAlaPheGlyAlaGluGlnLeuThrIleLysGlyAsnSerGly

AspGlyAsnGlyArgIleLeuAspSerTyrPheAsnTrpTyrTyrThrSerIleSerVal

SerThrIleIleAlaLeuSerValIleAlaTyrIleGlnGluAsnLeuGlyTrpLysIle

GlyPheGlyValProAlaValLeuMetLeuValSerValIleSerPheIleIleGlySer

ProLeuTyrValLysValLysProSerGluSerLeuLeuThrAsnPheAlaArgValVal

ValValAlaThrLysAsnArgLysLeuSerLeuProAspHisAspSerAspArgTyrCys

GlnGlyHisAspSerLysLeuLysValProThrAspSerLeuArgPheLeuAsnLysAla

CysValIleArgAsnProGluThrAspLeuAsnArgAspGlySerIleSerAsnProTrp

AsnLeuCysThrIleGluGlnValGluSerLeuLysSerLeuLeuArgValIleProMet

TrpSerThrGlyIlePheMetMetAlaThrGlnSerSerPheSerThrLeuGlnAlaLys

ThrLeuAsnArgThrLeuPheGlyAsnPheAsnPheProAlaGlySerPheAspLeuIle

LeuIlePheThrLeuThrIleValIleProLeuTyrAspArgValGlyValProLeuLeu

AlaLysTyrAlaGlyArgProArgGlyPheSerPheLysValArgIleGlyIleGlyMet

LeuPheAlaIleValAlaLysAlaValAlaAlaIleValGluThrValArgArgAsnAla

-continued

AlaIleGluGlnGlyPheGluAspGlnProAsnAlaGluIleAsnMetSerAlaLeuTrp

LeuAlaProGluPheIleLeuPheGlyPheAlaGluAlaPheThrProValGlyLeuVal

GluPhePheTyrCysPhePheProLysSerMetSerSerPheAlaMetAlaMetPheThr

LeuGlyLeuAlaCysSerAspValValSerGlyValLeuValSerIleValAspThrVal

ThrSerIleGlyGlyAsnGluSerTrpLeuSerThrAsnIleAsnArgGlyHisLeuAsn

TyrTyrTyrGlyLeuLeuThrPheLeuGlyIleLeuAsnTyrPheTyrTyrLeuValIle

CysTrpAlaTyrGlyProIleGlnGlyGluLysHisGluAspSerAlaArgLysLysAsp

AspLysPheGlyTyrArgGluLeuProThrSer

The nip-1 allele of MtNIP refers to a mutant *M. truncatula* nip-1 mutant gene sequence (mutation in bold italics). *Medicago truncatula* nip-1 cDNA has the following (SEQ ID No.3):

ATGGAGTACACAAACAGTGATGATGCTACAAATGAAAAACTCATTGAAAATGGCAGCTCTTCATCATCTT

CTCAACCCAGAAAGGGTGGTTTAAGAACCATGCCCTTTATCATAGTGAATGAGTGTCTTGAGAAAGTGGC

AAGTTATGGAATAATGCCAAACATGATATTATACTTGAGGGATGATTATAACATGCCTATTGCTAAGGCT

AGTTATGTTCTTTCTACTTGGTCTGCTATGTCCAATGTTTTGTCCATCTTTGGTGCTTTTCTCTCTGATT

CTTACTTGGGTCGCTTCAATGTCATCACTATTGGCTCCTTTTCTAGCCTTCTTGGTTTAACCGTTTTGTG

GTTAACTGCCATGATCCCGGTGCTAAAACCTACCTGTGCATCACTCTTTGAAATCTGTAATTCTGCTACT

TCATCCCAACAAGCAGTTCTGTTCCTTTCCTTAGGATTAATTTCAATTGGAGCTGGTTGTGTTAGACCTT

GTTCCATAGCCTTTGGAGCAGAGCAATTGACTATTAAGGGAAATTCTGGTGATGGGAATGGCAGGATCTT

GGATAGTTACTTTAATTGGTATTATACCTCAATTTCAGTTTCAACCATTATCGCGTTGAGTGTGATTGCT

TACATTCAAGAAAACCTTGGATGGAAAATTGGGTTTGGAGTACCTGCTGTGCTAATGCTCGTATCGGTCA

TCAGTTTCATTATTGGTTCACCGTTATATGTCAAAGTGAAGCCAAGTGAAAGCTTACTCACTAATTTTGC

AAGAGTAGTTGTGGTGGCAACCAAGAACAGAAAACTTAGTCTTCCTGATCACGACTCTGATCGTTACTGT

CAAGGTCATGATTCAAAGCTGAAGGTTCCTACCGATAGCCTTAGGTTTTTGAACAAAGCTTGCGTAATAA

GAAATCCTGAGACAGATCTTAATCGAGATGGGTCAATTTCAAATCCGTGGAACCTATGCACAATAGAACA

GGTGGAGTCACTGAAGTCTTTGCTCAGAGTCATTCCTATGTGGTCAACGGGAATCTTTATGATGGCGACT

CAGAGTTCATTTTCTACTCTTCAAGCCAAAACTTTGAACCGAACGTTATTCGGCAATTTCAATTTTCCTG

CAGGATCGTTCAATCTTATCTTGATATTCACCTTAACAATAGTAATTCCTTTATATGACCGTGTAGGAGT

ACCTCTACTAGCTAAATACGCAGGCCGGCCTAGAGGATTCAGTTTTAAAGTCCGCATCGGGATAGGAATG

CTGTTTGCAATTGTAGCTAAAGCAGTAGCAGCTATTGTTGAAACGGTGAGACGAAATGCAGCGATTGAAC

AAGGGTTTGAGGACCAACCTAATGCTGAAATTAACATGTCGGCTTTATGGCTTGCTCCAGAGTTTATTTT

GTTTGGATTCGCCGAAGCTTTCACACCAGTTGGACTGGTTGAGTTTTTCTACTGTTTTTTCCCTAAGAGT

ATGTCTAGTTTTGCAATGG*T*TATGTTCACATTGGGACTAGCTTGTTCTGACGTAGTTTCAGGTGTGCTTG

TGAGCATTGTGGACACGGTCACTAGTATTGGAGGGAATGAGAGCTGGTTATCGACTAACATCAATAGGGG

ACATTTGAATTACTACTACGGGCTACTCACTTTCTTAGGCATTCTTAACTACTTCTATTATCTTGTTATT

TGTTGGGCTTATGGACCCATACAGGGAGAGAAACATGAAGATTCGGCCAGAAAGAAAGACGATAAATTTG

GTTACAGGGAGTTGCCTACTTCATAG

*Medicago truncatula* nip-1 Amino acid Sequence (SEQ ID No.: 4)

MetGluTyrThrAsnSerAspAspAlaThrAsnGluLysLeuIleGluAsnGlySerSer

SerSerSerSerGlnProArgLysGlyGlyLeuArgThrMetProPheIleIleValAsn

GluCysLeuGluLysValAlaSerTyrGlyIleMetProAsnMetIleLeuTyrLeuArg

AspAspTyrAsnMetProIleAlaLysAlaSerTyrValLeuSerThrTrpSerAlaMet

SerAsnValLeuSerIlePheGlyAlaPheLeuSerAspSerTyrLeuGlyArgPheAsn

ValIleThrIleGlySerPheSerSerLeuLeuGlyLeuThrValLeuTrpLeuThrAla

MetIleProValLeuLysProThrCysAlaSerLeuPheGluIleCysAsnSerAlaThr

SerSerGlnGlnAlaValLeuPheLeuSerLeuGlyLeuIleSerIleGlyAlaGlyCys

ValArgProCysSerIleAlaPheGlyAlaGluGlnLeuThrIleLysGlyAsnSerGly

AspGlyAsnGlyArgIleLeuAspSerTyrPheAsnTrpTyrTyrThrSerIleSerVal

SerThrIleIleAlaLeuSerValIleAlaTyrIleGlnGluAsnLeuGlyTrpLysIle

GlyPheGlyValProAlaValLeuMetLeuValSerValIleSerPheIleIleGlySer

ProLeuTyrValLysValLysProSerGluSerLeuLeuThrAsnPheAlaArgValVal

ValValAlaThrLysAsnArgLysLeuSerLeuProAspHisAspSerAspArgTyrCys

GlnGlyHisAspSerLysLeuLysValProThrAspSerLeuArgPheLeuAsnLysAla

CysValIleArgAsnProGluThrAspLeuAsnArgAspGlySerIleSerAsnProTrp

AsnLeuCysThrIleGluGlnValGluSerLeuLysSerLeuLeuArgValIleProMet

TrpSerThrGlyIlePheMetMetAlaThrGlnSerSerPheSerThrLeuGlnAlaLys

ThrLeuAsnArgThrLeuPheGlyAsnPheAsnPheProAlaGlySerPheAsnLeuIle

LeuIlePheThrLeuThrIleValIleProLeuTyrAspArgValGlyValProLeuLeu

AlaLysTyrAlaGlyArgProArgGlyPheSerPheLysValArgIleGlyIleGlyMet

LeuPheAlaIleValAlaLysAlaValAlaAlaIleValGluThrValArgArgAsnAla

AlaIleGluGlnGlyPheGluAspGlnProAsnAlaGluIleAsnMetSerAlaLeuTrp

LeuAlaProGluPheIleLeuPheGlyPheAlaGluAlaPheThrProValGlyLeuVal

GluPhePheTyrCysPhePheProLysSerMetSerSerPheAlaMetValMetPheThr

LeuGlyLeuAlaCysSerAspValValSerGlyValLeuValSerIleValAspThrVal

ThrSerIleGlyGlyAsnGluSerTrpLeuSerThrAsnIleAsnArgGlyHisLeuAsn

TyrTyrTyrGlyLeuLeuThrPheLeuGlyIleLeuAsnTyrPheTyrTyrLeuValIle

CysTrpAlaTyrGlyProIleGlnGlyGluLysHisGluAspSerAlaArgLysLysAsp

AspLysPheGlyTyrArgGluLeuProThrSer

The laid (nip-2) allele of MtNIP refers to a *M. truncatula* laid (nip-2) mutant gene sequence (mutation in bold italics) cDNA (Seq ID No.: 5):

ATGGAGTACACAAACAGTGATGATGCTACAAATGAAAAACTCATTGAAAATGGCAGCTCTTCATCATCTT

CTCAACCCAGAAAGGGTGGTTTAAGAACCATGCCCTTTATCATAGTGAATGAGTGTCTTGAGAAAGTGGC

AAGTTATGGAATAATGCCAAACATGATATTATACTTGAGGGATGATTATAACATGCCTATTGCTAAGGCT

AGTTATGTTCTTTCTACTTGGTCTGCTATGTCCAATGTTTTGTCCATCTTTGGTGCTTTTCTCTCTGATT

CTTACTTGGGTCGCTTCAATGTCATCACTATTGGCTCCTTTTCTAGCCTTCTTGGTTTAACCGTTTTGTG

GTTAACTGCCATGATCCCGGTGCTAAAACCTACCTGTGCATCACTCTTTGAAATCTGTAATTCTGCTACT

-continued

TCATCCCAACAAGCAGTTCTGTTCCTTTCCTTAGGATTAATTTCAATTGGAGCTGGTTGTGTTAGACCTT

GTTCCATAGCCTTTGGAGCAGAGCAATTGACTATTAAGGGAAATTCTGGTGATGGGAATGGCAGGATCTT

GGATAGTTACTTTAATTGGTATTATACCTCAATTTCAGTTTCAACCATTATCGCGTTGAGTGTGATTGCT

TACATTCAAGAAAACCTTGGATGGAAAATTGGGTTTGGAGTACCTGCTGTGCTAATGCTCGTATCGGTCA

TCAGTTTCATTATTGGTTCACCGTTATATGTCAAAGTGAAGCCAAGTGAAAGCTTACTCACTAATTTTGC

AAGAGTAGTTGTGGTGGCAACCAAGAACAGAAAACTTAGTCTTCCTGATCACGACTCTGATCGTTACTGT

CAAGGTCATGATTCAAAGCTGAAGGTTCCTACCGATAGCCTTAGGTTTTTGAACAAAGCTTGCGTAATAA

GAAATCCTGAGACAGATCTTAATCGAGATGGGTCAATTTCAAATCCGTGGAACCTATGCACAATAGAACA

GGTGGAGTCACTGAAGTCTTTGCTCAGAGTCATTCCTATGTGATCAACGGGAATCTTTATGATGGCGACT

CAGAGTTCATTTTCTACTCTTCAAGCCAAAACTTTGAACCGAACGTTATTCGGCAATTTCAATTTTCCTG

CAGGATCGTTCAATCTTATCTTGATATTCACCTTAACAATAGTAATTCCTTTATATGACCGTGTAGGAGT

ACCTCTACTAGCTAAATACGCAGGCCGGCCTAGAGGATTCAGTTTTAAAGTCCGCATCGGGATAGGAATG

CTGTTTGCAATTGTAGCTAAAGCAGTAGCAGCTATTGTTGAAACGGTGAGACGAAATGCAGCGATTGAAC

AAGGGTTTGAGGACCAACCTAATGCTGAAATTAACATGTCGGCTTTATGGCTTGCTCCAGAGTTTATTTT

GTTTGGATTCGCCGAAGCTTTCACACCAGTTGGACTGGTTGAGTTTTTCTACTGTTTTTTCCCTAAGAGT

ATGTCTAGTTTTGCAATGGCTATGTTCACATTGGGACTAGCTTGTTCTGACGTAGTTTCAGGTGTGCTTG

TGAGCATTGTGGACACGGTCACTAGTATTGGAGGGAATGAGAGCTGGTTATCGACTAACATCAATAGGGG

ACATTTGAATTACTACTACGGGCTACTCACTTTCTTAGGCATTCTTAACTACTTCTATTATCTTGTTATT

TGTTGGGCTTATGGACCCATACAGGGAGAGAAACATGAAGATTCGGCCAGAAAGAAAGACGATAAATTTG

GTTACAGGGAGTTGCCTACTTCATAG

The translated amino acid sequence for *M. truncatula* latd (nip-2) mutant gene sequence leads to a stop codon as indicated below (SEQ ID NO.: 6):

MetGluTyrThrAsnSerAspAspAlaThrAsnGluLysLeuIleGluAsnGlySerSer

SerSerSerSerGlnProArgLysGlyGlyLeuArgThrMetProPheIleIleValAsn

GluCysLeuGluLysValAlaSerTyrGlyIleMetProAsnMetIleLeuTyrLeuArg

AspAspTyrAsnMetProIleAlaLysAlaSerTyrValLeuSerThrTrpSerAlaMet

SerAsnValLeuSerIlePheGlyAlaPheLeuSerAspSerTyrLeuGlyArgPheAsn

ValIleThrIleGlySerPheSerSerLeuLeuGlyLeuThrValLeuTrpLeuThrAla

MetIleProValLeuLysProThrCysAlaSerLeuPheGluIleCysAsnSerAlaThr

SerSerGlnGlnAlaValLeuPheLeuSerLeuGlyLeuIleSerIleGlyAlaGlyCys

ValArgProCysSerIleAlaPheGlyAlaGluGlnLeuThrIleLysGlyAsnSerGly

AspGlyAsnGlyArgIleLeuAspSerTyrPheAsnTrpTyrTyrThrSerIleSerVal

SerThrIleIleAlaLeuSerValIleAlaTyrIleGlnGluAshLeuClyTrpLysIle

GlyPheGlyValProAlaValLeuMetLeuValSerValIleSerPheIleIleGlySer

ProLeuTyrValLysValLysProSerGluSerLeuLeuThrAsnPheAlaArgValVal

ValValAlaThrLysAsnArgLysLeuSerLeuProAspHisAspSerAspArgTyrCys

GlnGlyHisAspSerLysLeuLysValProThrAspSerLeuArgPheLeuAsnLysAla

CysValIleArgAsnProGluThrAspLeuAsnArgAspGlySerIleSerAsnProTrp

AsnLeuCysThrIleGluGlnValGluSerLeuLysSerLeuLeuArgValIleProMet

The nip-3 allele of MtNIP refers to a mutant having the following sequence:

*M. truncatula* nip-3 mutant gene sequence (mutation highlighted):

*Medicago truncatula* nip-3 Cdna (SEQ ID No.: 7)

```
ATGGAGTACACAAACAGTGATGATGCTACAAATGAAAAACTCATTGAAAATGGCAGCTCTTCATCATCTT
CTCAACCCAGAAAGGGTGGTTTAAGAACCATGCCCTTTATCATAGTGAATGAGTGTCTTGAGAAAGTGGC
AAGTTATGGAATAATGCCAAACATGATATTATACTTGAGGGATGATTATAACATGCCTATTGCTAAGGCT
AGTTATGTTCTTTCTACTTGGTCTGCTATGTCCAATGTTTTGTCCATCTTTGGTGCTTTTCTCTCTGATT
CTTACTTGGGTCGCTTCAATGTCATCACTATTGGCTCCTTTTCTAGCCTTCTTGGTTTAACCGTTTTGTG
GTTAACTGCCATGATCCCGGTGCTAAAACCTACCTGTGCATCACTCTTTGAAATCTGTAATTCTGCTACT
TCATCCCAACAAGCAGTTCTGTTCCTTTCCTTAGGATTAATTTCAATTGGAGCTGGTTGTGTTAGACCTT
GTTCCATAGCCTTTGGAGCAAAGCAATTGACTATTAAGGGAAATTCTGGTGATGGGAATGGCAGGATCTT
CGATAGTTACTTTAATTGGTATTATACCTCAATTTCAGTTTCAACCATTATCGCGTTGAGTGTGATTGCT
TACATTCAAGAAAACCTTGGATGGAAAATTGGGTTTGGAGTACCTGCTGTGCTAATGCTCGTATCGGTCA
TCAGTTTCATTATTGGTTCACCGTTATATGTCAAAGTGAAGCCAAGTGAAAGCTTACTCACTAATTTTGC
AAGAGTAGTTGTGGTGGCAACCAAGAACAGAAAACTTAGTCTTCCTGATCACGACTCTGATCGTTACTGT
CAAGGTCATGATTCAAAGCTGAAGGTTCCTACCGATAGCCTTAGGTTTTTGAACAAAGCTTGCGTAATAA
GAAATCCTGAGACAGATCTTAATCGAGATGGGTCAATTTCAAATCCGTGGAACCTATGCACAATAGAACA
GGTGGAGTCACTGAAGTCTTTGCTCAGAGTCATTCCTATGTGGTCAACGGGAATCTTTATGATGGCGACT
CAGAGTTCATTTTCTACTCTTCAAGCCAAAACTTTGAACCGAACGTTATTCGGCAATTTCAATTTTCCTG
CAGGATCGTTCAATCTTATCTTGATATTCACCTTAACAATAGTAATTCCTTTATATGACCGTGTAGGAGT
ACCTCTACTAGCTAAATACGCAGGCCGGCCTAGAGGATTCAGTTTTAAAGTCCGCATCGGGATAGGAATG
CTGTTTGCAATTGTAGCTAAAGCAGTAGCAGCTATTGTTGAAACGGTGAGACGAAATGCAGCGATTGAAC
AAGGGTTTGAGGACCAACCTAATGCTGAAATTAACATGTCGGCTTTATGGCTTGCTCCAGAGTTTATTTT
GTTTGGATTCGCCGAAGCTTTCACACCAGTTGGACTGGTTGAGTTTTTCTACTGTTTTTTCCCTAAGAGT
ATGTCTAGTTTTGCAATGGCTATGTTCACATTGGGACTAGCTTGTTCTGACGTAGTTTCAGGTGTGCTTG
TGAGCATTGTGGACACGGTCACTAGTATTGGAGGGAATGAGAGCTGGTTATCGACTAACATCAATAGGGG
ACATTTGAATTACTACTACGGGCTACTCACTTTCTTAGGCATTCTTAACTACTTCTATTATCTTGTTATT
TGTTGGGCTTATGGACCCATACAGGGAGAGAAACATGAAGATTCGGCCAGAAAGAAAGACGATAAATTTG
GTTACAGGGAGTTGCCTACTTCATAG
```

*Medicago truncatula* nip-3 amino acid (SEQ ID No.: 8)

```
MetGluTyrThrAsnSerAspAspAlaThrAsnGluLysLeuIleGluAsnGlySerSer
SerSerSerSerGlnProArgLysGlyGlyLeuArgThrMetProPheIleIleValAsn
GluCysLeuGluLysValAlaSerTyrGlyIleMetProAsnMetIleLeuTyrLeuArg
AspAspTyrAsnMetProIleAlaLysAlaSerTyrValLeuSerThrTrpSerAlaMet
SerAsnValLeuSerIlePheGlyAlaPheLeuSerAspSerTyrLeuGlyArgPheAsn
ValIleThrIleGlySerPheSerSerLeuLeuGlyLeuThrValLeuTrpLeuThrAla
MetIleProValLeuLysProThrCysAlaSerLeuPheGluIleCysAsnSerAlaThr
SerSerGlnGLnAlaValLeuPheLeuSerLeuGlyLeuIleSerIleGlyAlaGlyCys
ValArgProCysSerIleAlaPheGlyAlaLysGlnLeuThrIleLysGlyAsnSerGly
```

-continued

AspGlyAsnGlyArgIleLeuAspSerTyrPheAsnTrpTyrTyrThrSerIleSerVal

SerThrIleIleAlaLeuSerValIleAlaTyrIleGLnGluAsnLeuGlyTrpLysIle

GlyPheGlyValProAlaValLeuMetLeuValSerValIleSerPheIleIleGlySer

ProLeuTyrValLysValLysProSerGluSerLeuLeuThrAsnPheAlaArgValVal

ValValAlaThrLysAsnArgLysLeuSerLeuProAspHisAspSerAspArgTyrCys

GlnGlyHisAspSerLysLeuLysValProThrAspSerLeuArgPheLeuAsnLysAla

CysValIleArgAsnProGluThrAspLeuAsnArgAspGlySerIleSerAsnProTrp

AsnLeuCysThrIleGluGlnValGluSerLeuLysSerLeuLeuArgValIleProMet

TrpSerThrGlyIlePheMetMetAlaThrGlnSerSerPheSerThrLeuGlnAlaLys

ThrLeuAsnArgThrLeuPheGlyAsnPheAsnPheProAlaGlySerPheAsnLeuIle

LeuIlePheThrLeuThrIleValIleProLeuTyrAspArgValGlyValProLeuLeu

AlaLysTyrAlaGlyArgProArgGlyPheSerPheLysValArgIleGlyIleGlyMet

LeuPheAlaIleValAlaLysAlaValAlaAlaIleValGluThrValArgArgAsnAla

AlaIleGluGlnGlyPheGluAspGlnProAsnAlaGluIleAsnMetSerAlaLeuTrp

LeuAlaProGluPheIleLeuPheGlyPheAlaGluAlaPheThrProValGlyLeuVal

GluPhePheTyrCysPhePheProLysSerMetSerSerPheAlaMetAlaMetPheThr

LeuGlyLeuAlaCysSerAspValValSerGlyValLeuValSerIleValAspThrVal

ThrSerIleGlyGlyAsnGluSerTrpLeuSerThrAsnIleAsnArgGlyHisLeuAsn

TyrTyrTyrGlyLeuLeuThrPheLeuGlyIleLeuAsnTyrPheTyrTyrLeuValIle

CysTrpAlaTyrGlyProIleGlnGlyGluLysHisGluAspSerAlaArgLysLysAsp

AspLysPheGlyTyrArgGluLeuProThrSer

In one embodiment of the present invention, the MtNIP gene is expressed in a plant to cause a significant increase in biomass. In certain embodiments, the MtNIP gene is the *Medicago truncatula* (*Medicago*) MtNIP gene, and the plant is a *Arabidopsis thaliana*, a *Medicago Truncatula* or a tobacco plant.

In certain embodiments of the invention, the MtNIP gene is expressed in a plant to cause the plant to be larger than a wild-type plant. In certain embodiments, the MtNIP gene is the *Medicago truncatula* (*Medicago*) MtNIP gene, and the plant is *Arabidopsis thaliana, Medicago Truncatula* or a tobacco plant.

In certain embodiments, the expression of the MtNIP gene in plants causes them to flower earlier than wild-type plants.

In certain embodiments of the invention, other genes in the NRT1/PTR family may be over-expressed in plants to result in increased biomass, plant growth, and early flowering. The gene may be one of the 53 members of the NRT1/PTR family in *Arabidopsis* or the 80 members in rice, of which only a subset investigated (Tsay et al., 2007).

In certain embodiments, the plant may be a member of the *Brassica* family, such as oilseed rape, canola, cabbage, cauliflower, broccoli, Brussels sprout. Chinese cabbage, bak choi, turnip, or mustard or other plants.

Example 1

*Xenopus oocytes* Expressing MtNIP Transport Nitrate in a pH-Dependent Manner

Figure 3:
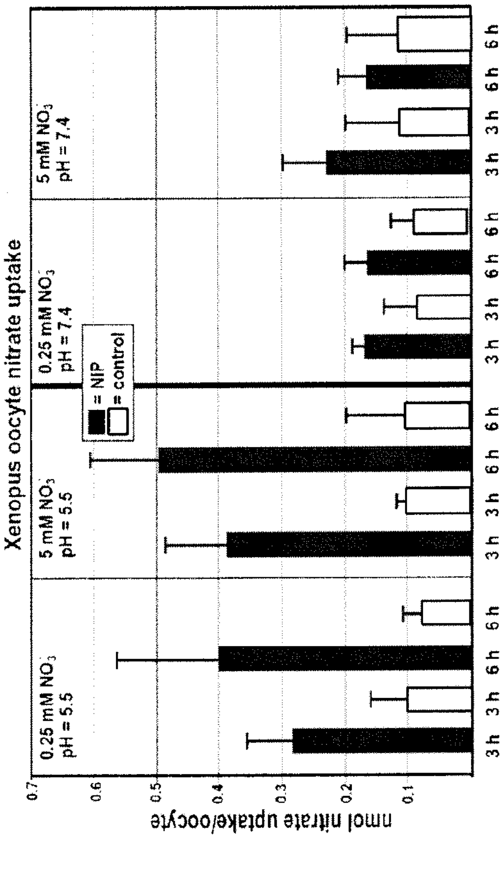
FIG. 3 shows nitrate uptake in *Xenopus* oocytes expressing MtNIP. *Xenopus* oocytes were microinjected with MtNIP mRNA or water as a negative control, incubated for 3 days, then incubated for the indicated times in media containing 0.25 mM (250 μM) or 5 mM nitrate at the indicated pH. The oocytes were lysed and nitrate was determined using a spectrophotometric assay (Cayman Chemical, Ann Arbor, Mich.). The results show that MtNIP-expressing oocytes take up nitrate at low concentrations, in a pH-dependent manner, consistent with MtNIP being a high-affinity, proton-coupled nitrate transporter.

*Xenopus oocytes* that were microinjected with in vitro transcribed MtNIP RNA, or water as a control, were incubated with 250 μM or 5 mM nitrate at pH 5.5 or pH 7.4 (FIG. 3). At the end of incubation, the oocytes were rinsed, lysed and assayed for nitrate uptake using a spectrophotometric assay (Cayman Chemical, Ann Arbor, Mich.). At pH 5.5, MtNIP-expressing oocytes were able to take up significant nitrate provided at 250 μM nitrate almost as well as at 5 mM nitrate, while the water-injected control oocytes were not.

Example 2

NIP-3 Mutant Protein Can Transport Nitrate in *Xenopus oocytes*, and NIP-1 and LATD (NIP-2) Mutant Proteins Cannot Transport Nitrate in *Xenopus oocytes*

Figure 4:
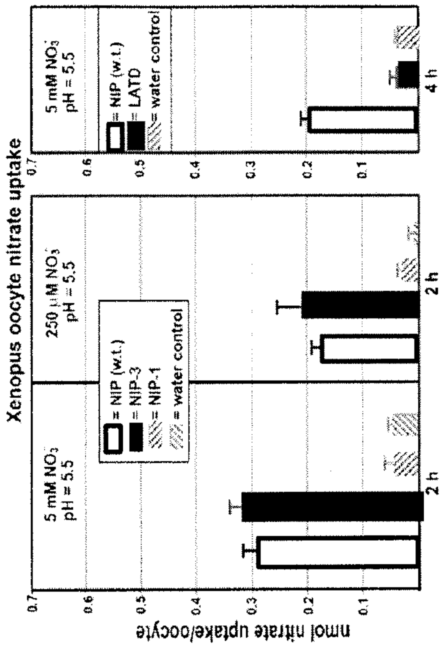
FIG. 4 shows nitrate uptake in *Xenopus* oocytes expressing MtNIP or mutant NIP mRNAs. *Xenopus* oocytes were microinjected with MtNIP mRNA, mutant MtNIP mRNA or water as a negative control, incubated for 3 days, then incubated for the indicated times in media containing 0.25 mM or 5 mM nitrate, at pH 5.5, as in FIG. 2. Nitrate was assayed as in FIG. 2. The results show that while neither nip-1 nor nip-2 (latd) mutant proteins are capable of transporting nitrate, the nip-3 mutant protein transports nitrate as well as wild-type NIP. Since the nip-3 mutant has a nodulation and lateral root phenotype, NIP protein has another function besides nitrate transport.

The latd (nip-2) allele is null mutation, with a nonsense mutation in the middle of the MtNIP gene; in contrast, both the nip-1 and nip-3 alleles have mis-sense mutations (Yendrek et al., 2010). *Xenopus oocytes* were microinjected with in vitro transcribed nip-1, latd (nip-2), or nip-3 RNA, or water as a control, incubated with 250 μM or 5 mM nitrate at pH 5.5, rinsed, lysed and assayed for nitrate uptake (FIG. 4). The results show that nip-1 and latd (nip-2) proteins cannot transport nitrate, but nip-3 protein and wild-type MtNIP protein can nip-3 mutants have root architecture and nodulation defects (Teillet et al., 2008). Thus, MtNIP protein has another function besides nitrate transport.

Example 3

*Arabidopsis* chl1-5 Mutants are Restored to Chlorate Sensitivity by MtNIP

Figure 5:
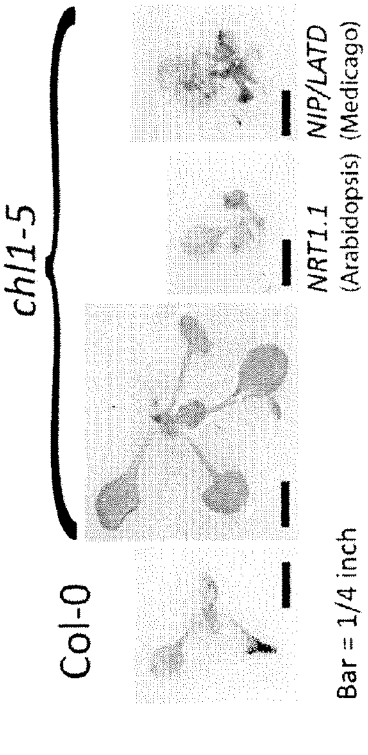
FIG. 5 shows that MtNIP complements the *Arabidopsis* chl1-5 mutant for chlorate sensitivity. *Arabidodpsis* chl1-5 plants were transformed with a construct containing MtNIP cDNA under the control of the *Arabidopsis* EF1 α promoter, pAtEF1 α-MtNIP or a positive control construct containing the *Arabidopsis* AtNRT1.1 gene under the same promoter, pAtEF1 α-AtNRT1.1. The plants were treated with chlorate as described in Tsay et al. 1993. The MtNIP gene was able to confer chlorate sensitivity on chl1-5 plants, similar to the AtNRT1.1 gene.

MtNIP was over-expressed in *Arabidopsis* chl1-5 mutants that contain a well-characterized deletion in the NRT1(CHL) dual affinity nitrate transporter gene, using the *Arabidopsis* EF1 αpromoter (Auriac and Timmers, 2007). The mutant is chlorate resistant (Tsay et al., 1993; Huang et al., 1996; Wang et al., 1998). The herbicide chlorate is a nitrate analog that is taken up via the CHL 1(NRT 1.1) nitrate transporter and reduced to toxic chlorite by nitrate reductase. chl1-5 mutants containing the pAtEF1 α-MtNIP construct are restored to chlorate sensitivity, similar to chl1-5 mutants containing a control pAtEF1 α-AtNRT1. 1(CHL) construct (FIG. 5). This demonstrates a role for MtNIP in the transport of chlorate via a nitrate transporter route.

Example 4

Figure 6:
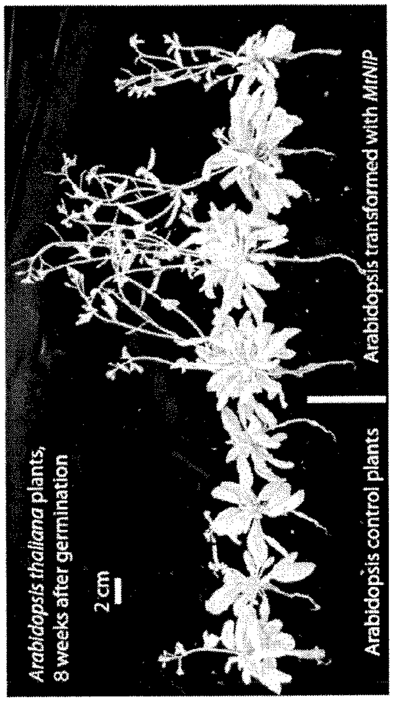
FIG. 6 shows the phenotype of pAtEF1α-MtNIP expressing plants, with controls. The growth of *Arabidopsis* plants transformed pAtEF1α-MtNIP and control plants not transformed with pAtEF1α-MtNIP at 8 weeks is shown. Plants were grown on Sunshine mix (Sun Gro Horticulture, Bellevue, Wash.) at 22 C on 16 h/8 h light/dark cycle. They were fertilized 3 weeks post-germination with Peter's 20/20/20 (Scotts, Charleston, S.C.). Plants labeled #1 and #2 represent independently transformed lines. It is readily apparent that pAtEF1α-MtNIP expression yields plants with greater biomass that flower earlier than the controls.

Growth Phenotype of *Arabidopsis* Plants Expressing the *M. truncatula* MtNIP Gene The *Arabidopsis* plants transformed with pAtEF1 α-MtNIP were found to have the unexpected phenotype of being much larger than wild-type (FIG. 6, and Table 1). Controls transformed with empty vector showed similar growth to the wild-type (not shown). It is possible that the high affinity nitrate transport function of MtNIP is responsible for the observed growth phenotype. Although not wanting to be bound by theory, since *Xenopus* oocyte expressing the nip-3 mutant version of the gene transport nitrate, which means that MtNIP has a second, still unknown function, it is also possible that this other, still unknown function of MtNIP is responsible for the observed growth phenotype.

TABLE 1

Dry weight of *Arabidopsis* plants at 8 weeks post-germination

| Genotype | Weight (Average +/− standard deviation, grams) | Fold increase, average compared to control |
|---|---|---|
| Not transformed with MtNIP | 1.56 +/− 0.33 | |
| Not transformed with MtNIP | 1.71 +/− 0.45 | |
| Not transformed with MtNIP | 1.93 +/− 0.69 | |
| Not transformed with MtNIP | 1.16 +/− 0.41 | |
| Transformed with MtNIP | 5.00 +/− 1.60 | 3.1 |
| Transformed with MtNIP | 5.87 +/− 1.78 | 3.7 |
| Transformed with MtNIP | 6.99 +/− 1.04 | 4.4 |
| Transformed with MtNIP | 5.57 +/− 1.80 | 3.5 |

No reports were found in the scientific literature describing constitutive expression of an NRT1/PTR family protein to result in an increase in growth or biomass of a plant. Two reports were found, one in the literature and one on a poster, of a rice gene in the NRT2 family causing increases in growth when it is over-expressed in rice. However, the NRT2 family is not related to the NRT1/PTR family—these two gene families are phylogenetically distinct (Tsay et al., 2007).

Example 6

As stated above, the *Medicago truncatula* NIP/LATD gene encodes a protein found in a clade of nitrate transporters within the large NRT1(PTR) family that also encodes transporters of di- and tri-peptides, dicarboxylates, auxin and abscisic acid. Of the NRT1(PTR) members known to transport nitrate, most are low-affinity transporters. This embodiment shows that *Medicago* nip/latd mutants are more defective in their lateral root responses to nitrate provided at low (250 μM) concentrations than at higher (5 mM) concentrations. However nitrate uptake experiments showed no discernible differences in uptake in the mutants. Heterologous expression experiments showed that MtNIP/LATD encodes a nitrate transporter: expression in *Xenopus laevis* oocytes conferred upon the oocytes the ability to take up nitrate from the media with high affinity and expression of MtNIP/LATD in an *Arabidopsis* chl1(nrt1.1) mutant rescued the chlorate susceptibility phenotype. *X. laevis* oocytes expressing mutant Mtnip-1 and Mtlatd were unable to take up nitrate from the media, but oocytes expressing the less severe Mtnip-3 allele were, demonstrating that Mtnip-3 is altered in another activity besides nitrate transport. *Medicago* nip/latd mutants have pleiotropic defects in nodulation and root architecture. Expression of the *Arabidopsis* NRT1.1 gene in mutant Mtnip-1 roots partially rescued Mtnip-1 for root architecture defects, but not for nodulation defects, suggesting the spectrum of activities inherent in AtNRT1.1 is different from those possessed by MtNIP/LATD. Collectively, the data show that MtNIP/LATD is a high affinity nitrate transporter and has a second unknown function which is critical for nodulation.

All plants require nitrogen (N) as an essential nutrient and are able to acquire N from nitrate ($NO_3^-$) and ammonium ($NH_4^+$) in the soil. Nitrate acquisition begins with its transport into root cells, accomplished by $NO_3^-$ transporters. Soil $NO_3^-$ concentrations can vary by five orders of magnitude (Crawford, 1995) and to cope with the variability, plants have evolved both high-affinity (HATS) and low-affinity (LATS) transport systems. These are encoded by two gene families: the phylogenetically distinct NRT1(PTR) and NRT2 families. Members of these families also participate in movement of $NO_3^-$ throughout the plant and within plant cells (Miller et al., 2007; Segonzac et al., 2007; Tsay et al., 2007; Almagro et al., 2008: Lin et al., 2008; Fan et al., 2009; Li et al., 2010; Barbier-Brygoo et al., 2011; Wang and Tsay, 2011; Xu et al., 2012). Proteins in the CLC transporter family also transport $NO_3^-$; these transporters are associated with cytosol to organelle $NO_3^-$ movement (Zifarelli and Pusch, 2010).

NRT1(PTR) is a large family of transporters, comprising 53 members in *Arabidopsis,* 84 members in rice, with NRT1 PTR) members known in several other species (Tsay et al., 2007; Zhao et al., 2010). In addition to transporting $NO_3^-$ coupled to $H^+$ movement, members of the NRT1(PTR) family have been found to transport di- or tripeptides, amino acids (Waterworth and Bray, 2006), dicarboxylic acids (Jeong et al., 2004), auxin (Krouk et al., 2010) and/or abscisic acid (Kanno et al., 2012). Only a small number of NRT1(PTR) proteins have been functionally studied compared to the large number that exist in higher plants, and thus the number of biochemical functions ascribed to this family may expand.

Of the NRT1(PTR) members known to transport $NO_3^-$, most are LATS transporters. An important exception is *Arabidopsis* NRT1.1(CHL1), a dual-affinity transporter, that is the most extensively studied NRT1(PTR) protein. AtNRT1.1 (CHL1) was identified initially on the basis of its ability to confer chlorate toxicity resistance and was the first of this family to be cloned (Doddema et al., 1978; Tsay et al., 1993). AtNRT1.1(CHL1) is an essential component of $NO_3^-$ transport and $NO_3^-$ signaling pathways, with important roles regulating expression of other $NO_3^-$ transporters and root architecture (Remans et al., 2006; Walch-Liu et al., 2006; Walch-Liu and Forde, 2008). Its expression is inducible by $NO_3^-$ (Huang et al., 1996). Reversible phosphorylation is essential to its ability to switch between LATS and HATS activity (Liu and Tsay, 2003). In addition, AtNRT1.1(CHL1) acts as a $NO_3^-$ sensor (Munos et al., 2004; Ho et al., 2009; Wang et al., 2009) and has been shown to transport auxin in a $NO_3^-$ concentration dependent manner (Krouk et al., 2010). It has been suggested that AtNRT1.1's ability to transport auxin may be part of its $NO_3^-$ sensing mechanism (Krouk et al., 2010; Krouk et al., 2010; Gojon et al., 2011).

Most legumes and actinorhizal plants have the additional ability to form symbiotic N-fixing root nodules with soil bacteria, enabling them to thrive in $NO_3^-$ and $NH_4^+$ depleted environments. Legume nodulation commences with signal exchange between the plant and rhizobia, followed by root cortical cell divisions, invasion of the root at the site of the cell divisions by rhizobia inside plant-derived infection threads ("Its"), and subsequent endocytosis of rhizobia into newly-divided plant host cells, forming symbiosomes. Within symbiosomes, the rhizobia differentiate into bacteroids that are capable of N fixation (Oldroyd and Downie, 2008; Kouchi et al., 2010). Before N fixation begins, nodules are a sink for the plant's N; N is required to support nodule organogenesis and rhizobial proliferation and differentiation in nodules (Udvardi and Day, 1997). After N fixation begins, nodules are a source of bioavailable N and are a large carbon sink because of the energetic needs of the rhizobia that fix N (White et al., 2007).

NRT1(PTR) transporters have received less attention in legumes and actinorhizal plants than in other plants, but are beginning to be investigated. Several soybean (*Glycine max*) NRT1(PTR) transporter cDNAs have been cloned and their transcription patterns studied. These were predicted to transport $NO_3^-$, but have not been functionally characterized (Yokoyama et al., 2001). Benedito et al. (2010) recognized 111 non-redundant *Medicago truncatula* sequences corresponding to genes in the 2.A.17 transporter class, containing NRT1(PTR) genes (Benedito et al., 2010). The recent availability of three sequenced legume genomes will add to our knowledge of this important gene family (Sato et al., 2008; Schmutz et al., 2010; Young et al., 2011). In faba bean (*Vicia faba*), two NRT1(PTR) transporters have been studied; one was demonstrated to transport di-peptides in yeast, while the second was found to be phylogenetically close to a soybean NRT1(PTR) (Miranda et al., 2003). In alder (*Alnus glutinosa*) nodules, NRT1(PTR) transporter AgDCAT localizes to the symbiotic interface and transports dicarboxylic acid from the cytosol towards its symbiotic partner, *Frankia* (Jeong et al., 2004). The *Medicago* MtNRT1.3 transporter was shown to be a dual-affinity $NO_3^-$ transporter; MtNRT1.3 is up-regulated by the absence of $NO_3^-$ (Morere-Le Paven et al., 2011).

The *Medicago* NIP/LATD gene encodes a predicted NRT1 (PTR) transporter (Harris and Dickstein, 2010; Yendrek et al., 2010) and the three known nip and laid mutants have pleiotropic defects in nodulation and root architecture. Mtnip-1, containing a missense (A497V) mutation in one of the NIP/LATD protein's transmembrane domains, is well characterized with respect to nodulation phenotypes (Veereshlingam et al., 2004). Mtnip-1 develops nodules that initiate rhizobial invasion but fail to release rhizobia from infection threads. Its nodules lack meristems and accumulate polyphenolics, a sign of host defense. Mtnip-1 plants also have defective root architecture (Veereshlingam et al., 2004). The Mtlatd mutant has the most severe phenotype, caused by a stop codon (W341STOP) in the middle of the NIP/LATD putative protein (Yendrek et al., 2010). Mtlatd has serious defects in root architecture with a non-persistent primary root meristem, lateral roots ("LRs") that fail to make the transition from LR primordia to LRs containing a meristem, and defects in root hairs. Mtlatd also has defective nodules (Bright et al., 2005). The missense Mtnip-3 mutant (E171K) is the least affected, forming invaded nodules with meristems and polyphenol accumulation. Mtnip-3 has near-normal root architecture (Teillet et al., 2008; Yendrek et al., 2010).

Here, function of the MtNIP/LATD protein is investigated. We find that MtNIP/LATD is a high-affinity $NO_3^-$ transporter and provide evidence that it has at least one additional biochemical function relevant for root nodule formation and root architecture development.

Mtnip Mutants' Nitrate Phenotypes.

Because of MtNIP/LATD's similarity to low affinity $NO_3^-$ transporters in the NRT1(PTR) family, one hypothesis is that it may be a low affinity $NO_3^-$ transporter (Yendrek et al., 2010). Bioavailable N is known to suppress nodulation and to inhibit N fixation in mature N-fixing nodules (Streeter, 1988; Fei and Vessey, 2008). It is also possible that Mtnip/latd mutants would develop functional root nodules in conditions of $NO_3^-$ sufficiency. To test whether Mtnip-1 was altered in suppression of nodulation by bioavailable N, Mtnip-1 mutant plants were cultivated in 1 mM and 10 mM $KNO_3$ and also in 5 mM $NH_4NO_3$ in the presence of *S. meliloti*. As shown in Table 1, Mtnip-1 formed low numbers of nodules under these conditions compared to no N conditions, similar to wild-type (A17), suggesting normal suppression by bioavailable N sources. The few nodules that formed in Mtnip-1 in 1 mM $KNO_3$, 10 mM $KNO_3$ or 5 mM $NO_3NH_4$ had an Mtnip-1 nodule phenotype.

Figure 7:
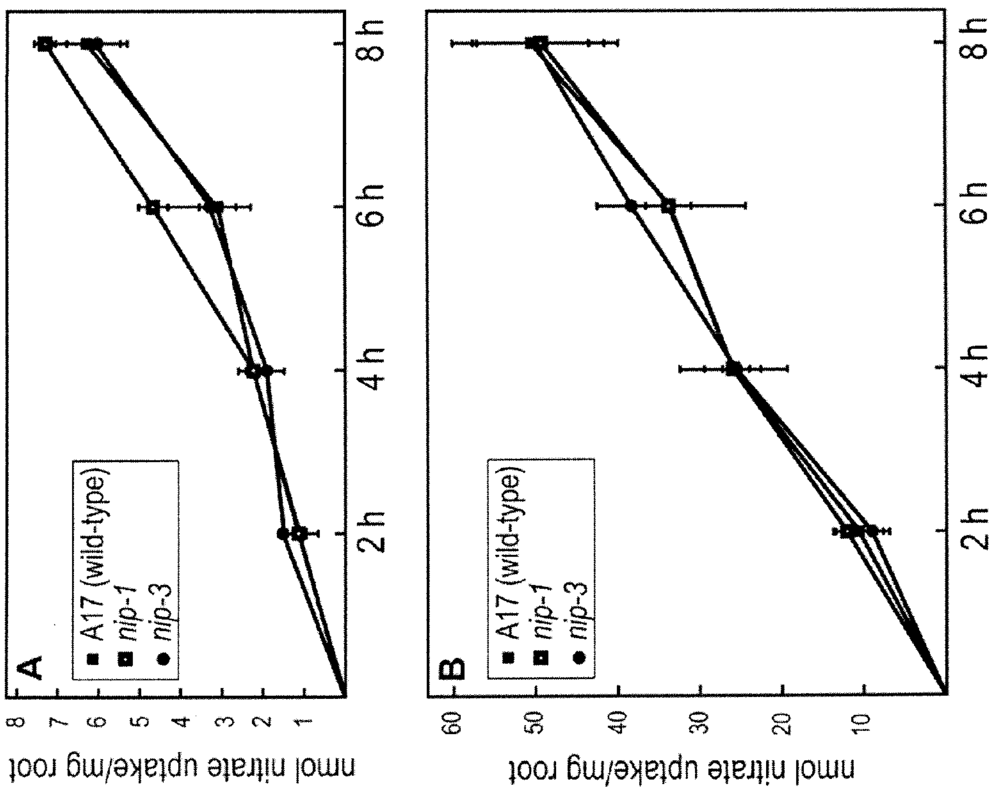
FIG. 7 shows Nitrate uptake in *Medicago*. Wild-type A17, Mtnip-1 and Mtnip-3 plants were placed in solutions containing 250 μM (panel A) or 5 mM (panel B) nitrate. Nitrate uptake was monitored by its uptake from the media at 2 hr intervals. Data are plotted for one biological replicate plus or minus the standard error of the mean.
Figure 8:
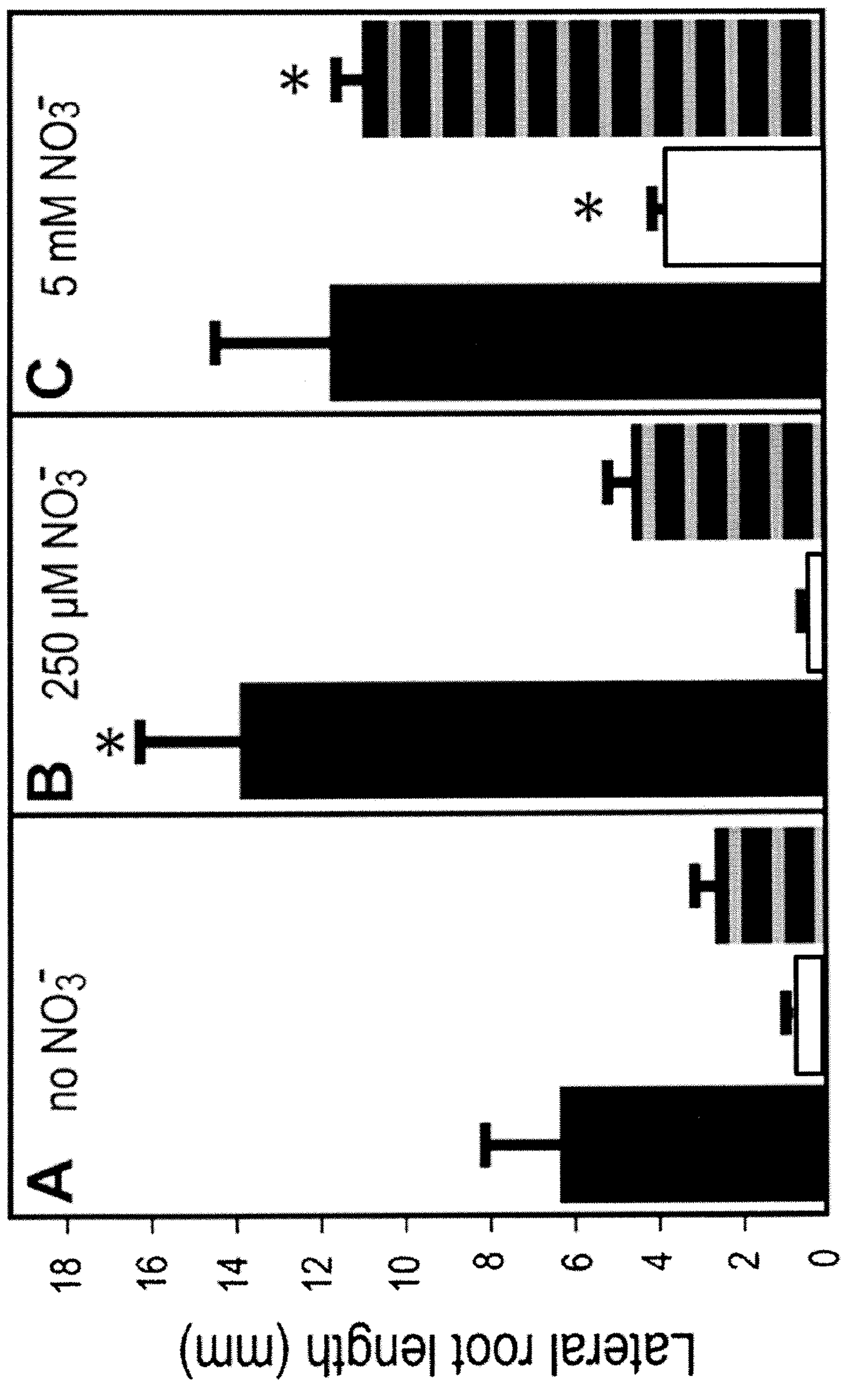
FIG. 8 shows Lateral root lengths of *Medicago* plants grown in different conditions. Wild-type A17 (solid bars), Mtnip-1 (white bars) and Mtnip-3 (horizontally striped bars) were grown in liquid BNM media with no added $NO_3^-$ (panel A), with 250 μM $KNO_3$ (panel B) or with 5 mM $KNO_3$ (panel C), with the media changed every other day. Lateral root lengths were measured after 2 weeks. Data are shown for one biological replicate plus or minus the standard error of the mean, n=5. Replicates gave similar results. Asterisks mark lateral root lengths from plants grown at 250 μM $KNO_3$ and 5 mM $KNO_3$ that are significantly different from the same genotype grown at 0 mM $KNO_3$, using Student's t-test at $p<0.05$.
Figure 9:
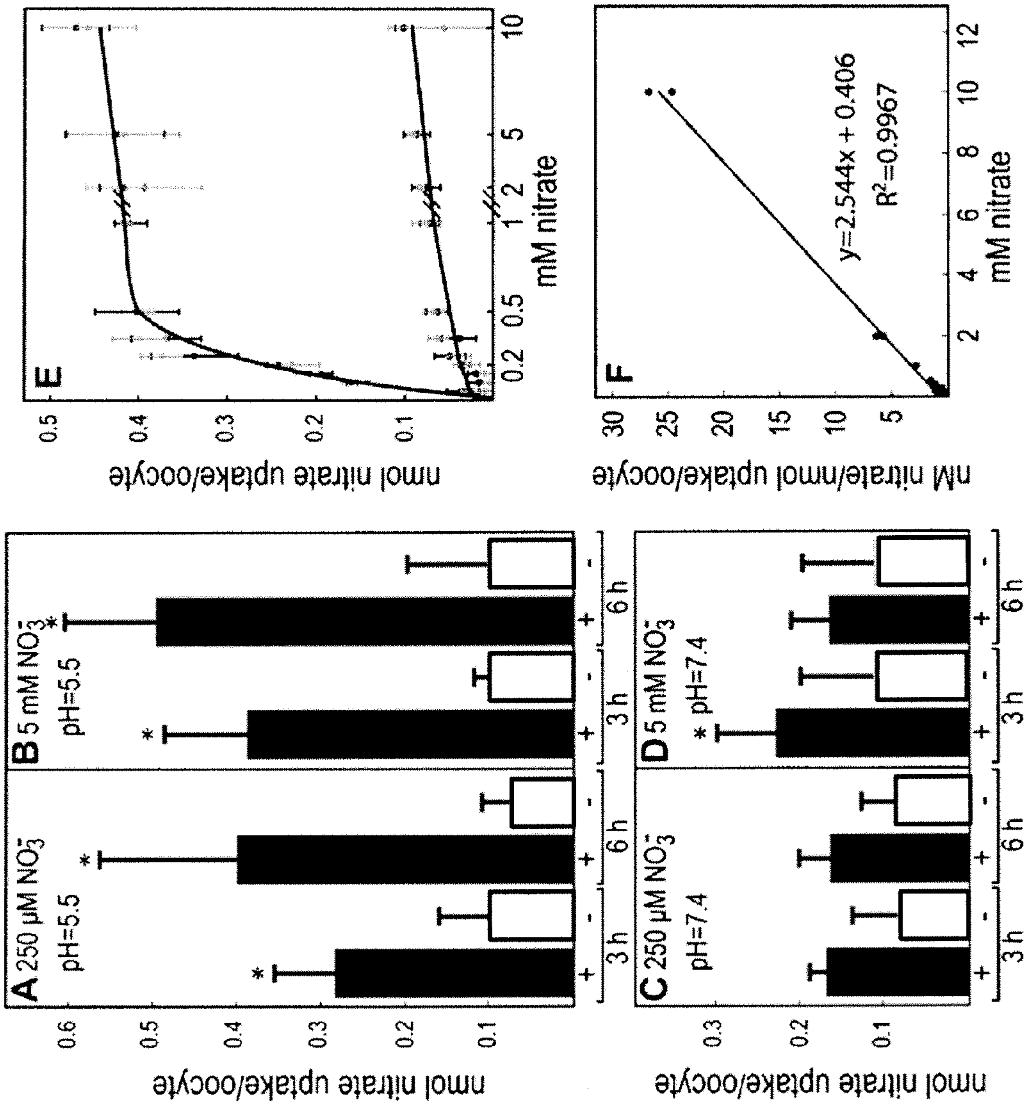
FIG. 9 shows Nitrate uptake in *Xenopus* oocytes expressing MtNIP/LATD. Oocytes were microinjected with MtNIP/LATD mRNA (black bars, +) or water as a negative control (white bars, −), incubated for 3 days, then placed for the indicated times in media containing 250 μM or 5 mM $NO_3^-$ at pH 5.5 or 7.4. The oocytes were rinsed, lysed and assayed for $NO_3^-$ uptake. Panels A, C, 250 μM $NO_3^-$. Panels B, D, 5 mM $NO_3^-$. Panels A, B, pH=5.5. Panels C, D, pH=7.4. Data are shown for one biological replicate plus or minus the standard deviation; n=3-5 batches of 4-6 oocytes per batch. Asterisks mark $NO_3^-$ uptake significantly different from the negative control, using Student's t-test at $p<0.05$. Similar results were obtained in more than 5 repetitions of the experiment. Panel E, Michaelis-Menten plot of oocyte $NO_3^-$ uptake. MtNIP/LATD-injected oocytes (squares) or water-injected oocytes (circles) as control were incubated for 3 h in 50 μM to 10 mM $NO_3^-$ in batches of 5, and assayed for $NO_3^-$ uptake. Results for two biological replicates are indicated by the black and gray symbols, with bars showing the standard deviations. All $NO_3^-$ uptake was significantly different from the negative control, using Student's t-test at $p<0.05$, except for that at 50 μM. Panel F, Hanes-Woolf plot of averaged $NO_3^-$ uptake data, in MtNIP/LATD-injected oocytes minus water-injected oocytes, presented in panel E.
Figure 10:
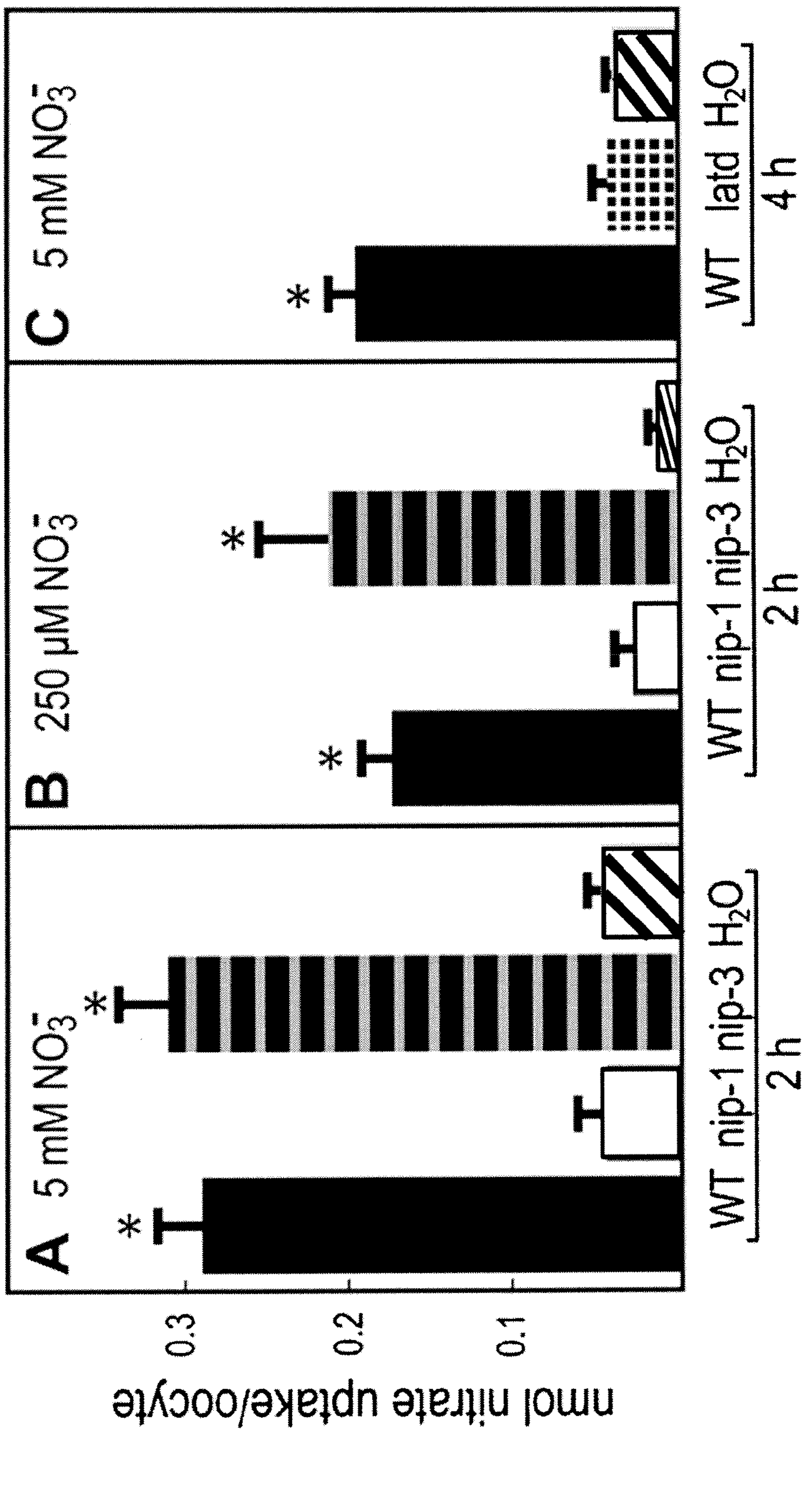
FIG. 10 shows Nitrate uptake in *Xenopus* oocytes expressing MtNIP/LATD or mutant Mtnip/latd mRNAs. Oocytes were microinjected with MtNIP/LATD mRNA, mutant mRNA or water as a negative control, incubated for 3 days, then placed for the indicated times in media containing 5 mM or 250 μM nitrate, at pH 5.5, and assayed for nitrate uptake. Panel A, 5 mM nitrate. Panel B, 250 μM nitrate. Panel C. 5 mM nitrate. Oocytes expressing wild-type MtNIP/LATD (black bars), Mtnip-1 (white bars), Mtnip-3 (horizontally striped bars), Mtlatd (hatched bars) or water as a negative control (diagonal striped bars) are shown. Data are shown for one biological replicate plus or minus the standard deviation; n=3-5 batches of 4-6 oocytes per batch. Asterisks mark nitrate uptake that is significantly different from the negative control, using Student's t-test at $p<0.05$. Similar results were obtained in more than 3 repetitions of the experiment.
Figure 11:
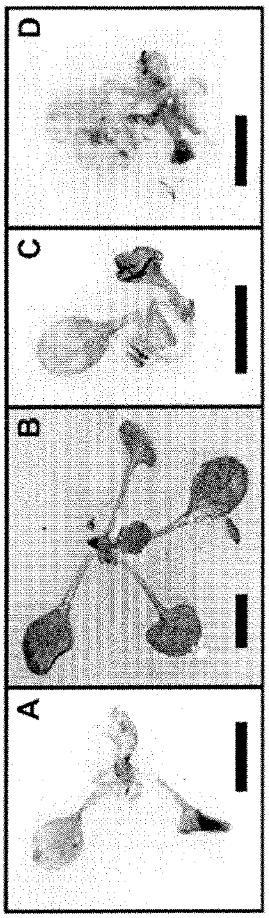
FIG. 11 shows MtNIP/LATD complements the chlorate insensitivity phenotype of the *Arabidopsis* chl1-5 mutant. *Arabidodpsis* chl1-5 plants were transformed with a construct containing MtNIP/LATD cDNA under the control of the *Arabidopsis* EF1 αpromoter, pAtEF1 α-MtNIP/LATD or a positive control construct containing the *Arabidopsis* AtNRT1.1 gene under the same promoter, pAtEF1 α-AtNRT1.1. The plants were treated with chlorate, a $NO_3^-$ analog that can be converted to toxic chlorite after uptake, as described in Tsay et al. 1993. Panel A: *Arabidopsis* Col-0 plants. Panel B: *Arabidopsis* chl1-5 plants. Panel C: *Arabidopsis* chl1-5/pAtEF1α-AtNRT.1.1 plants. Panel D: *Arabidopsis* chl1-5/pAtEF1α-MtNIP/LATD plants. Bars=¼ inch. The MtNIP/LATD gene was able to confer chlorate sensitivity on *Arabidopsis* chl1-5 plants, similar to the AtNRT1.1 gene.
Figure 12:
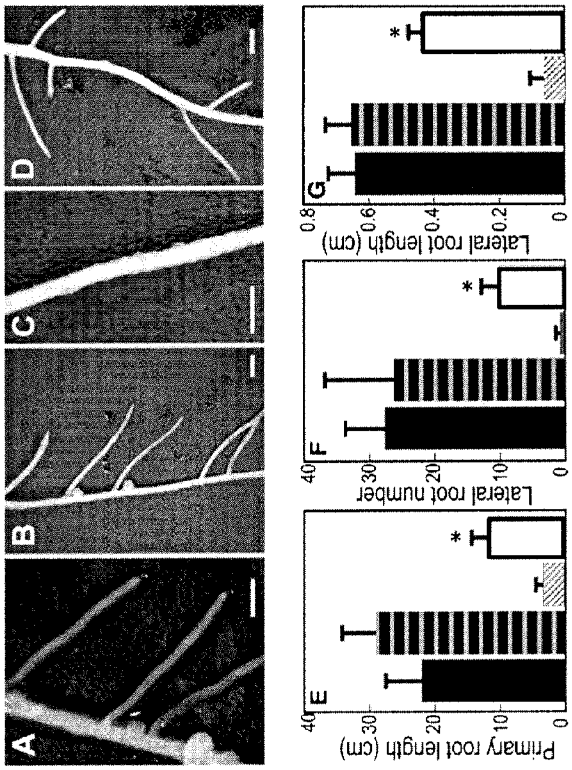
FIG. 12 shows *Arabidopsis* NRT1.1 partially complements the *Medicago* nip-1 mutant for its root architecture phenotype. *Medicago* nip-1 and control wild-type composite plants transformed with pAtEF1α-AtNRT1.1 or empty pCAMBIA2301 vector, as a control, were grown in aeroponic chambers, inoculated with *S. meliloti* containing a constitutive lacZ gene, and grown in 16/8 h light/dark at 22 C. At 15 days post-inoculation, root architecture characteristics were evaluated. Panels A, B, C, D show the appearance of the roots. Bars=10 mm. A: A17, empty vector. B: A17, pAtEF1α-AtNRT1.1. C: nip-1, empty vector. D. nip-1, pAtEF1α-AtNRT1.1. Panels E-G: Quantitation of primary root length (E), lateral root number (F), and lateral root length (G); averaged values with the standard deviation are plotted; n=5. Asterisks mark root attributes that are significantly different from the negative control, using Student's t-test at $p<0.01$. Solid bars: A17, empty vector. Vertically striped bars; A17, pAtEF1α-AtNRT1.1. diagonal striped bars: Mtnip-1, empty vector. White bars. Mtnip-1, pAtEF1α-AtNRT1.1.

To examine whether the mutants had defects in $NO_3^-$ uptake, we grew Mtnip-1 and Mtnip-3 mutants, with wild-type A17 as control, in two different concentrations of $KNO_3$: 250 μM and 5 mM. Uptake was measured by monitoring depletion of $NO_3^-$ from the media. As can be seen in FIG. 7, no differences in $NO_3^-$ uptake were observed in the mutants, suggesting that low and high affinity $NO_3^-$ transport systems are functioning in these plants. However, because measurement of depletion of $NO_3^-$ from the media is less sensitive than measuring $NO_3^-$ influx, subtle changes in $NO_3^-$ uptake may not have been detected in this experimental system.

Figure 2A:
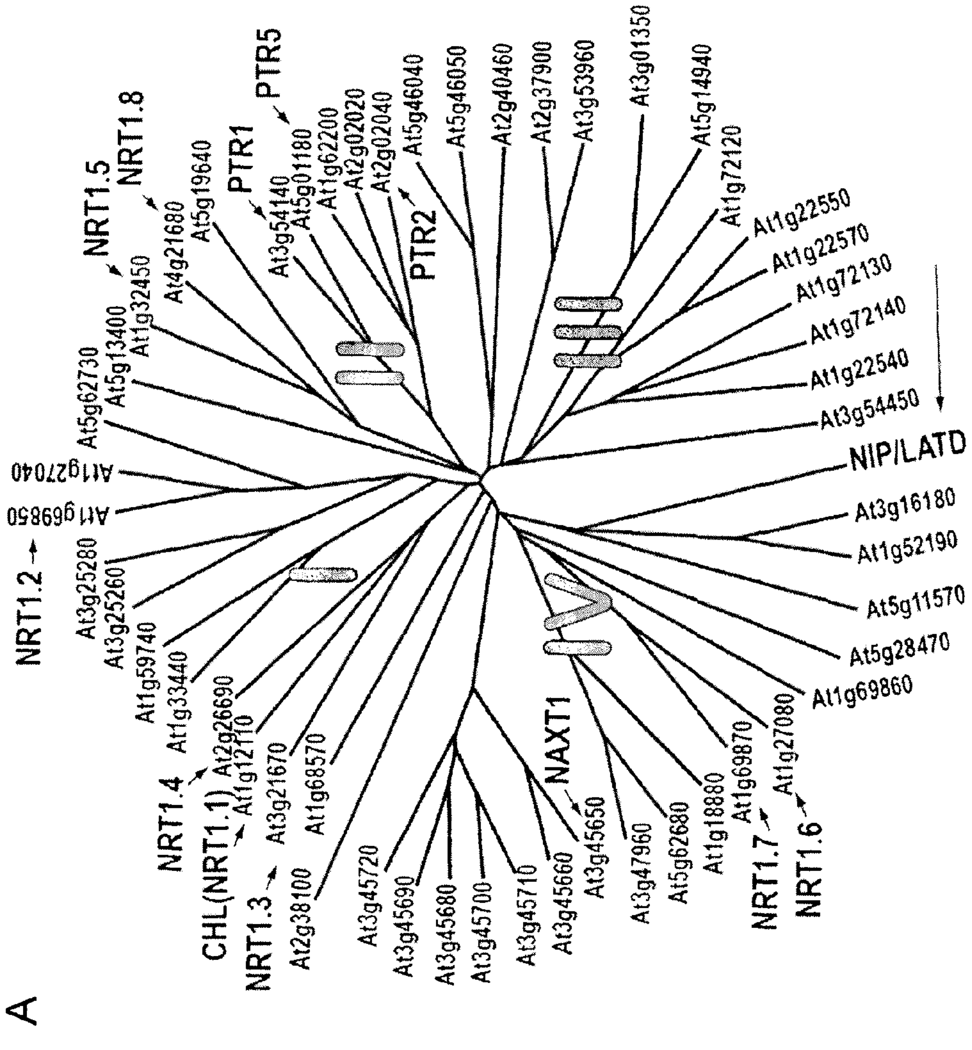
FIG. 2 Panel A shows MtNIP in the NRT1(PTR) transporter family. The phylogeny was created with MtNIP's deduced amino acid sequence with the 53 members of the *Arabidopsis* NRT1(PTR) family, by the neighbor joining method. The white arrow points to MtNIP; black arrow points to CHL(NRT1.1). Proteins identified by a capital (R) have been shown to encode nitrate transporters; those identified by a capital (G) encode di- and tri-peptide transporters. The clades are numbered as in Tsay et al. 2007. MtNIP protein belongs to a Glade that includes nitrate transporters. Panel B shows summarizes NIP gene and known mutants nip-1, latd (nip-2), and nip-3.
Figure 2B:
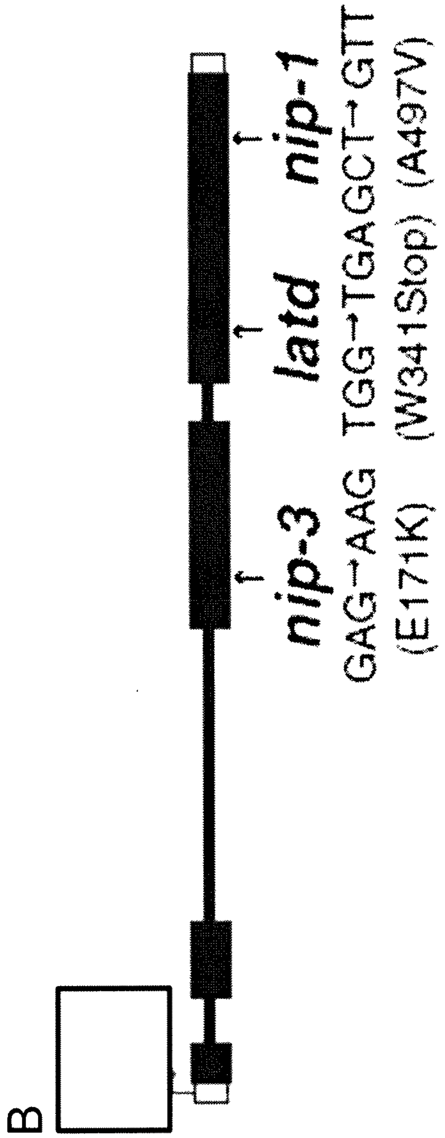

In *Arabidopsis*, growth of plants in different $NO_3^-$ concentrations is known to affect root architecture (Zhang et al., 2000; Linkohr et al., 2002). To determine if Medicago nip mutants' LR phenotype were affected by $NO_3^-$, we grew Mtnip-1, Mtnip-3 and A17 in the presence of 0 μM. 250 μM, and 5 mM $KNO_3$, and examined root growth parameters after two weeks. Wild-type A17 produced longer LRs in both $NO_3^-$ concentrations tested than it did at 0 $NO_3^-$ and slightly shorter LRs in 5 mM as compared to 250 μM $KNO_3$ (FIG. 2). Lateral root lengths of both Mtnip-1 and Mtnip-3 were significantly shorter than those of wild-type in all conditions tested, with one exception; in 5 mM $KNO_3$, the average LR lengths of Mtnip-3 were similar to those of A17. Both Mtnip-1 and Mtnip-3 mutants had longer LRs when grown in 5 mM $KNO_3$ (FIG. 2C) than they did in 250 μM $KNO_3$ (FIG. 2B) and when grown in the absence of $NO_3^-$ (FIG. 2A). These data are consistent with an MtNIP/LATD function in high affinity, low concentration $NO_3^-$ uptake or response.

MtNIP/LATD Protein Transports Nitrate, but not Histidine, in *Xenopus laevis* Oocytes.

Figure 1:
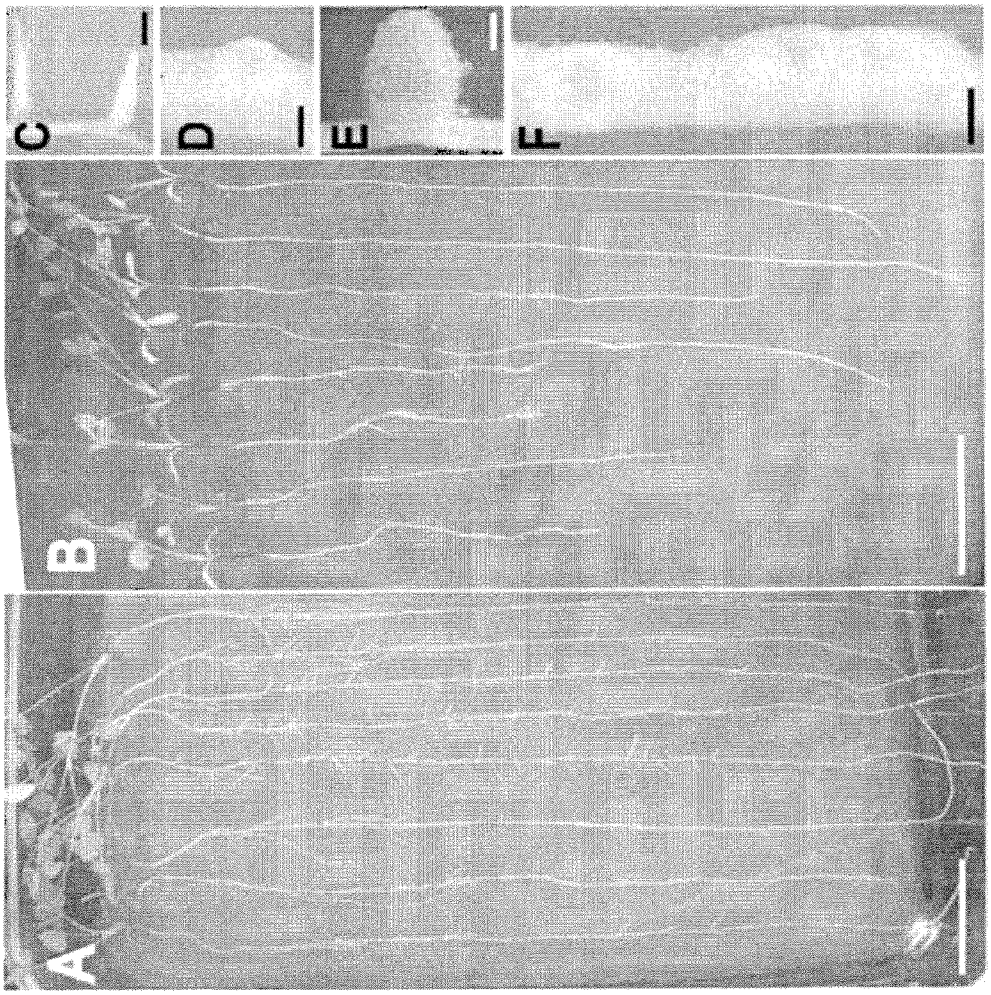
FIG. 1 shows the phenotype of nip-1 and wild-type (A17) plants 15 days post inoculation (dpi) with *Sinorhizobium meliloti*. Plants were grown in aeroponic chambers and placed on an agar support for photography. Panel A shows Wild-type plants. Bar=5.0 cm. Panel B shows, nip-1 plants. Bar=5.0 cm. Panel C shows Wild-type primary root with emergent lateral roots. Bar=1.0 mm. Panel D shows nip-1 lateral root primordium. Bar=0.25 mm. Panel E shows Wild-type nodule. Bar=0.50 mm. Panel F shows nip-1 nodules/bumps. (Note the presence of a dark pigment at the distal ends of the nodules. Bar=0.50 mm.

To test whether the MtNIP/LATD protein transports $NO_3^-$, we expressed MtNIP/LATD in *X. laevis* oocytes and assayed them for acquisition of $NO_3^-$ transport activity. Transport activity was initially assessed at two different $NO_3^-$ concentrations to categorize transporter affinity, and at pH 5.5 and at pH 7.4, to test pH dependence. As shown in FIGS. 3A and B, oocytes expressing MtNIP/LATD were capable of significant $NO_3^-$ uptake above the water injected control oocytes at both low, 250 μM, and high, 5 mM, $NO_3^-$, concentrations at pH 5.5. However, at pH 7.4, there was not significant $NO_3^-$ uptake (FIG. 3C, D), indicating that transport is $H^+$ coupled. We compared MtNIP/LATD $NO_3^-$ transport to that of the dual-affinity AtNRT1.1 transporter and found that MtNIP/LATD had slightly lower nitrate transport than AtNRT1.1 at 250 μM $NO_3^-$. At 5 mM $NO_3^-$, MtNIP/LATD transported approximately 20% as much nitrate as did AtNRT1.1 (Suppl. FIG. 1), suggesting that MtNIP/LATD is not dual-affinity. To determine MtNIP/LATD's Km, we measured $NO_3^-$ uptake in MtNIP/LATD-injected oocytes compared to water-injected control oocytes over $NO_3^-$ concentrations ranging from 50 μM to 10 mM. MtNIP/LATD displays saturable kinetics for $NO_3^-$ uptake, with a Km of 160 μM (FIGS. 3E and F). The data show only one saturation point (FIG. 3E) and thus, indicate that MtNIP/LATD has single, high affinity $NO_3^-$ transport.

Because the NRT1(PTR) family BnNRT1.2 $NO_3^-$ transporter also transports histidine (Zhou et al., 1998), a rat NRT1 (PTR) family member transports both peptides and histidine (Yamashita et al., 1997), and *Arabidopsis* AtPTR1 and AtPTR2 peptide transporters also transport histidine (Tsay et al., 2007), we assessed histidine uptake in MtNIP/LATD-injected oocytes compared to water-injected control oocytes. At pH 5.5 and 1 mM histidine, we observed no histidine transport (Suppl. Table 1).

Proteins Encoded by Two MtNIP/LATD Mutant Alleles but not a Third Allele are Defective in Nitrate Transport in the Oocyte System.

The finding that MtNIP/LATD transports $NO_3^-$ opens the possibility that the defects observed in the Mtnip/latd mutants result from defective $NO_3^-$ transport. To determine if the proteins encoded by the available defective MtNIP/LATD genes are capable of $NO_3^-$ transport, we tested them in the *X. laevis* oocyte system. The results demonstrate that the missense Mtnip-1 and truncated Mtlatd proteins are defective in $NO_3^-$ transport at 5 mM $NO_3^-$, while the Mtnip-3 protein is capable of transport at this higher concentration (FIG. 4). Oocytes expressing Mtnip-3 protein as well as Mtnip-1 protein were assessed for high affinity transport at 250 μM $NO_3^-$; since the Mtlatd protein, encoded by a gene with a nonsense codon in the middle of MtNIP/LATD, failed to transport $NO_3^-$ at 5 mM $NO_3^-$, it was not tested for transport at 250 μM $NO_3^-$. Mtnip-3 was capable of transport at 250 μM, while Mtnip-1 was not. Because the Mtnip-3 mutant has defective root architecture, aberrant nodulation, and fixes far less N than wild-type (Teillet et al., 2008), we conclude that it is defective in another function besides $NO_3^-$ transport.

MtNIP/LATD Expression in the *Arabidopsis* chl1-5 Mutant Restores Chlorate Sensitivity.

Although MtNIP/LATD transports $NO_3^-$ in oocytes, it could be argued that it may not function as a $NO_3^-$ transporter in planta. The $NO_3^-$ transporter activity of MtNIP/LATD was further tested by studying its ability to complement the well-characterized *Arabidopsis* chl1-5 mutant, containing a large deletion in the AtNRT1.1 gene (Munos et al., 2004). This mutant was originally isolated on the basis of its resistance to the herbicide chlorate, which is taken up through the AtNRT1.1 (AtCHL1) $NO_3^-$ transporter and reduced by $NO_3^-$ reductase to toxic chlorite (Doddema et al., 1978; Tsay et al., 1993). Complementation of this phenotype is easy to score. A construct containing MtNIP/LATD cDNA under the control of the constitutive *Arabidopsis* EF1αpromoter (pAtEF1α-MtNIP/LATD) was introduced into Atchl1-5 plants, with plants transformed by AtNRT1.1 cDNA regulated by the same promoter (pAtEF1α-AtNRT1.1) serving as positive control. Atchl1-5/pAtEF1α-MtNIP/LATD was found to be sensitive to chlorate, similar to the positive control Atchl1-5 plants transformed with pAtEF1α-AtNRT1.1 and wild-type Col-0. Negative control mutant Atchl1-5 plants were resistant to chlorate, as expected (FIG. 5, Suppl. FIG. 2). Wild-type AtCol-0 and the Atchl1-5 plants constitutively expressing either AtNRT1.1 or MtNIP/LATD showed a reduction in fresh weight and chlorophyll content after chlorate treatment compared to the resistant Atchl1-5 plants (Table II). A second independent transformed line of Atchl1-5 transformed with pAtEF1α-MtNIP/LATD was also constructed and found to be chlorate sensitive as well (Suppl. FIG. 2). We therefore conclude that since MtNIP/LATD transports the $NO_3^-$ analog chlorate in planta, it is extremely likely to transport $NO_3^-$ in planta as well.

AtNRT1.1 but not AgDCAT1, Partially Rescues the *Medicago* Nip-1 Phenotype.

Since MtNIP/LATD restored chlorate sensitivity to the *Arabidopsis* chl1-5 mutant, we tested whether AtNRT1.1 would restore the *Medicago* nip-1 mutant to its wild-type phenotype. At the time that this experiment was performed, AtNRT1.1 was the only NRT1(PTR) member known to be a high affinity (dual affinity) $NO_3^-$ transporter (Tsay et al., 2007). We used composite *Medicago* plant hairy roots (Boisson-Dernier et al., 2001) transformed with pAtEF1α-AtNRT1.1 as our test system. Composite plants were grown in aeroponic chambers in the absence of $NO_3^-$, inoculated with *Sinorhizobium meliloti*/phemA::lacZ (Boivin et al., 1990), and root architecture and nodulation were evaluated at 15 days post inoculation (dpi). The results showed that AtNRT1.1 partially restored Mtnip-1 root architecture (FIG. 6). The Mtnip-1 mutants transformed with the AtNRT1.1 expression construct had longer primary roots, more elongated LRs and longer LRs than Mtnip-1 mutants transformed with empty vector. However, the nodules in Mtnip-1 plants transformed with the pAtEF1α-AtNRT1.1 construct had an Mtnip-1-phenotype, with the presence of brown pigments, no obvious meristem, and did not differentiate into the zones that are the hallmark of nitrogen fixing nodules (FIG. 7). Control plants transformed with pAtEF1α-MtNIP/LATD had wild-type phenotype nodules (FIG. 7F), and show comparable rescue of nodulation and root architecture phenotypes as those transformed with pMtNIP, LATD-MtNIP/LATD (Suppl. FIG. 3) showing that use of the *Arabidopsis* EF1α promoter is not a limiting factor for complementation of the Mtnip-1 phenotype. Overall, the experiment shows that although AtNRT1.1 partially restores the root architecture phenotype, it is not able to restore normal nodulation to the Mtnip-1 plants.

We also tested whether the gene encoding the alder symbiotic AgDCAT1 dicarboxylate transporter could restore normal root development or nodulation to Mtnip-1 plants, using a similar approach as for AtNRT1.1, in composite transformed plants. Mtnip-1 plants expressing AgDCAT1 had a phenotype indistinguishable from Mtnip-1 plants transformed with an empty vector; in contrast. Mtnip-1 plants expressing MtNIP/LATD were restored to wild-type. Wild-type A17 plants' phenotypes were unaffected by AgDCAT1 expression (Suppl. FIG. 3).

Discussion

The major finding of the work reported here is that MtNIP/LATD protein is a $NO_3^-$ transporter, and its $NO_3^-$ transport activity partially correlates with root architecture development. Our results also show that MtNIP/LATD has another unknown biochemical activity which is important to MtNIP/LATD's biological roles in nodule development and in the modulation of root architecture.

Data for MtNIP/LATD $NO_3^-$ transport come from two complementary experimental approaches. When MtNIP/LATD is expressed in the heterologous *X. laevis* oocyte system, it enables the oocytes to transport $NO_3^-$ in a pH dependent manner, demonstrating that $NO_3^-$ transport is Fr driven (FIG. 3), similar to other $NO_3^-$ transporters in the NRT1 (PTR) family (Tsay et al., 1993). $NO_3^-$ uptake was characterized as having a Km of 160 μM, making it a high-affinity (HATS) transporter. A second line of evidence that MtNIP/LATD is a $NO_3^-$ transporter is that its gene's constitutive expression can complement the *Arabidopsis* chl1-5 mutant, containing a deletion spanning the AtNRT1.1 gene (Munos et al., 2004). Atchl1-5 mutants expressing MtNIP/LATD are susceptible to chlorate, indicating that MtNIP/LATD confers on them the ability to take up the herbicide chlorate, a $NO_3^-$ analog, from the media (FIG. 5). Both approaches showing MtNIP/LATD transports $NO_3^-$ indicate that the direction of $NO_3^-$ transport is from outside to inside cells.

Although not wanting to be bound by theory. One might expect Mtnip/latd mutants to exhibit defects in $NO_3^-$ uptake. We measured $NO_3^-$ uptake from media by Mtnip-1 and Mtnip-3 mutants and control wild-type *Medicago* A17, and observed no differences between the plants in $NO_3^-$ uptake at either 250 μM or at 5 mM $NO_3^-$, representative of HATS and LATS respectively (FIG. 1). This suggests that MtNIP/LATD is not a rate-limiting transporter for $NO_3^-$ uptake into plant tissue. MtNIP/LATD is expressed in primary and lateral root tips (Yendrek et al., 2010); if MtNIP/LATD's primary biological role is to transport $NO_3^-$, it may constitute only a small portion of $NO_3^-$ transport in *Medicago* roots. It is also possible that in Mtnip/latd mutants, the plant compensates by upregulating the activity of another transporter. Another possibility is that MtNIP/LATD's transport function may be critical for redistribution of $NO_3^-$ within the plant. We found that Mtnip-1 is apparently normal for $NO_3^-$ suppression of nodulation (Table 1), leading us conclude that MtNIP/LATD is likely not involved in this pathway (Streeter, 1988; Fei and Vessey, 2008), and/or there are other $NO_3^-$ transporters that can compensate for this function.

Previously, the effects of 10 mM and 50 mM $KNO_3$ on primary root length and LR density in Mtlatd mutants were monitored; Mtlatd plants, like wild type, do not show altered LR density in response to global increases in $NO_3^-$ (Yendrek et al., 2010). Here, we examined LR lengths of Mtnip-1 and Mtnip-3 plants grown in 0 μM, 250 μM or 5 mM $KNO_3$ and found that the LR length phenotype was rescued for Mtnip-3 and partially rescued for Mtnip-1 at the 5 mM $KNO_3$ level, but not at 250 μM $KNO_3$ (FIG. 2), suggesting that MtNIP/LATD might have a more biologically important role at lower $NO_3^-$ concentrations than at higher ones. However, these experiments did not control for the effects of salt concentration on root architecture, which could have affected abscisic acid levels, leading to changes in LR lengths (Liang and Harris, 2005; Liang et al., 2007), and thus are only suggestive.

Even though nitrate uptake was not limited in Mtnip/latd mutants compared to wild type plants, nitrate uptake differed when these alleles were expressed in oocytes and assayed for nitrate transport. Nitrate uptake experiments in the oocyte system showed that the protein encoded by the weakest allele, Mtnip-3, transported $NO_3^-$ indistinguishably from wild-type, while the proteins encoded by the two more severe alleles. Mtnip-1 and Mtlatd, did not (FIG. 4). The Mtnip-3 mutant has a phenotype: it forms Fix+/− nodules that accumulate polyphenolics, and has minor defects in root architecture, in primary (Teillet et al., 2008; Yendrek et al., 2010) and lateral (FIG. 2) root length. Thus, there is a correlation between MtNIP/LATD's ability to transport $NO_3^-$ and Mtnip/latd mutants' abilities to form and maintain nodule and root meristems and to form nodules invaded intracellularly by rhizobia. Despite that $NO_3^-$ transport by Mtnip-3 protein is indistinguishable from the transport by wild-type MtNIP/LATD. Mtnip-3 has a root and nodule phenotype. This indicates that MtNIP/LATD must have at least one other function besides $NO_3^-$ transport.

To further address the possible link between MtNIP/LATD and $NO_3^-$ transport, we expressed AtNRT1.1 in Mtnip-1 roots. We observed that the AtNRT.1.1-transformed Mtnip-1 plants are partially restored for their root architecture phenotype, but not for the nodulation phenotype. The use of pAtEF1α is not a limiting factor for phenotype rescue, since MtNIP/LATD, expressed under the control of the same promoter was able to restore both the root architecture phenotype (not shown) and the nodulation phenotype (FIG. 7). No effect was observed when AtNRT1.1 was expressed in wild-type A17 plants (FIGS. 6 and 7). This suggests that AtNRT1.1 protein's dual affinity $NO_3^-$ transport activity affects Mtnip-1 root architecture, and supports the idea that MtNIP/LATD's $NO_3^-$ transport activity has an important role in modulating root developmental responses. Additionally, the lack of full complementation of the root architecture defects by AtNRT1.1 and the non-complementation of the nodulation phenotype by AtNRT1.1 suggest that there is a function of MtNIP/LATD that is different from that of AtNRT1.1. Alternatively, it is possible that AtNRT1.1 is not as stable in *Medicago* as is MtNIP/LATD, especially in nodules, and that this is the cause of AtNRT1.1's inability to complement Mtnip-1's nodulation phenotype. Because AtNRT1.1 has been demonstrated to transport auxin in the absence of $NO_3^-$ (Krouk et al., 2010), and $NO_3^-$ was only provided during plant transformation in these experiments, another possible explanation for the observed effects on Mtnip's roots is that the partial restoration of normal root architecture was brought about by AtNRT1.1 induced changes in auxin concentration. When normally expressed in *Arabidopsis*, AtNRT1.1 is thought to prevent auxin accumulation at LR tips by mediating basipetal auxin transport in LRs, thus halting LR growth (Krouk et al., 2010); this is the opposite of what we observed in the Mtnip-1 mutant expressing AtNRT1.1 (FIG. 6). Because our experiments used a constitutive promoter to express AtNRT1.1, it is possible that the perturbation of auxin gradients within the roots caused the observed changes in root architecture. It is also curious that the nodule phenotype of Mtnip-1 plants transformed with AtNRT1.1 is different from that of Mtnip-3. If the ability of Mtnip-3 nodules to form a meristem and allow rhizobia to invade intracellularly is related to Mtnip-3 protein's ability to transport $NO_3^-$, one would expect to find the same phenotype in Mtnip-1 plants transformed with AtNRT1.1 as in Mtnip-3, which is not the case. This datum further supports the idea that MtNIP/LATD protein's activity is more than simply $NO_3^-$ transport and is also not explained by the spectrum of activities inherent in AtNRT1.1.

What role could MtNIP/LATD mediated $NO_3^-$ transport play in nodulation, root architecture development or their regulation? MtNIP/LATD $NO_3^-$ transport could supply N at low $NO_3^-$ concentrations to dividing plant and bacterial cells early in nodulation, and also to differentiated nodules, at the dividing and endo-reduplicating cells present in zones I and II, where MtNIP/LATD's promoter is active (Yendrek et al., 2010). The MtNIP/LATD promoter is also active in primary root meristems, LR primordia and meristems and surrounding tissue, and MtNIP/LATD $NO_3^-$ transport could have a similar role there. In this case, the supply of $NO_3^-$ to these tissues would provide the N required for basic cellular functions required by dividing primordial tissues distant from the primary meristem, and facilitating the transition from primordium to self-sustaining meristem by these nascent lateral root organs.

Alternately, MtNIP/LATD could transport $NO_3^-$ as a precursor to the potent signaling molecule nitric oxide (NO), early in nodulation and LR development. NO has been detected in *Medicago* nodule primordia, not containing intracellular rhizobia, suggesting an active NO pathway in these cells, as well as in infection threads, where NO could come from either symbiotic partner (del Giudice et al., 2011). NO has also been detected in LR primordia in tomato (Correa-Aragunde et al., 2004). We note however, that nodulation occurs in environmental conditions where N is limiting; indeed, our laboratory conditions for nodulation occur in N starvation. We supply 0 μM $NO_3^-$ during nodulation and only the trace $NO_3^-$, expected to be in the μM range, present as contaminants in nutrient media and glassware are available. If $NO_3^-$ is supplied to dividing nodule cells, it must come from seed $NO_3^-$ stores, which should be close to depleted by the time nodules are forming or be re-mobilized from other N-rich components within the plant. Another possibility is that MtNIP/LATD $NO_3^-$ transport could participate in a proposed $NO_3^-$—NO respiration pathway in nodules (Horchani et al., 2011; Meilhoc et al., 2011). There are several observations that argue against this: Mtnip-3, with functional $NO_3^-$ transport (FIG. 4), has abnormal nodules (Teillet et al., 2008); MtNIP/LATD's promoter is active in nodule meristems and in the invasion zone and not in the N-fixing zone (Yendrek et al., 2010), suggesting that MtNIP/LATD may be absent in the N-fixing zone; and the heterologous MtNIP/LATD expression experiments suggest direction of $NO_3^-$ transport is towards the cytosol, which is opposite to that suggested for a $NO_3^-$ transporter in the proposed $NO_3^-$—NO pathway.

Because MtNIP/LATD has another function besides $NO_3^-$ transport, it is plausible that the other function is responsible for some of the Mtnip/latd mutants' phenotypes. Here, we have presented data suggesting that neither histidine nor dicarboxylates are substrates for MtNIP/LATD transport (Suppl. Table 1 and Suppl. FIG. 3). We and others have speculated that MtNIP/LATD may be a $NO_3^-$ transceptor or sensor (Harris and Dickstein, 2010; Yendrek et al., 2010; Gojon et al., 2011). If it is a $NO_3^-$ transceptor or sensor, we predict that it may be responsible for high-affinity $NO_3^-$ sensing. This is because it is a high-affinity transporter and because the root architecture phenotypes are partially rescued by high, but not low $NO_3^-$ concentrations (FIG. 2). It is also possible that MtNIP/LATD is able to transport a hormone like AtNRT1.1 (Krouk et al., 2010) and AtNRT1.2 (Kanno et al., 2012), and that is responsible for the other function(s) of MtNIP/LATD.

Materials and Methods

Plant Growth Conditions.

*M. truncatula* A17 (wild-type) and nodulation mutants were grown in aeroponic chambers with Lullien media (Lullien et al., 1987), starved for nitrogen for five days and inoculated with *S. medicae* strain ABS7 (Bekki et al., 1987) or *S. meliloti* strain Rm2011 (Rosenberg et al., 1981) harboring pXLGD4 (Boivin et al., 1990; Penmetsa and Cook, 1997) as previously described (Veereshlingam et al., 2004; Pislariu and Dickstein, 2007). For experiments where *Medicago* plants were grown in the presence of N sources, the relevant N sources were added to Lullien media from the beginning of the experiment and inoculations were done with ABS7/pXLDG4. At 15 dpi, plants were stained with X-Gal to identify nodules. *Arabidopsis* plants were grown as described (Srivastava et al., 2008) at 22 C with a 16:8 light:dark light regime.

Nitrate Uptake Studies in *Medicago*.

A17, Mtnip-1, and Mtnip-3 seedlings were surface sterilized, germinated and placed on buffered nodulation media (BNM) (Ehrhardt et al., 1992) solidified with agar, pH 5.8, supplemented with 5 mM $NH_4NO_3$ and grown for 7 days at 22 C with a 16:8 light:dark light regime, with roots shielded from the light. Plants were transferred to nitrogen-free BNM agar and grown for three days to starve them for nitrogen. Plants were placed in liquid BNM media supplemented with either 250 μM or 5 mM $KNO_3$. Samples from the media were collected at the indicated times and assayed for $NO_3^-$ using the Cayman (Ann Arbor, Mich., #780001) $NO_3^-/NO_2^-$ assay kit following manufacturer's instructions.

Construction of Oocyte Expression Vectors.

RNA was extracted from *M. truncatula* A17 plants and mutant Mtnip-1, Mtlatd and Mtnip-3 using the RNeasy kit (Qiagen, Germantown, Md.). First strand cDNA was transcribed using oligo dT and Superscript III™ reverse transcriptase (Invitrogen, Carlsbad, Calif.) and the wild-type MtNIP/LATD and mutant Mtnip/latd cDNAs were made using MtNIP/LATD specific primers NIPcEXP1R, NIPcExp1F and NIPcDNANhel_F (Suppl. Table 2) via PCR with Phusion™ high-fidelity DNA polymerase (New England Biolabs, Beverly, Mass.). The resulting 1776 bp cDNAs were cloned into transcription vectors pSP64T (Krieg and Melton, 1984) and pcDNA™3.1(−) (Invitrogen). AtNRT1.1 cDNA was amplified from pMS008 (see below) using primers Chl_1F and Chl_1R, cloned into PCR8/GW/TOPO, and then moved into pOO2/GW (gift from Dr. John Ward) downstream of an SP6 promoter. All clones were verified by DNA sequencing.

Binary Vectors.

MtNIP/LATD cDNA was amplified with NIPC2F and NIPCODBst1R, digested with NcoI and BstEII and ligated into a vector containing the AtEF1α promoter engineered to contain a 5' BamHI site and a 3' NcoI site, making a precise translational fusion, creating pMS004. Subsequently the AtEF1α-MtNIP/LATD cDNA fragment was cloned into the BamHI and BstEII site of binary vector pCAMBIA2301. AtNRT1.1 cDNA was amplified from total cDNA made from wild-type Col-0 *Arabidopsis* mRNA using primers CHL11F and CHL11R, digested with BspHI and BstEII and cloned into NcoI and BstEII digested pMS004 to obtain pMS008. The pAtEF1α-AtNRT1.1 fragment was then subcloned into the BamHI and BstEII sites of pCAMBIA2301. For the pMtNIP/LATD-MtNIP/LATD construct, the pAtEF1α in pMS004 was replaced by 3 kbp upstream region of MtNIP/LATD amplified using NIP10F and NIP P1R primers, followed by EcoR1 and NcoI/BspHI digestion to create the pMS006 clone. Then the pMS006 EcoRI/BstEII fragment was moved into the EcoRI/BstEII site of pCAMBIA2301. AgDCAT1 cDNA was PCR amplified from pJET1.2-AgDC471 (gift of Dr. K. Pawlowski) using DC-BglII and DC NheI primers and cloned into the BamHI and NheI sites of pMS014 vector, a vector containing the MtNIP/LATD promoter only, to create pMS015. Then the pMS015 EcoRI/BstEII fragment was moved into the EcoRI/BstEII site of pCAMBIA2301 to create the pMtNIP/LATD-AgDCAT1 construct. FIG. 15 shows the primer sequences.

Nitrate and Histidine Uptake in *Xenopus laevis* Oocytes.

Capped mRNA was transcribed in vitro from linearized plasmid using SP6 or T7 RNA polymerase (mMESSAGE mMACHINE, Ambion, Austin, Tex.). Collagenase treated oocytes were isolated and microinjected with approximately 50 ng RNA in 50 nl sterile $H_2O$. Oocytes microinjected with 50 nl sterile $H_2O$ were used as negative controls. Oocytes were incubated in ND96 solution (Liu and Tsay, 2003) for 24-40 h at 18 C. For $NO_3^-$ uptake, ooctyes were incubated in a solution containing 230 mM mannitol, 15 mM $CaCl_2$, 10 mM HEPES (pH 7.4), containing various $KNO_3$ concentrations at pH 5.5 or 7.4, at 16 C for the indicated times. After incubation, batches of four to six oocytes were lysed in 40 μL $H_2O$, centrifuged at 13,500×g for 20 min and the supernatant analyzed for $NO_3^-$ content, as above. For histidine uptake, oocytes were incubated in ND96 media pH 5.5 at 25 C containing 1 mM uniformly $^{13}C$-labeled histidine (Cambridge Isotope, Andover, Mass.). After incubation, oocytes were washed five times with the same medium containing 10 mM unlabeled histidine (Sigma Aldrich, St. Louis, Mo.) and batches of eight oocytes were lysed in 100 μL $H_2O$ and centrifuged at 13,500×g for 20 min. The supernatant was concentrated into 15 μL using a lyophilizer and analyzed using ultra performance liquid chromatography-electrospray ionization-tandem mass spectrometry (UPLC-ESI-MS/MS).

UPLC-ESI-MS/MS Analysis.

$^{13}C_6$-histidine was quantified using a precolumn derivatization method with 6-aminoquinolyl-N-hydroxysuccinimidyl carbamate (AQC) combined with UPLC-ESI-MS/MS. AQC derivatization was performed using the AccQ·Tag derivatization kit (Waters Corp., Milford, Mass.) according to the manufacturer's protocol. UPLC-ESI-MS/MS analysis was carried out on a Waters Acquity UPLC system interfaced to a Waters Xevo TQ mass spectrometer as described (Salazar et al., 2012). Briefly, the AQC derivatized $^{13}C_6$-histidine was separated on a Waters AccQ·Tag Ultra column (2.1 mm i.d.× 100 mm, 1.7 μm particles) using AccQ·Tag Ultra eluents (Waters Corp.) and gradient described earlier (Salazar et al., 2012). The sample injection volume was 1 μL, the UPLC column flow rate was 0.7 mL/min, and the column temperature was 55 C. Mass spectra were acquired using positive electrospray ionization and the multiple reaction monitoring mode, with the following ionization source settings: capillary voltage, 1.99 kV (ESI+); desolvation temperature, 650 C; desolvation gas flow rate, 1000 L/h; source temperature, 150° C. Argon was used as collision gas at a flow rate of 0.15 mL/min. The collision energy (CE) and cone voltage (CV) were optimized for $^{13}C_6$-histidine using the IntelliStart software (CE=26 eV; CV=20 V). The most sensitive parent-daughter ion transition of derivatized histidine (m/z 332.1>171.0) was selected for quantitation. The mass spectrometer response was calibrated by injecting AQC-derivatized-$^{13}C_6$-histidine standard solutions of known concentration. The UPLC-ESI-MS/MS system control and data acquisition were performed with Waters Corp. MassLynx™ software. Data analysis was conducted with TargetLynx™ software (Waters Corp.).

Transformation of Atchl1-5 Plants with MtNIP/LATD Expression Construct.

MtNIP/LATD expression construct (pAtEF1α-MtNIP/LATD) was transformed into *Agrobacterium tumefaciens* GV3101(pMP90) strain by electroporation. Positive colonies were selected by colony PCR, verified by restriction digestion, and transformed into Atchl1-5 mutant (Tsay et al., 1993) by the floral dip method (Clough and Bent, 1998). Seeds were collected and transformed plants were selected on kanamycin media. Two independent homozygous transformed lines of Atchl1-5 transformed with pAtEF1α-MtNIP/LATD were selected.

Chlorate Sensitivity Test.

Plants were grown in vermiculite:perlite (1:1 mixture) under continuous illumination at 25-27 C. Plants were irrigated every 2-3 d with medium containing 10 mM $KH_2PO_4$ (pH 5.3), 5 mM $KNO_3$, 2 mM $MgSO_4$, 1 mM $CaCl_2$, 0.1 mM FeEDTA, 50 pM $H_3BO_3$, 12 pM $MnSO_4$, 1 pM ZnCl, 1 pM $CuSO_4$, and 0.2 pM $Na_2MoO_4$. At 5-7 d post germination, plants were irrigated twice with media containing 2 mM $NaClO_3$, without $NO_3^-$. Three days after $ClO_3^-$ treatment, plants were switched to irrigation media lacking $ClO_3^-$ and $NO_3^-$. Plants were examined 7-10 d after $ClO_3^-$ treatment for necrosis and bleaching symptoms characteristic of chlorate toxicity (Wilkinson and Crawford, 1991), and their fresh weight and chlorophyll contents were obtained. Digital color photographs of the plants were obtained, corrected for color balance (Suppl. FIG. 2), converted to grayscale and corrected for contrast (FIG. 5) using the auto-contrast features of Photoshop (Adobe Software).

Chlorophyll content was determined from approximately 10 mg fresh leaves that were weighed, frozen in liquid $N_2$, ground to fine powder, added to tubes with 100 μL $H_2O$ and 8 mL 96% ethanol and mixed. The tubes were kept at 25 C overnight, mixed again and the particulates allowed to settle. The absorbance was recorded at 648.6 nm and 664.2 nm. Total chlorophyll was calculated as described (Lichtenthaler, 1987).

*Medicago* Hairy Root Transformation by Expression Constructs.

Vectors containing the expression constructs were transformed into *Agrobacterium rhizogenes* ARqua1 strain (Quandt et al., 1993) and *A. tumefaciens* MSU440 by the freeze thaw method (Hofgen and Willmitzer, 1988). Positive ARqual colonies were transformed into Mtnip-1 and A17 plants by the needle poking method (Mortier et al., 2010). Transformed composite plants were grown as previously described (Pislariu and Dickstein, 2007).

Analysis of Lateral Root and Nodules in Transformed Plants.

Root nodules were analyzed at 12 dpi. After visual inspection, they were stained with X-GAL for lacZ, present in pXLGD4 plasmid in *S. medicae* ABS7. Subsequently, the nodules were mounted in 2.5% LMP agarose and 50 μm sections were obtained using a 1000 Plus Vibratome (Vibratome, Bannockburn, Ill.) and observed by light microscopy. Lateral roots were inspected visually and under a dissecting microscope.

Example 7

*Arabidopsis* is a genus in the family Brassicaceae. They are small flowering plants related to cabbage and mustard. This genus is of great interest since it contains thale cress (*Arabidopsis thaliana*), one of the model organisms used for studying plant biology and the first plant to have its entire genome sequenced. Meristems are the adult body of vascular plants is the result of meristematic activity. Although not wanting to be bound by theory, plant meristems are centers of mitotic cell division, and are composed of a group of undifferentiated self-renewing stem cells from which most plant structures arise. Apical meristems are located at the growing tips of the adult plant, and produce root and shoot tissue. Shoot apical meristems (SAM) (2105) initiate leaves during vegetative development, and inflorescence (IM) (2110) and floral meristems (FM) (2120) during reproductive development.

Turning to FIG. 21 showing *Arabidopsis* wild type plants (2101) and plants constitutively expressing MtNIP/LATD (2102) about 40 days after germination and grown without supplemental nitrogen fertilizer. Panel A shows a top view and side view of the wild-type non-transformed control plants, represented as *Arabidopsis* Col-0. Panel B shows top view and side view of the *Arabidopsis* Col-0 plants constitutively expressing MtNIP/LATD, using the constitutive AtEF1αpromoter. The IM (2110) and FM (2120) are found in 40 day old plants constitutively expressing MtNIP/LATD, but not in wild type plants. The side view clearly shows white flower stalks on most of the plants in Panel B, in contrast to the absence of such flowers in Panel A.

Turning to FIG. 22 showing *Arabidopsis* plants transformed with both missense alleles of MtNIP/LATD, in order to correlate ability of their encoded proteins to transport nitrate with function in promoting growth. Panel A shows the top and side view of *Arabidopsis* Col-0 plants constitutively expressing Mtnip-3 (2201), using the constitutive AtEF1α-promoter, wherein Mtnip-3 transports nitrate in *Xenopus oocytes* and causes larger plants that flower earlier. The *Arabidopsis* Col-0 plants constitutively expressing Mtnip-1 (2202), using the constitutive AtEF1αpromoter. Mtnip-1 does not transport nitrate in *Xenopus oocytes* and does not cause larger plants that flower earlier.

The constitutive expression of the *Arabidopsis* NRT1.1 gene was tested using the same constitutive AtEF1α promoter. More specifically, FIG. 23 shows the effects of expressing an *Arabidopsis* NRT1.1 gene that encodes a dual affinity nitrate transporter, which is capable of transporting nitrate with both high and low affinity. It has also been shown to transport nitrate.

Turning now to FIG. 23, Panel A shows the *Arabidopsis* Col-0 plants (2301) constitutively expressing AtNRT1.1, using the constitutive AtEF1α promoter. The NRT1.1 is capable of transporting nitrate in *Xenopus oocytes*. Expression of AtNRT1.1 causes slightly larger plants and several of the plants flower earlier. Additionally, two other species have shown similar results. For example, *Medicago truncatula* plants having about the same age in the T1 generations are shown in FIG. 23 Panel B, wherein the two plants on the left (2330) are *Medicago truncatula* plants constitutively expressing MtNIP'LATD, and the plant on the right (2340) is also transformed, but is expressing an unrelated gene, GUS.

Example 8

*Medicago truncatula* (Barrel Medic or Barrel Medick or Barrel Clover) is a small legume native to the Mediterranean region. It is a low-growing, clover-like plant 10-60 cm tall with trifoliate leaves. Each leaflet is rounded, 1-2 cm long, often with a dark spot in the center. Generally, the flowers are yellow, produced singly or in a small inflorescence of 2-5 together; the fruit is a small spiny pod. Turning now to FIG. 24, Panel A, shows the *M. truncatula* plants transformed with a control GUS construct, wherein the figure shows the plants (2410) are not flowering. In contrast, FIG. 24 Panel B are *M. truncatula* plants constitutively expressing MtNIP/LATD flower sooner (2420). As indicated, the *M. truncatula* plants constitutively expressing MtNIP/LATD flower sooner when compared to the control plants transformed with the GUS construct.

Example 9

Tobacco is an agricultural product processed from the leaves of plants in the genus *Nicotiana*. It can be consumed, used as a pesticide and, in the form of nicotine tartrate, used in some medicines. It is most commonly used as a drug, and is a valuable cash crop for countries such as Cuba, India, China, and the United States. Although not wanting to be bound by theory, tobacco is a name for any plant of the genus *Nicotiana* of the Solanaceae family (nightshade family) and for the product manufactured from the leaf and used in cigars and cigarettes, snuff, and pipe and chewing tobacco. Tobacco plants are also used in plant bioengineering, and some of the 60 species are grown as ornamentals. The chief commercial species, *N. tabacum*, is believed native to tropical America, like most *nicotiana* plants, but has been so long cultivated that it is no longer known in the wild. *N. rustica*, a mild-flavored, fast-burning species, was the tobacco originally raised in Virginia, but it is now grown chiefly in Turkey, India, and Russia. The alkaloid nicotine is the most characteristic constituent of tobacco and is responsible for its addictive nature. Tobacco was also utilized as a plant for expressing the MtNIP/LATD gene. More specifically, FIG. 25 shows a top view (Panel A) and side view (Panel B) of a side-by-side comparisons, wherein the tobacco plants transformed with the construct containing a constitutive promoter driving MtNIP/LATD (2510) are larger than tobacco plants transformed with the GUS gene (2520).

Example 10

The growth phenotype of the *Arabidopsis* plants was determined when the plants are treated to different nitrate conditions. Experiments that compare wild type and transgenic plants treated with various low nitrate concentrations of 100-200 μM $KNO_3$, indicate that the *Arabidopsis* plants constitutively expressing MtNIP/LATD are larger than control plants. Additionally, high nitrate concentration, 10 mM $KNO_3$, indicate that the control plants are comparable in size to the plants constitutively expressing MtNIP/LATD. Although not wanting to be bound by theory, these experiment indicate that plants constitutively expressing MtNIP/LATD will do better in nitrogen poor environments when compared to non-transgenic plants.

Although not wanting to be bound by theory, the differences in growth may be due to a cascade change in gene regulation. For example, comparison of gene expression/regulation using an Affymetrix gene chip analysis for the *Arabidopsis* plants constitutively expressing MtNIP/LATD grown at 100 μM $KNO_3$ compared to the same plants grown at 10 mM $KNO_3$ and found that the plants expressing MtNIP/LATD have about 35 mis-regulated genes. In contrast, non-transgenic control plants grown under similar conditions show over 1,000 mis-regulated genes using the Affymetrix gene chip analysis.

Although not wanting to be bound by theory, it is possible that an increase in production of nodules could be linked to the growth changes observed in wildtype plants and plants constitutively expressing MTNIP/LATD. More specifically, FIG. 26 shows the nodules (2601) in a *M. Truncatula* plant can be observed in several areas of the root system of the plant. FIG. 26 indicates at least three nodule areas including: A primary nodulation zone (2610); A Lateral Root Nodule Zone (2620); and a secondary nodulation Zone (2630).

*M. truncatula* plants that constitutively express MtNIP/LATD are able to produce more nodules per plant when compared to control plants. More specifically. FIG. 27 shows that transgenic plants grown in the absence of $KNO_3$ have about twice as many nodules when compared to non-transgenic plants (2710). In the presence of a low concentration of about 0.2 mM $KNO_3$, the transgenic plants still retain about twice the number of nodules when compared to a non-transgenic plant, wherein the number of nodules is about one-fifth less than transgenic plants grown with 0 mM $KNO_3$ (2720). In contrast, the increase in nodule number almost disappears when both plants are grown in higher concentrations (i.e. ~1.0 mM of $KNO_3$) (2730).

Although not wanting to be bound by theory, it is not known if the plants having more nodules actually fix more nitrogen. The nodules were counted at 15 days post-inoculation with *Sinorhizobium meliloti*. It has been observed upon close examination of the plants that the extra nodules are located the secondary nodulation zone, and on the lateral roots, areas that normally have fewer nodules under our growing conditions. More specifically, FIG. 28 compares the nodule number in the Primary zone when plants are grown in 0.0 mm, 0.20 mM; and 1.0 mM of $KNO_3$. The graph in FIG. 28 indicates that as the concentration of $KNO_3$ increases, the number of nodules in the primary zone of both the transgenic and non-transgenic plants decrease about 50%. Moreover, the number of nodules are almost equal when comparing transgenic plants to non-transgenic plants grown at higher concentrations of $KNO_3$. Additionally, it appears that the plants and the plant roots are still about the same size as control plants not expressing MtNIP/LATD.

Extra nodules located the secondary nodulation zone have been observed in the transgenic plants. Additionally, the secondary nodulation zone and lateral roots areas normally have fewer nodules under the specified growing conditions. More specifically, FIG. 29 compares the nodule number in the secondary nodulation zone when plants are grown in 0.0 mm, 0.20 mM; and 1.0 mM of $KNO_3$. The *M. truncatula* plants that constitutively express MtNIP/LATD are able to produce more nodules in the secondary zone when compared to control plants. More specifically, FIG. 29 shows that transgenic plants grown in the absence of $KNO_3$ have about twice as many nodules when compared to non-transgenic plants (2810). In the presence of a low concentration of about 0.2 mM $KNO_3$, the transgenic plants still retain about twice the number of nodules when compared to a non-transgenic plant, wherein the number of nodules is about one-fifth less than transgenic plants grown with 0 mM $KNO_3$ (2720). In contrast, the increase in nodule number almost disappears when both plants are grown in higher concentrations (i.e. ~1.0 mM of $KNO_3$) (2930).

An increased number of nodules located the lateral roots was observed in the transgenic plants. More specifically. FIG. 30 compares the nodule number in the lateral roots when plants are grown in 0.0 mm, 0.20 mM; and 1.0 mM of $KNO_3$. The *M. trancatula* plants that constitutively express MtNIP/LATD are able to produce and maintain more nodules in the lateral roots when compared to control plants. More specifically, FIG. 29 shows that transgenic plants grown in the absence of $KNO_3$ have about three as many nodules when compared to non-transgenic plants (2910). In the presence of a low concentration of about 0.2 mM $KNO_3$, the transgenic plants still retain about three times the number of nodules when compared to a non-transgenic plant (2920). In contrast with the other nodulation zones, the lateral roots maintain the three fold increase in nodules in the lateral roots even when both plants are grown in higher concentrations of $KNO_3$ (i.e. ~1.0 mM) (2930). However, the total number of nodes in the lateral roots is about 3-fold less when plants are grown in 1.0 mM $KNO_3$ compared to zero $KNO_3$.

Additionally, FIG. 31 shows that MtNIP/LATD overexpressing lines have more lateral roots in zero or low (0.2 mM $KNO_3$), but this difference disappears in the presence of 1 mM $KNO_3$.

REFERENCES CITED

The following references, to the extent that they provide exemplary procedural or other details supplementary to those set forth herein, are specifically incorporated herein by reference.

Abogadallah G M, Nada R M, Malinowski R, Quick P (2011) Overexpression of HARDY, an AP2/ERF gene from *Arabidopsis*, improves drought and salt tolerance by reducing transpiration and sodium uptake in transgenic *Trifolium alexandrinum* L. Planta 233: 1265-1276

Auriac M-C, Timmers A C J (2007) Nodulation studies in the model legume *Medicago truncatula*: Advantages of using the constitutive EF1 a promoter and limitations in detecting fluorescent reporter proteins in nodule tissues. *Molecular Plant Microbe Interactions* 20: 1040-1047

Bhatnagar-Mathur P, Vadez V, Sharma K K (2008) Transgenic approaches for abiotic stress tolerance in plants: retrospect and prospects. Plant Cell Reports 27: 411-424

Bright L. Liang Y, Mitchell D M, Harris J M (2005) LATD, a gene required for both nodule and root development. Molecular Plant-Microbe Interactions 18: 521-532 Gonzalez N, Beemster G T, Inze D (2009) David and Goliath: what can the tiny weed *Arabidopsis* teach us to improve biomass production in crops? *Current Opinion in Plant Biology* 12: 157-164

Fan X, Yan M, Tang Z, Feng H, Miller T, Shen Q, Xu G Engineering rice nitrate transporters to improve N use efficiency Flavell R (2005) Model plants, with special emphasis on *Arabidopsis thaliana*, and crop improvement. In R Tuberosa, R L Phillips, M Gale, eds. Proceedings of the International Congress In the Wake of the Double Helix: From the Green Revolution to the Gene Revolution, 27-31 May 2003, Bologna, Italy. Avenue Media, Bologna, Italy, pp 365-378

Gao S, Zhang H, Tian Y. Li F, Zhang Z. Lu X, Chen X, Huang R (2008) Expression of TERF1 in rice regulates expression of stress-responsive genes and enhances tolerance to drought and high-salinity. Plant Cell Rep. 27: 1787-1795

Gonzalez N, De Bodt S, Sulpice R, Jikumaru Y, Chae E, Dhondt S, Van Daele T, De Milde L, Weigel D, Kamiya Y, Stitt M, Beemster G T S, Inze D (2010) Increased leaf size: Different means to an end. *Plant Physiology* 153: 1261-1279

Ho C-H, Lin S-H, Hu H-C, Tsay Y-F (2009) CHL1 functions as a nitrate sensor in plants. *Cell* 138: 1184-1194

Huang N-C, Chiang C-S, Crawford N M, Tsay Y-F (1996) CHL1 encodes a component of the low-affinity nitrate uptake system in *Arabidopsis* and shows cell type-specific expression in roots. *Plant Cell* 8: 2183-2191

Hussain S S, Kayani M A, Amjad M (2011) Transcription factors as tools to engineer enhanced drought stress tolerance in plants. Biotechnology Progress 27: 297-306

Jeong J, Suh S, Guan C, Tsay Y-F. Moran N, Jae Oh C, An C-S, Demchenko K N, Pawlowski K, Lee Y (2004) A nodule-specific dicarboxylate transporter from alder is a member of the peptide transporter family. *Plant Physiology* 134: 969-978

Jin T, Chang Q, Li W, Yin D, Li Z, Wang D, Liu B, Liu L (2010) Stress-inducible expression of GmDREB1 conferred salt tolerance in transgenic alfalfa. Plant Cell Tissue Organ Cult 100: 219-227

Katayama H, Mori M, Kawamura Y, Tanaka T, Mori M, Hasegawa H (2009) Production and characterization of transgenic plants carrying a high-affinity nitrate transporter gene (OsNRT2.1) *Breeding Science* 59:237-243

Krizek B A (2009) Making bigger plants: key regulators of final organ size. *Current Opinion in Plant Biology* 12: 17-22

Krouk G, Lacombe B, Bielach A, Perrine-Walker F, Malinska K, Mounier E, Hoyerova K, Tillard P, Leon S, Ljung K, Zazimalova E, Benkova E, Nacry P, Gojon A (2010)

Nitrate-Regulated Auxin Transport by NRT1.1 Defines a Mechanism for Nutrient Sensing in Plants. *Developmental Cell* 18: 927-937

Liu K-H, Huang C-Y, Tsay Y-F (1999) CHL1 is a dual affinity nitrate transporter of *Arabidopsis* involved in multiple phases of nitrate uptake. *Plant Cell* 11

Manavalan L P, Guttikonda S K, Tran L S, Nguyen H T (2009) Physiological and molecular approaches to improve drought resistance in soybean. Plant and Cell Physiology 50: 1260-1276

NSF (2002) Beyond the Whole Genome Sequence. In. National Science Foundation, Arlington, Va. nsf.gov/pubs/2002/bio0202/model.htm Teillet A, Garcia J, de Billy F. Gherardi M, Huguet T, Barker D G, de Carvalho-Niebel F, Journet E-P (2008) api, a novel *Medicago truncatula* symbiotic mutant impaired in nodule primordium invasion. *Molecular Plant Microbe Interactions* 21: 535-546

Tsay Y-F, Chiu C-C, Tsai C-B, Ho C-H, Hsu P-K (2007) Nitrate transporters and peptide transporters. *FEBS Letters* 581 2290-2300

Tsay Y-F, Schroeder J I, Feldmann K A, Crawford N M (1993) The herbicide sensitivity gene CHL1 of *Arabidopsis* encodes a nitrate-inducible nitrate transporter. *Cell* 72: 705-713

Valente M A S, Faria J A Q A, Soares-Ramos J R L, Reis P A B, Pinheiro G L, Piovesan N D, Morais A T, Menezes C C, Cano M A O, Fietto L G, Loureiro M E, Aragão F J L, Fontes E P B (2009) The ER luminal binding protein (BiP) mediates an increase in drought tolerance in soybean and delays drought-induced leaf senescence in soybean and tobacco. Journal of Experimental Botany 60: 533-546

Veereshlingam H. Haynes J G, Sherrier D J, Penmetsa R V, Cook D R, Dickstein R (2004) nip, a symbiotic *Medicago truncatula* mutant that forms root nodules with aberrant infection threads and plant defense-like response. *Plant Physiol.* 136: 3692-3702

Wang R, Liu D, Crawford N M (1998) The *Arabidopsis* CHL protein plays a major role in high-affinity nitrate uptake. *Proc Natl Acad Sci USA* 95: 15134-15139

Wang R, Xing X, Wang Y, Tran A, Crawford N M (2009) A genetic screen for nitrate regulatory mutants captures the nitrate transporter gene NRT1.1. *Plant Physiology* 151: 72-478

Ware D, Stein L (2003) Comparison of genes among cereals. Current Opinion in Plant Biology 6: 121-127

Yendrek C R, Lee Y-C, Morris V, Liang Y. Pislariu C I, Burkart G, Meckfessel M H, Salehin M, Kessler H, Wessler H, Lloyd M. Lutton H, Teillet A, Sherrier D J, Journet E-P, Harris J M, Dickstein R (2010) A putative transporter is essential for integrating nutrient and hormone signaling with lateral root growth and nodule development in *Medicago truncatula*. The *Plant Journal* 62: 100-112

Zhang H, Liu W, Wan L, Li F, Dai L, Li D, Zhang Z, Huang R (2010) Functional analyses of ethylene response factor JERF3 with the aim of improving tolerance to drought and osmotic stress in transgenic rice. Transgenic Res 19: 809-818

Zhang J Z. Creelman R A, Zhu J-K (2004) Froml aboratory to field. Using information from *Arabidopsis* to engineer salt, cold, and drought tolerance in crops. Plant Physiology 135: 615-621

Zhang Z, Huang R (2010) Enhanced tolerance to freezing in tobacco and tomato overexpressing transcription factor TERF2, LeERF2 is modulated by ethylene biosynthesis. Plant Molecular Biology 73: 241-249

Zhang Z, Li F, Li D. Zhang H. Huang R (2010) Expression of ethylene response factor JERF1 in rice improves tolerance to drought. Planta 232: 765-774

LITERATURE CITED

Almagro A, Lin S H, Tsay Y-F (2008) Characterization of the *Arabidopsis* nitrate transporter NRT1.6 reveals a role of nitrate in early embryo development. Plant Cell: doi/10.1105/tpc.1107.056788

Barbier-Brygoo H. De Angeli A. Filleur S, Frachisse J-M, Gambale F, Thomine S, Wege S (2011) Anion channels/transporters in plants: From molecular bases to regulatory networks. Annu. Rev. Plant Biol. 62: 25-51

Bekki A, Trinchant J-C, Rigaud J (1987) Nitrogen fixation ($C_2H_2$ reduction) by *Medicago* nodules and bacteroids under sodium chloride stress. Physiol. Plant 71: 61-67

Benedito V A, Li H, Dai X, Wandrey M, He J, Kaundal R, Torres-Jerez I, Gomez S K, Harrison M J, Tang Y, Zhao P X, Udvardi M K (2010) Genomic inventory and transcriptional analysis of *Medicago truncatula* transporters. Plant Physiology 152: 1716-1730

Boisson-Dernier A, Chabaud M, Garcia F, Becard G, Rosenberg C, Barker D G (2001) *Agrobacterium rhizogenes*-transformed roots of *Medicago truncatula* for the study of nitrogen-fixing and endomycorrhizal symbiotic associations. Molecular Plant Microbe Interactions 14: 695-700

Boivin C, Camut S, Malpica C A, Truchet G, Rosenberg C (1990) *Rhizobium meliloti* genes encoding catabolism of trigonelline are induced under symbiotic conditions. Plant Cell 2: 1157-1170

Bright L, Liang Y, Mitchell D M, Harris J M (2005) LATD, a gene required for both nodule and root development. Molecular Plant-Microbe Interactions 18: 521-532

Clough S J, Bent A F (1998) Floral dip: a simplified method for *Agrobacterium*-mediated transformation of *Arabidopsis thaliana*. Plant Journal 16: 735-743

Correa-Aragunde N, Graziano M, Lamattina L (2004) Nitric oxide plays a central ole in determining lateral root development in tomato. Planta 218: 900-905

Crawford N M (1995) Nitrate: nutrient and signal for plant growth. Plant Cell 7: 859-868 del Giudice J, Cam Y. Damiani I, Fung-Chat F, Meilhoc E, Bruand C, Brouquisse R, Puppo A, Boscari A (2011) Nitric oxide is required for an optimal establishment of the *Medicago truncatula-Sinorhizobium meliloti* symbiosis. New Phytologist 191: 405 117

Doddema H. Hofstra J J, Feenstra W J (1978) Uptake of nitrate by mutants of *Arabidopsis thaliana*, disturbed in uptake or reduction of nitrate. Physiol. Plant 43: 343-350

Ehrhardt D W, Atkinson E M, Long S R (1992) Depolarization of alfalfa root hair membrane potential by *Rhizobium meliloti* Nod factors. Science 256 998-1000

Fan S-C, Lin C-S, Hsua P-K, Lin S-H, Tsay Y-F (2009) The *Arabidopsis* nitrate transporter NRT1.7, expressed in phloem, is responsible for source-to-sink remobilization of nitrate. The Plant Cell 21: 2750-2761

Fei H. Vessey J K (2008) Stimulation of nodulation in *Medicago truncatula* by low concentrations of ammonium: quantitative reverse transcription PCR analysis of selected genes. Physiologia Plantarum 135: 317-330

Gojon A, Krouk G, Perrine-Walker F, Laugier E (2011) Nitrate transceptor(s) in plants. Journal of Experimental Botany 62: 2299-2308

Harris J M, Dickstein R (2010) Control of root architecture and nodulation by the LATDAVIP transporter. Plant Signaling & Behavior 5: 1386-1390

Ho C-H, Lin S-H, Hu H-C, Tsay Y-F (2009) CHL1 functions as a nitrate sensor in plants. Cell 138: 1184-1194

Hofgen R, Willmitzer L (1988) Storage of competent cells for *Agrobacterium* transformation. Nucl. Acids Res. 16: 9877

Horchani F, Prevot M, Boscari A, Evangelisti E, Meilhoc E, Bruand C, Raymond P, Boncompagni E, Aschi-Smiti S, Puppo A, Brouquisse R (2011) Both plant and bacterial nitrate reductases contribute to nitric oxide production in *Medicago truncatula* nitrogen-fixing nodules. Plant Physiology 155: 1023-1036

Huang N-C, Chiang C-S, Crawford N M, Tsay Y-F (1996) CHL1 encodes a component of the low-affinity nitrate uptake system in *Arabidopsis* and shows cell type-specific expression in roots. Plant Cell 8: 2183-2191

Jeong J, Suh S, Guan C, Tsay Y-F, Moran N, Jae Oh C, An C-S, Demchenko K N, Pawlowski K, Lee Y (2004) A nodule-specific dicarboxylate transporter from alder is a member of the peptide transporter family. Plant Physiology 134: 969-978

Kanno Y. Hanada A, Chiba Y, Ichikawa T. Nakazawa M, Matsui M, Koshiba T, Kamiya Y. Seo M (2012) Identification of an abscisic acid transporter by functional screening using the receptor complex as a sensor. Proc Natl Acad Sci USA 109: 9653-9658

Kouchi H, Imaizumi-Anraku H, Hayashi M, Hakoyama T, Nakagawa T, Umehara Y, Suganuma N, Kawaguchi M (2010) How many peas in a pod? Legume genes responsible for mutualistic symbioses underground. Plant Cell Physiology 51: 1381-1397

Krieg P A, Melton D A (1984) Functional messenger RNAs are produced by SP6 in vitro transcription of cloned cDNAs. Nucl. Acids Res. 12: 7057-7070

Krouk G, Crawford N M, Coruzzi G M, Tsay Y F (2010) Nitrate signaling: adaptation to fluctuating environments. Current Opinion in Plant Biology 13: 266-273

Krouk G, Lacombe B, Bielach A, Perrine-Walker F, Malinska K, Mounier E, Hoyerova K, Tillard P, Leon S, Ljung K, Zazimalova E, Benkova E, Nacry P, Gojon A (2010) Nitrate-Regulated Auxin Transport by NRT1.1 Defines a Mechanism for Nutrient Sensing in Plants. Developmental Cell 18: 927-937

Li J-Y, Fu Y-L, Pike S M, Bao J, Tian W, Zhang Y, Chen C-Z, Zhang Y, Li H-M, Huang J, Li L-G, Schroeder J I, Gassmann W, Gong J-M (2010) The *Arabidopsis* nitrate transporter NRT1.8 functions in nitrate removal from the xylem sap and mediates cadmium tolerance. Plant Cell 22: 1633-1646

Liang Y, Harris J M (2005) Response of root branching to abscisic acid is correlated with nodule formation both in legumes and non-legumes. American Journal of Botany 92: 1675-1683

Liang Y, Mitchell D M, Harris J M (2007) Abscisic acid rescues the root meristem defects of the *Medicago truncatula* laid mutant. Developmental Biology 304 297-307

Lichtenthaler H K (1987) Chlorophylls and carotenoids: Pigments of photosynthetic biomembranes. Methods in Enzymology 148: 350-382

Lin S-H, Kuo H-F, Canivenc G, Lin C-S, Lepetit M, Hsu P-K, Tillard P. Lin H-L, Wang Y-Y, Tsai C-B, Gojon A, Tsay Y-F (2008) Mutation of the *Arabidopsis* NRT1.5 nitrate transporter causes defective root-to-shoot nitrate transport. Plant Cell 20: 2514-2528

Linkohr B I, Williamson L C, Fitter A H, Leyser H M O (2002) Nitrate and phosphate availability and distribution have different effects on root system architecture of *Arabidopsis*. Plant Journal 29: 751-760

Liu K-H, Tsay Y-F (2003) Switching between the two action modes of the dual-affinity nitrate transporter CHL1 by phosphorylation. EMBO Journal 22: 1005-1013

Liu K-H, Tsay Y-F (2003) Switching between the two action modes of the dual-affinity nitrate transporter CHL1 by phosphorylation. EMBO Journal 22: 1005-1013

Lullien V, Barker D G, de Lajudie P. Huguet T (1987) Plant gene expression in effective and ineffective root nodules of alfalfa (*Medicago saliva*). Plant Molecular Biology 9: 469-478

Meilhoc E, Boscari A, Bruand C, Puppo A, Brouquisse R (2011) Nitric oxide in legume-rhizobium symbiosis. Plant Science 181: 573-581

Miller A J, Fan X, Orsel M, Smith S J, Wells D M (2007) Nitrate transport and signalling. Journal of Experimental Botany 58: 2297-2306

Miranda M, Borisjuk L, Tewes A, Dietrich D, Rentsch D, Weber H, Wobus U (2003) Peptide and amino acid transporters are differentially regulated during seed development and germination in faba bean. Plant Physiology 132: 1950-1960

Morere-Le Paven M-C, Viau L, Hamon A, Vandecasteele C, Pellizzaro A, Bourdin C, Laffont C, Lapied B, Lepetit M, Frugier F, Legros C, Limami A M (2011) Characterization of a dual-affinity nitrate transporter MtNRT1.3 in the model legume *Medicago truncatula*. Journal of Experimental Botany 62: 5595-5605

Mortier V, Den Herder G, Whitford R, Van de Velde W, Rombauts S, D'haeseleer K, Holsters M, Goormachtig S (2010) CLE peptides control *Medicago truncatula* nodulation locally and systemically. Plant Physiology 153: 222-237

Munos S, Cazettes C, Fizames C, Gaymard F, Tillard P, Lepetit M, Lejay L, Gojon A (2004) Transcript profiling in the chl1-5 mutant of *Arabidopsis* reveals a role of the nitrate transporter NRT1.1 in the regulation of another nitrate transporter, NRT2.1. Plant Cell 16: 2433-2447

Oldroyd G E D, Downie J A (2008) Coordinating nodule morphogenesis with rhizobial infection in legumes. Annu. Rev. Plant Biol. 59 519-546

Penmetsa R V, Cook D R (1997) A legume ethylene-insensitive mutant hyperinfected by Its rhizobial symbiont. Science 275: 527-530

Pislariu C I, Dickstein R (2007) An IRE-like AGC Kinase Gene, MtIRE, has unique expression in the invasion zone of developing root nodules in *Medicago truncatula*. Plant Physiology 144: 682-694

Quandt H J, Puhler A, Broer I (1993) Transgenic root nodules of *Vicki hirsuta*: A fast and efficient system for the study of gene expression in indeterminate-type nodules. Molecular Plant-Microbe Interactions 6: 699-706

Remans T, Nacry P, Pervent M, Filleur S, Diatloff E, Mounier E, Tillard P, Forde B G, Gojon A (2006) The *Arabidopsis* NRT1.1 transporter participates in the signaling pathway triggering root colonization of nitrate-rich patches. Proc Natl Acad Sci USA 103: 19206-19211

Rosenberg C, Boistard P, Denarie J, Casse-Delbart F (1981) Genes controlling early and late functions in symbiosis are located on a megaplasmid in *Rhizobium meliloti*. Molecular and General Genetics 184: 326-333

Salazar C, Armenta J M, Cortes D F, Shulaev V (2012) Combination of an AccQ-Tag-Ultra Performance Liquid Chromatographic Method with Tandem Mass Spectrometry for the Analysis of Amino Acids. In MA Alterman, P Hunziker, eds, Amino Acid Analysis: Methods and Protocols, Methods in Molecular Biology, Vol 828. Humana Press, pp 13-28

Sato S, Nakamura Y, Kaneko T, Asamizu E, Kato T, Nakao M, Sasamoto S, Watanabe A, Ono A, Kawashima K, Fujishiro T, Katoh M, Kohara M, Kishida Y, Minami C, Nakayama S, Nakazaki N, Shimizu Y, Shinpo S, Takahashi C, Wada T, Yamada M, Ohmido N, Hayashi M, Fukui K, Baba T, Nakamichi T, Mori H, Tabata S (2008) Genome structure of the legume, *Lotus japonicus*. DNA Research 15: 227-239

Schmutz J, Cannon S B, Schlueter J, Ma J, Mitros T, Nelson W, Hyten D L, Song Q, Thelen J J, Cheng J, Xu D, Hellsten U, May G D, Yu Y, Sakurai T, Umezawa T, Bhattacharyya M K, Sandhu D, Valliyodan B, Lindquist E, Peto M, Grant D, Shu S, Goodstein D, Barry K, Futrell-Griggs M, Abernathy B, Du J, Tian Z, Zhu L. Gill N, Joshi T, Libault M, Sethuraman A, Zhang X-C, Shinozaki K, Nguyen H T, Wing R A, Cregan P, Specht J, Grimwood J, Rokhsar D, Stacey G, Shoemaker R C, Jackson S A (2010) Genome sequence of the palaeopolyploid soybean. Nature 463: 178-183

Segonzac C, Boyer J-C, Ipotesi E, Szponarski W, Tillard P, Touraine B, Sommerer N, Rossignol M, Gibrata R (2007) Nitrate efflux at the root plasma membrane: Identification of an *Arabidopsis* excretion transporter. Plant Cell 19: 3760-3777

Srivastava A C, Ganesan S, Ismail I O, Ayre B G (2008) Functional characterization of the *Arabidopsis* AtSUC2 sucrose/$H^+$ symporter by tissue-specific complementation reveals an essential role in phloem loading but not in long-distance transport. Plant Physiology 148: 200-211

Streeter J (1988) Inhibition of legume nodule formation and $N_2$ fixation by nitrate. CRC Critical Reviews in Plant Science 7: 1-23

Teillet A, Garcia J, de Billy F, Gherardi N I, Huguet T, Barker D G, de Carvalho-Niebel F. Journet E-P (2008) api, a novel *Medicago truncatula* symbiotic mutant impaired in nodule primordium invasion. Molecular Plant Microbe Interactions 21: 535-546

Tsay Y-F, Chiu C-C, Tsai C-B, Ho C-H, Hsu P-K (2007) Nitrate transporters and peptide transporters. FEBS Letters 581 2290-2300

Tsay Y-F, Schroeder J I, Feldmann K A, Crawford N M (1993) The herbicide sensitivity gene CHL1 of *Arabidopsis* encodes a nitrate-inducible nitrate transporter. Cell 72: 705-713

Udvardi M K, Day D A (1997) Metabolite transport across symbiotic membranes of legume nodules. Annual Review of Plant Physiology and Plant Molecular Biology 48: 493-523

Veereshlingam H, Haynes J G, Sherrier D J, Penmetsa R V, Cook D R, Dickstein R (2004) nip, a symbiotic *Medicago truncatula* mutant that forms root nodules with aberrant infection threads and plant defense-like response. Plant Physiol. 136: 3692-3702

Walch-Liu P, Forde B G (2008) Nitrate signalling mediated by the NRT1.1 nitrate transporter antagonises L-glutamate-induced changes in root architecture. Plant Journal doi: 10.1111/j.1365-313X.2008.03443.x Walch-Liu P, Liu L-H, Remans T, Tester M, Forde B G (2006) Evidence that L-glutamate can act as an exogenous signal to modulate root growth and branching in *Arabidopsis thaliana*. Plant Cell Physiol. 47: 1045-1057

Wang R, Xing X, Wang Y, Tran A, Crawford N M (2009) A genetic screen for nitrate regulatory mutants captures the nitrate transporter gene NRT1.1. Plant Physiology 151: 472-478

Wang Y-Y, Tsay Y-F (2011) *Arabidopsis* nitrate transporter NRT1.9 is important in phloem nitrate transport. Plant Cell 23: 1945-1957

Waterworth W M, Bray C M (2006) Enigma variations for peptides and their transporters in higher plants. Annals of Botany 98: 1-8

White J, Prell J, James E K, Poole P (2007) Nutrient sharing between symbionts. Plant Physiology 144: 604-614

Wilkinson J Q, Crawford N M (1991) Identification of the *Arabidopsis* CHL3 gene as the nitrate reductase structural gene NIA2. Plant Cell 3: 461-471

Xu G, Fan X, Miller A J (2012) Plant nitrogen assimilation and use efficiency. Annual Review Plant Biology 63: 5.1-5.30

Yamashita T, Shimada S, Guo W, Sato K, Kohmura E, Hayakawa T, Takagi T, Tohyama M (1997) Cloning and functional expression of a brain peptide/histidine transporter. Journal of Biological Chemistry 272: 10205-10211

Yendrek C R, Lee Y-C, Morris V, Liang Y, Pislariu C I, Burkart G, Meckfessel M H, Salehin M, Kessler H, Wessler H, Lloyd M, Lutton H, Teillet A, Sherrier D J, Journet E-P, Harris J M, Dickstein R (2010) A putative transporter is essential for integrating nutrient and hormone signaling with lateral root growth and nodule development in *Medicago truncatula*. The Plant Journal 62: 100-112

Yokoyama T, Kodama N, Aoshima H, Izu H. Matsushita K, Yamada M (2001) Cloning of a cDNA for a constitutive NRT1 transporter from soybean and comparison of gene expression of soybean NRT1 transporters. Biochimica et Biophysica Acta 1518: 79-86

Young N D, Debelle F, Oldroyd G E D, Geurts R, Cannon S B, Udvardi M K, Benedito V A, Mayer K F X, Gouzy J, Schoof H, Van de Peer Y, Proost S, Cook D R, Meyers B C, Spannagl M, Cheung F, De Mita S, Krishnakumar V, Gundlach H, Zhou S, Mudge J, Bharti A K, Murray J D, Naoumkina M A, Rosen B, et al. (2011) The *Medicago* genome provides insight into the evolution of rhizobial symbioses. Nature 480: 520-524

Zhang H, Jennings A J, Forde B G (2000) Regulation of *Arabidopsis* root development by nitrate availability. Journal of Experimental Botany 51: 51-59

Zhao X, Huang J, Yu H, Wang L, Xie W (2010) Genomic survey, characterization and expression profile analysis of the peptide transporter family in rice (*Oryza saliva* L.). BMC Plant Biology 10 92

Zhou J-J, Theodoulou F L, Muldini I, Ingemarssoni B, Miller A J (1998) Cloning and functional characterization of a *Brassica napus* transporter that is able to transport nitrate and histidine. Journal of Biological Chemistry 273: 12017-12023

Zifarelli G, Pusch M (2010) CLC transport proteins in plants. FEBS Letters 584: 2122-2127

What is claimed:

1. A transgenic plant, or parts thereof, with increased biomass compared to a non-transformed plant of the same variety, or parts thereof wherein substantially all cells of the plant have been transformed with a construct comprising a heterologous, constitutive promoter operably linked to a nucleic acid encoding a protein comprising SEQ ID NO:8.

2. A seed of the transgenic plant, or parts thereof, of claim 1, wherein the seed comprises the construct.

3. The transgenic plant, or parts thereof, of claim 1, wherein the transgenic plant is a transformed *Arabidopsis thaliana* and wherein the parts comprise the construct.

4. A seed of the transgenic plant, or parts thereof, of claim 3, wherein the seed comprises the construct.

5. The transgenic plant, or parts thereof, of claim 1, wherein the transgenic plant is a transformed *Medicago truncatula* and wherein the parts comprise the construct.

6. A seed of the transgenic plant, or parts thereof, of claim 5, wherein the seed comprises the construct.

7. The transgenic plant, or parts thereof, of claim 1, wherein the transgenic plant is a transformed tobacco plant and wherein the parts comprise the construct.

8. A seed of the transgenic plant, or parts thereof, of claim 7, wherein the seed or parts comprise the construct.

9. A method of producing a transgenic plant, said method comprising: transforming substantially all cells in a plant with a construct comprising a heterologous, constitutive promoter operably linked to a nucleic acid encoding a protein comprising SEQ ID NO:8.

10. The transgenic plant produced by the method of claim 9.

11. The method of claim 9, wherein the plant is *Arabidopsis thaliana.*

12. A progeny of the transgenic plant produced by the method of claim 9, wherein the progeny comprises the construct.

13. The method of claim 9, wherein the plant is *M. truncatula.*

14. The method of claim 9, wherein the plant is a tobacco plant.

15. A method for generating transgenic seeds for plants having an increased biomass, comprising the step of:

(a) multiplying plant cells that contain at least one genetic transformation event of interest and which are capable of regeneration; wherein the genetic transformation event comprises a promoter nucleotide sequence that is capable of initiating transcription in a constitutive manner of an operably linked heterologous nucleic acid sequence comprising a nucleic acid sequence encoding a protein having a sequence of SEQ ID NO: 8 into said plant cells;

(b) selecting the plant cells that comprise at least one genetic transformation event of interest;

(c) regenerating a whole transgenic plant, or parts thereof, termed primary transformants, or $T_0$ plants, from said plant cells;

(d) pollinating said primary transformants with non-transgenic pollen;

(e) harvesting the seeds obtained, termed $T_1$, which have integrated at least one transgene of interest;

(f) sowing said transgenic $T_1$ seeds and pollinating the plants which result therefrom, either by self-pollination or by free pollination; and (g) harvesting the $T_2$ seeds.

16. The method of claim 15, wherein the plant cells are *Arabidopsis thaliana* plant cells, *Medicago truncatula* plant cells or tobacco plant cells.

17. An isolated transformation vector construct having a heterologous, constitutive promoter region operably linked to an expression region having at least 95% homology with SeqID No.: 23, SeqID No.: 24, or SeqID No.: 25.

18. A transgenic plant, or parts thereof, comprising a construct comprising a heterologous, constitutive promoter operably linked to a nucleic acid encoding a protein comprising SEQ ID NO:2 or SEQ ID NO:8, wherein the parts comprise the construct.

19. The transgenic plant, or parts thereof, of claim 18, wherein the plant cells are *Arabidopsis thaliana* plant cells or a *M. truncatula* plant cells.

20. The transgenic plant, or parts thereof, of claim 18, wherein the plant cells are tobacco plant cells.

21. A seed of the transgenic plant of claim 18, wherein the seed comprises the construct.

* * * * *

SEQUENCE LISTING

<160> NUMBER OF SEQ ID NOS: 29

<210> SEQ ID NO 1

-continued

<211> LENGTH: 1776
<212> TYPE: DNA
<213> ORGANISM: M. Truncatula

<400> SEQUENCE: 1

```
atggagtaca caaacagtga tgatgctaca aatgaaaaac tcattgaaaa tggcagctct     60
tcatcatctt ctcaacccag aaagggtggt ttaagaacca tgccctttat catagtgaat    120
gagtgtcttg agaaagtggc aagttatgga ataatgccaa acatgatatt atacttgagg    180
gatgattata acatgcctat tgctaaggct agttatgttc tttctacttg gtctgctatg    240
tccaatgttt tgtccatctt tggtgctttt ctctctgatt cttacttggg tcgcttcaat    300
gtcatcacta ttggctcctt ttctagcctt cttggtttaa ccgttttgtg gttaactgcc    360
atgatcccgg tgctaaaacc tacctgtgca tcactctttg aaatctgtaa ttctgctact    420
tcatcccaac aagcagttct gttcctttcc ttaggattaa tttcaattgg agctggttgt    480
gttagacctt gttccatagc ctttggagca gagcaattga ctattaaggg aaattctggt    540
gatgggaatg gcaggatctt ggatagttac tttaattggt attatacctc aatttcagtt    600
tcaaccatta tcgcgttgag tgtgattgct tacattcaag aaaaccttgg atggaaaatt    660
gggtttggag tacctgctgt gctaatgctc gtatcggtca tcagtttcat tattggttca    720
ccgttatatg tcaaagtgaa gccaagtgaa agcttactca ctaattttgc aagagtagtt    780
gtggtggcaa ccaagaacag aaaacttagt cttcctgatc acgactctga tcgttactgt    840
caaggtcatg attcaaagct gaaggttcct accgatagcc ttaggttttt gaacaaagct    900
tgcgtaataa gaaatcctga gacagatctt aatcgagatg ggtcaatttc aaatccgtgg    960
aacctatgca caatagaaca ggtggagtca ctgaagtctt tgctcagagt cattcctatg   1020
tggtcaacgg gaatctttat gatggcgact cagagttcat ttctactctt tcaagccaaa   1080
actttgaacc gaacgttatt cggcaatttc aattttcctg caggatcgtt caatcttatc   1140
ttgatattca ccttaacaat agtaattcct ttatatgacc gtgtaggagt acctctacta   1200
gctaaatacg caggccggcc tagaggattc agttttaaag tccgcatcgg gataggaatg   1260
ctgtttgcaa ttgtagctaa agcagtagca gctattgttg aaacggtgag acgaaatgca   1320
gcgattgaac aagggtttga ggaccaacct aatgctgaaa ttaacatgtc ggctttatgg   1380
cttgctccag agtttatttt gtttggattc gccgaagctt tcacaccagt tggactggtt   1440
gagtttttct actgtttttt ccctaagagt atgtctagtt ttgcaatggc tatgttcaca   1500
ttgggactag cttgttctga cgtagtttca ggtgtgcttg tgagcattgt ggacacggtc   1560
actagtattg gagggaatga gagctggtta tcgactaaca tcaatagggg acatttgaat   1620
tactactacg ggctactcac tttcttaggc attcttaact acttctatta tcttgttatt   1680
tgttgggctt atggacccat acagggagag aaacatgaag attcggccag aaagaaagac   1740
gataaatttg gttacaggga gttgcctact tcatag                            1776
```

<210> SEQ ID NO 2
<211> LENGTH: 591
<212> TYPE: PRT
<213> ORGANISM: M. Truncatula

<400> SEQUENCE: 2

```
Met Glu Tyr Thr Asn Ser Asp Asp Ala Thr Asn Glu Lys Leu Ile Glu
1               5                   10                  15

Asn Gly Ser Ser Ser Ser Ser Ser Gln Pro Arg Lys Gly Gly Leu Arg
            20                  25                  30
```

-continued

```
Thr Met Pro Phe Ile Ile Val Asn Glu Cys Leu Glu Lys Val Ala Ser
        35                  40                  45

Tyr Gly Ile Met Pro Asn Met Ile Leu Tyr Leu Arg Asp Asp Tyr Asn
    50                  55                  60

Met Pro Ile Ala Lys Ala Ser Tyr Val Leu Ser Thr Trp Ser Ala Met
65                  70                  75                  80

Ser Asn Val Leu Ser Ile Phe Gly Ala Phe Leu Ser Asp Ser Tyr Leu
                85                  90                  95

Gly Arg Phe Asn Val Ile Thr Ile Gly Ser Phe Ser Ser Leu Leu Gly
            100                 105                 110

Leu Thr Val Leu Trp Leu Thr Ala Met Ile Pro Val Leu Lys Pro Thr
        115                 120                 125

Cys Ala Ser Leu Phe Glu Ile Cys Asn Ser Ala Thr Ser Ser Gln Gln
    130                 135                 140

Ala Val Leu Phe Leu Ser Leu Gly Leu Ile Ser Ile Gly Ala Gly Cys
145                 150                 155                 160

Val Arg Pro Cys Ser Ile Ala Phe Gly Ala Glu Gln Leu Thr Ile Lys
                165                 170                 175

Gly Asn Ser Gly Asp Gly Asn Gly Arg Ile Leu Asp Ser Tyr Phe Asn
            180                 185                 190

Trp Tyr Tyr Thr Ser Ile Ser Val Ser Thr Ile Ile Ala Leu Ser Val
        195                 200                 205

Ile Ala Tyr Ile Gln Glu Asn Leu Gly Trp Lys Ile Gly Phe Gly Val
    210                 215                 220

Pro Ala Val Leu Met Leu Val Ser Val Ile Ser Phe Ile Ile Gly Ser
225                 230                 235                 240

Pro Leu Tyr Val Lys Val Lys Pro Ser Glu Ser Leu Leu Thr Asn Phe
                245                 250                 255

Ala Arg Val Val Val Val Ala Thr Lys Asn Arg Lys Leu Ser Leu Pro
            260                 265                 270

Asp His Asp Ser Asp Arg Tyr Cys Gln Gly His Asp Ser Lys Leu Lys
        275                 280                 285

Val Pro Thr Asp Ser Leu Arg Phe Leu Asn Lys Ala Cys Val Ile Arg
    290                 295                 300

Asn Pro Glu Thr Asp Leu Asn Arg Asp Gly Ser Ile Ser Asn Pro Trp
305                 310                 315                 320

Asn Leu Cys Thr Ile Glu Gln Val Glu Ser Leu Lys Ser Leu Leu Arg
                325                 330                 335

Val Ile Pro Met Trp Ser Thr Gly Ile Phe Met Met Ala Thr Gln Ser
            340                 345                 350

Ser Phe Ser Thr Leu Gln Ala Lys Thr Leu Asn Arg Thr Leu Phe Gly
        355                 360                 365

Asn Phe Asn Phe Pro Ala Gly Ser Phe Asn Leu Ile Leu Ile Phe Thr
    370                 375                 380

Leu Thr Ile Val Ile Pro Leu Tyr Asp Arg Val Gly Val Pro Leu Leu
385                 390                 395                 400

Ala Lys Tyr Ala Gly Arg Pro Arg Gly Phe Ser Phe Lys Val Arg Ile
                405                 410                 415

Gly Ile Gly Met Leu Phe Ala Ile Val Ala Lys Ala Val Ala Ala Ile
            420                 425                 430

Val Glu Thr Val Arg Arg Asn Ala Ala Ile Glu Gln Gly Phe Glu Asp
        435                 440                 445
```

-continued

```
Gln Pro Asn Ala Glu Ile Asn Met Ser Ala Leu Trp Leu Ala Pro Glu
    450                 455                 460

Phe Ile Leu Phe Gly Phe Ala Glu Ala Phe Thr Pro Val Gly Leu Val
465                 470                 475                 480

Glu Phe Phe Tyr Cys Phe Phe Pro Lys Ser Met Ser Ser Phe Ala Met
                485                 490                 495

Ala Met Phe Thr Leu Gly Leu Ala Cys Ser Asp Val Val Ser Gly Val
            500                 505                 510

Leu Val Ser Ile Val Asp Thr Val Thr Ser Ile Gly Gly Asn Glu Ser
        515                 520                 525

Trp Leu Ser Thr Asn Ile Asn Arg Gly His Leu Asn Tyr Tyr Tyr Gly
    530                 535                 540

Leu Leu Thr Phe Leu Gly Ile Leu Asn Tyr Phe Tyr Tyr Leu Val Ile
545                 550                 555                 560

Cys Trp Ala Tyr Gly Pro Ile Gln Gly Glu Lys His Glu Asp Ser Ala
                565                 570                 575

Arg Lys Lys Asp Asp Lys Phe Gly Tyr Arg Glu Leu Pro Thr Ser
            580                 585                 590
```

<210> SEQ ID NO 3
<211> LENGTH: 1636
<212> TYPE: DNA
<213> ORGANISM: M. Truncatula

<400> SEQUENCE: 3

```
aagttatgga ataatgccaa acatgatatt atacttgagg gatgattata acatgcctat     60

tgctaaggct agttatgttc tttctacttg gtctgctatg tccaatgttt tgtccatctt    120

tggtgctttt ctctctgatt cttacttggg tcgcttcaat gtcatcacta ttggctcctt    180

ttctagcctt cttggtttaa ccgttttgtg gttaactgcc atgatcccgg tgctaaaacc    240

tacctgtgca tcactctttg aaatctgtaa ttctgctact tcatcccaac aagcagttct    300

gttcctttcc ttaggattaa tttcaattgg agctggttgt gttagacctt gttccatagc    360

ctttggagca gagcaattga ctattaaggg aaattctggt gatgggaatg gcaggatctt    420

ggatagttac tttaattggt attatacctc aatttcagtt tcaaccatta tcgcgttgag    480

tgtgattgct tacattcaag aaaaccttgg atggaaaatt gggtttggag tacctgctgt    540

gctaatgctc gtatcggtca tcagtttcat tattggttca ccgttatatg tcaaagtgaa    600

gccaagtgaa agcttactca ctaattttgc aagagtagtt gtggtggcaa ccaagaacag    660

aaaacttagt cttcctgatc acgactctga tcgttactgt caaggtcatg attcaaagct    720

gaaggttcct accgatagcc ttaggttttt gaacaaagct tgcgtaataa gaaatcctga    780

gacagatctt aatcgagatg ggtcaatttc aaatccgtgg aacctatgca caatagaaca    840

ggtggagtca ctgaagtctt tgctcagagt cattcctatg tggtcaacgg gaatctttat    900

gatggcgact cagagttcat ttctactctt tcaagccaaa actttgaacc gaacgttatt    960

cggcaatttc aattttcctg caggatcgtt caatcttatc ttgatattca ccttaacaat   1020

agtaattcct ttatatgacc gtgtaggagt acctctacta gctaaatacg caggccggcc   1080

tagaggattc agttttaaag tccgcatcgg gataggaatg ctgtttgcaa ttgtagctaa   1140

agcagtagca gctattgttg aaacggtgag acgaaatgca gcgattgaac aagggtttga   1200

ggaccaacct aatgctgaaa ttaacatgtc ggctttatgg cttgctccag agtttatttt   1260

gtttggattc gccgaagctt tcacaccagt tggactggtt gagtttttct actgtttttt   1320
```

-continued

```
ccctaagagt atgtctagtt ttgcaatggt tatgttcaca ttgggactag cttgttctga   1380

cgtagtttca ggtgtgcttg tgagcattgt ggacacggtc actagtattg gagggaatga   1440

gagctggtta tcgactaaca tcaatagggg acatttgaat tactactacg ggctactcac   1500

tttcttaggc attcttaact acttctatta tcttgttatt tgttgggctt atggacccat   1560

acagggagag aaacatgaag attcggccag aaagaaagac gataaatttg gttacaggga   1620

gttgcctact tcatag                                                   1636


<210> SEQ ID NO 4
<211> LENGTH: 591
<212> TYPE: PRT
<213> ORGANISM: M. Truncatula

<400> SEQUENCE: 4

Met Glu Tyr Thr Asn Ser Asp Asp Ala Thr Asn Glu Lys Leu Ile Glu
1               5                   10                  15

Asn Gly Ser Ser Ser Ser Ser Ser Gln Pro Arg Lys Gly Gly Leu Arg
            20                  25                  30

Thr Met Pro Phe Ile Ile Val Asn Glu Cys Leu Glu Lys Val Ala Ser
        35                  40                  45

Tyr Gly Ile Met Pro Asn Met Ile Leu Tyr Leu Arg Asp Asp Tyr Asn
    50                  55                  60

Met Pro Ile Ala Lys Ala Ser Tyr Val Leu Ser Thr Trp Ser Ala Met
65                  70                  75                  80

Ser Asn Val Leu Ser Ile Phe Gly Ala Phe Leu Ser Asp Ser Tyr Leu
                85                  90                  95

Gly Arg Phe Asn Val Ile Thr Ile Gly Ser Phe Ser Ser Leu Leu Gly
            100                 105                 110

Leu Thr Val Leu Trp Leu Thr Ala Met Ile Pro Val Leu Lys Pro Thr
        115                 120                 125

Cys Ala Ser Leu Phe Glu Ile Cys Asn Ser Ala Thr Ser Ser Gln Gln
    130                 135                 140

Ala Val Leu Phe Leu Ser Leu Gly Leu Ile Ser Ile Gly Ala Gly Cys
145                 150                 155                 160

Val Arg Pro Cys Ser Ile Ala Phe Gly Ala Glu Gln Leu Thr Ile Lys
                165                 170                 175

Gly Asn Ser Gly Asp Gly Asn Gly Arg Ile Leu Asp Ser Tyr Phe Asn
            180                 185                 190

Trp Tyr Tyr Thr Ser Ile Ser Val Ser Thr Ile Ile Ala Leu Ser Val
        195                 200                 205

Ile Ala Tyr Ile Gln Glu Asn Leu Gly Trp Lys Ile Gly Phe Gly Val
    210                 215                 220

Pro Ala Val Leu Met Leu Val Ser Val Ile Ser Phe Ile Ile Gly Ser
225                 230                 235                 240

Pro Leu Tyr Val Lys Val Lys Pro Ser Glu Ser Leu Leu Thr Asn Phe
                245                 250                 255

Ala Arg Val Val Val Val Ala Thr Lys Asn Arg Lys Leu Ser Leu Pro
            260                 265                 270

Asp His Asp Ser Asp Arg Tyr Cys Gln Gly His Asp Ser Lys Leu Lys
        275                 280                 285

Val Pro Thr Asp Ser Leu Arg Phe Leu Asn Lys Ala Cys Val Ile Arg
    290                 295                 300

Asn Pro Glu Thr Asp Leu Asn Arg Asp Gly Ser Ile Ser Asn Pro Trp
305                 310                 315                 320
```

-continued

```
Asn Leu Cys Thr Ile Glu Gln Val Glu Ser Leu Lys Ser Leu Leu Arg
                325                 330                 335

Val Ile Pro Met Trp Ser Thr Gly Ile Phe Met Met Ala Thr Gln Ser
            340                 345                 350

Ser Phe Ser Thr Leu Gln Ala Lys Thr Leu Asn Arg Thr Leu Phe Gly
        355                 360                 365

Asn Phe Asn Phe Pro Ala Gly Ser Phe Asn Leu Ile Leu Ile Phe Thr
    370                 375                 380

Leu Thr Ile Val Ile Pro Leu Tyr Asp Arg Val Gly Val Pro Leu Leu
385                 390                 395                 400

Ala Lys Tyr Ala Gly Arg Pro Arg Gly Phe Ser Phe Lys Val Arg Ile
                405                 410                 415

Gly Ile Gly Met Leu Phe Ala Ile Val Ala Lys Ala Val Ala Ala Ile
            420                 425                 430

Val Glu Thr Val Arg Arg Asn Ala Ala Ile Glu Gln Gly Phe Glu Asp
        435                 440                 445

Gln Pro Asn Ala Glu Ile Asn Met Ser Ala Leu Trp Leu Ala Pro Glu
    450                 455                 460

Phe Ile Leu Phe Gly Phe Ala Glu Ala Phe Thr Pro Val Gly Leu Val
465                 470                 475                 480

Glu Phe Phe Tyr Cys Phe Phe Pro Lys Ser Met Ser Ser Phe Ala Met
                485                 490                 495

Val Met Phe Thr Leu Gly Leu Ala Cys Ser Asp Val Val Ser Gly Val
            500                 505                 510

Leu Val Ser Ile Val Asp Thr Val Thr Ser Ile Gly Gly Asn Glu Ser
        515                 520                 525

Trp Leu Ser Thr Asn Ile Asn Arg Gly His Leu Asn Tyr Tyr Tyr Gly
    530                 535                 540

Leu Leu Thr Phe Leu Gly Ile Leu Asn Tyr Phe Tyr Tyr Leu Val Ile
545                 550                 555                 560

Cys Trp Ala Tyr Gly Pro Ile Gln Gly Glu Lys His Glu Asp Ser Ala
                565                 570                 575

Arg Lys Lys Asp Asp Lys Phe Gly Tyr Arg Glu Leu Pro Thr Ser
            580                 585                 590


<210> SEQ ID NO 5
<211> LENGTH: 1776
<212> TYPE: DNA
<213> ORGANISM: M. Truncatula

<400> SEQUENCE: 5

atggagtaca caaacagtga tgatgctaca aatgaaaaac tcattgaaaa tggcagctct      60

tcatcatctt ctcaacccag aaagggtggt ttaagaacca tgccctttat catagtgaat     120

gagtgtcttg agaaagtggc aagttatgga ataatgccaa acatgatatt atacttgagg     180

gatgattata acatgcctat tgctaaggct agttatgttc tttctacttg gtctgctatg     240

tccaatgttt tgtccatctt tggtgctttt ctctctgatt cttacttggg tcgcttcaat     300

gtcatcacta ttggctcctt ttctagcctt cttggtttaa ccgttttgtg gttaactgcc     360

atgatcccgg tgctaaaacc tacctgtgca tcactctttg aaatctgtaa ttctgctact     420

tcatcccaac aagcagttct gttcctttcc ttaggattaa tttcaattgg agctggttgt     480

gttagacctt gttccatagc ctttggagca gagcaattga ctattaaggg aaattctggt     540

gatgggaatg gcaggatctt ggatagttac tttaattggt attatacctc aatttcagtt     600
```

-continued

```
tcaaccatta tcgcgttgag tgtgattgct tacattcaag aaaaccttgg atggaaaatt    660

gggtttggag tacctgctgt gctaatgctc gtatcggtca tcagtttcat tattggttca    720

ccgttatatg tcaaagtgaa gccaagtgaa agcttactca ctaattttgc aagagtagtt    780

gtggtggcaa ccaagaacag aaaacttagt cttcctgatc acgactctga tcgttactgt    840

caaggtcatg attcaaagct gaaggttcct accgatagcc ttaggttttt gaacaaagct    900

tgcgtaataa gaaatcctga gacagatctt aatcgagatg ggtcaatttc aaatccgtgg    960

aacctatgca caatagaaca ggtggagtca ctgaagtctt tgctcagagt cattcctatg   1020

tgatcaacgg gaatctttat gatggcgact cagagttcat tttctactct tcaagccaaa   1080

actttgaacc gaacgttatt cggcaatttc aattttcctg caggatcgtt caatcttatc   1140

ttgatattca ccttaacaat agtaattcct ttatatgacc gtgtaggagt acctctacta   1200

gctaaatacg caggccggcc tagaggattc agttttaaag tccgcatcgg gataggaatg   1260

ctgtttgcaa ttgtagctaa agcagtagca gctattgttg aaacggtgag acgaaatgca   1320

gcgattgaac aagggtttga ggaccaacct aatgctgaaa ttaacatgtc ggctttatgg   1380

cttgctccag agtttatttt gtttggattc gccgaagctt tcacaccagt tggactggtt   1440

gagtttttct actgtttttt ccctaagagt atgtctagtt ttgcaatggc tatgttcaca   1500

ttgggactag cttgttctga cgtagtttca ggtgtgcttg tgagcattgt ggacacggtc   1560

actagtattg gagggaatga gagctggtta tcgactaaca tcaatagggg acatttgaat   1620

tactactacg ggctactcac tttcttaggc attcttaact acttctatta tcttgttatt   1680

tgttgggctt atggacccat acagggagag aaacatgaag attcggccag aaagaaagac   1740

gataaatttg gttacaggga gttgcctact tcatag                             1776
```

```
<210> SEQ ID NO 6
<211> LENGTH: 590
<212> TYPE: PRT
<213> ORGANISM: M. Truncatula

<400> SEQUENCE: 6

Met Glu Tyr Thr Asn Ser Asp Asp Ala Thr Asn Glu Lys Leu Ile Glu
1               5                   10                  15

Asn Gly Ser Ser Ser Ser Ser Ser Gln Pro Arg Lys Gly Gly Leu Arg
            20                  25                  30

Thr Met Pro Phe Ile Ile Val Asn Glu Cys Leu Glu Lys Val Ala Ser
        35                  40                  45

Tyr Gly Ile Met Pro Asn Met Ile Leu Tyr Leu Arg Asp Asp Tyr Asn
    50                  55                  60

Met Pro Ile Ala Lys Ala Ser Tyr Val Leu Ser Thr Trp Ser Ala Met
65                  70                  75                  80

Ser Asn Val Leu Ser Ile Phe Gly Ala Phe Leu Ser Asp Ser Tyr Leu
                85                  90                  95

Gly Arg Phe Asn Val Ile Thr Ile Gly Ser Phe Ser Ser Leu Leu Gly
            100                 105                 110

Leu Thr Val Leu Trp Leu Thr Ala Met Ile Pro Val Leu Lys Pro Thr
        115                 120                 125

Cys Ala Ser Leu Phe Glu Ile Cys Asn Ser Ala Thr Ser Ser Gln Gln
    130                 135                 140

Ala Val Leu Phe Leu Ser Leu Gly Leu Ile Ser Ile Gly Ala Gly Cys
145                 150                 155                 160
```

-continued

```
Val Arg Pro Cys Ser Ile Ala Phe Gly Ala Glu Gln Leu Thr Ile Lys
                165                 170                 175

Gly Asn Ser Gly Asp Gly Asn Gly Arg Ile Leu Asp Ser Tyr Phe Asn
            180                 185                 190

Trp Tyr Tyr Thr Ser Ile Ser Val Ser Thr Ile Ile Ala Leu Ser Val
        195                 200                 205

Ile Ala Tyr Ile Gln Glu Asn Leu Gly Trp Lys Ile Gly Phe Gly Val
    210                 215                 220

Pro Ala Val Leu Met Leu Val Ser Val Ile Ser Phe Ile Ile Gly Ser
225                 230                 235                 240

Pro Leu Tyr Val Lys Val Lys Pro Ser Glu Ser Leu Leu Thr Asn Phe
                245                 250                 255

Ala Arg Val Val Val Val Ala Thr Lys Asn Arg Lys Leu Ser Leu Pro
            260                 265                 270

Asp His Asp Ser Asp Arg Tyr Cys Gln Gly His Asp Ser Lys Leu Lys
        275                 280                 285

Val Pro Thr Asp Ser Leu Arg Phe Leu Asn Lys Ala Cys Val Ile Arg
    290                 295                 300

Asn Pro Glu Thr Asp Leu Asn Arg Asp Gly Ser Ile Ser Asn Pro Trp
305                 310                 315                 320

Asn Leu Cys Thr Ile Glu Gln Val Glu Ser Leu Lys Ser Leu Leu Arg
                325                 330                 335

Val Ile Pro Met Ser Thr Gly Ile Phe Met Met Ala Thr Gln Ser Ser
            340                 345                 350

Phe Ser Thr Leu Gln Ala Lys Thr Leu Asn Arg Thr Leu Phe Gly Asn
        355                 360                 365

Phe Asn Phe Pro Ala Gly Ser Phe Asn Leu Ile Leu Ile Phe Thr Leu
    370                 375                 380

Thr Ile Val Ile Pro Leu Tyr Asp Arg Val Gly Val Pro Leu Leu Ala
385                 390                 395                 400

Lys Tyr Ala Gly Arg Pro Arg Gly Phe Ser Phe Lys Val Arg Ile Gly
                405                 410                 415

Ile Gly Met Leu Phe Ala Ile Val Ala Lys Ala Val Ala Ala Ile Val
            420                 425                 430

Glu Thr Val Arg Arg Asn Ala Ala Ile Glu Gln Gly Phe Glu Asp Gln
        435                 440                 445

Pro Asn Ala Glu Ile Asn Met Ser Ala Leu Trp Leu Ala Pro Glu Phe
    450                 455                 460

Ile Leu Phe Gly Phe Ala Glu Ala Phe Thr Pro Val Gly Leu Val Glu
465                 470                 475                 480

Phe Phe Tyr Cys Phe Phe Pro Lys Ser Met Ser Ser Phe Ala Met Ala
                485                 490                 495

Met Phe Thr Leu Gly Leu Ala Cys Ser Asp Val Val Ser Gly Val Leu
            500                 505                 510

Val Ser Ile Val Asp Thr Val Thr Ser Ile Gly Gly Asn Glu Ser Trp
        515                 520                 525

Leu Ser Thr Asn Ile Asn Arg Gly His Leu Asn Tyr Tyr Tyr Gly Leu
    530                 535                 540

Leu Thr Phe Leu Gly Ile Leu Asn Tyr Phe Tyr Tyr Leu Val Ile Cys
545                 550                 555                 560

Trp Ala Tyr Gly Pro Ile Gln Gly Glu Lys His Glu Asp Ser Ala Arg
                565                 570                 575

Lys Lys Asp Asp Lys Phe Gly Tyr Arg Glu Leu Pro Thr Ser
```

-continued 580 585 590

<210> SEQ ID NO 7
<211> LENGTH: 1776
<212> TYPE: DNA
<213> ORGANISM: M. Truncatula

<400> SEQUENCE: 7
atggagtaca caaacagtga tgatgctaca aatgaaaaac tcattgaaaa tggcagctct 60
tcatcatctt ctcaacccag aaagggtggt ttaagaacca tgccctttat catagtgaat 120
gagtgtcttg agaaagtggc aagttatgga ataatgccaa acatgatatt atacttgagg 180
gatgattata acatgcctat tgctaaggct agttatgttc tttctacttg gtctgctatg 240
tccaatgttt tgtccatctt tggtgctttt ctctctgatt cttacttggg tcgcttcaat 300
gtcatcacta ttggctcctt ttctagcctt cttggtttaa ccgttttgtg gttaactgcc 360
atgatcccgg tgctaaaacc tacctgtgca tcactctttg aaatctgtaa ttctgctact 420
tcatcccaac aagcagttct gttcctttcc ttaggattaa tttcaattgg agctggttgt 480
gttagacctt gttccatagc ctttggagca aagcaattga ctattaaggg aaattctggt 540
gatgggaatg gcaggatctt ggatagttac tttaattggt attatacctc aatttcagtt 600
tcaaccatta tcgcgttgag tgtgattgct tacattcaag aaaaccttgg atggaaaatt 660
gggtttggag tacctgctgt gctaatgctc gtatcggtca tcagtttcat tattggttca 720
ccgttatatg tcaaagtgaa gccaagtgaa agcttactca ctaattttgc aagagtagtt 780
gtggtggcaa ccaagaacag aaaacttagt cttcctgatc acgactctga tcgttactgt 840
caaggtcatg attcaaagct gaaggttcct accgatagcc ttaggttttt gaacaaagct 900
tgcgtaataa gaaatcctga gacagatctt aatcgagatg ggtcaatttc aaatccgtgg 960
aacctatgca caatagaaca ggtggagtca ctgaagtctt tgctcagagt cattcctatg 1020
tggtcaacgg gaatctttat gatggcgact cagagttcat tttctactct tcaagccaaa 1080
actttgaacc gaacgttatt cggcaatttc aattttcctg caggatcgtt caatcttatc 1140
ttgatattca ccttaacaat agtaattcct ttatatgacc gtgtaggagt acctctacta 1200
gctaaatacg caggccggcc tagaggattc agttttaaag tccgcatcgg gataggaatg 1260
ctgtttgcaa ttgtagctaa agcagtagca gctattgttg aaacggtgag acgaaatgca 1320
gcgattgaac aagggtttga ggaccaacct aatgctgaaa ttaacatgtc ggctttatgg 1380
cttgctccag agtttatttt gtttggattc gccgaagctt tcacaccagt tggactggtt 1440
gagtttttct actgtttttt ccctaagagt atgtctagtt ttgcaatggc tatgttcaca 1500
ttgggactag cttgttctga cgtagtttca ggtgtgcttg tgagcattgt ggacacggtc 1560
actagtattg gagggaatga gagctggtta tcgactaaca tcaatagggg acatttgaat 1620
tactactacg ggctactcac tttcttaggc attcttaact acttctatta tcttgttatt 1680
tgttgggctt atggacccat acagggagag aaacatgaag attcggccag aaagaaagac 1740
gataaatttg gttacaggga gttgcctact tcatag 1776

<210> SEQ ID NO 8
<211> LENGTH: 591
<212> TYPE: PRT
<213> ORGANISM: M. Truncatula

<400> SEQUENCE: 8

Met Glu Tyr Thr Asn Ser Asp Asp Ala Thr Asn Glu Lys Leu Ile Glu

-continued

```
1               5                   10                  15

Asn Gly Ser Ser Ser Ser Ser Ser Gln Pro Arg Lys Gly Gly Leu Arg
            20                  25                  30

Thr Met Pro Phe Ile Ile Val Asn Glu Cys Leu Glu Lys Val Ala Ser
        35                  40                  45

Tyr Gly Ile Met Pro Asn Met Ile Leu Tyr Leu Arg Asp Asp Tyr Asn
    50                  55                  60

Met Pro Ile Ala Lys Ala Ser Tyr Val Leu Ser Thr Trp Ser Ala Met
65                  70                  75                  80

Ser Asn Val Leu Ser Ile Phe Gly Ala Phe Leu Ser Asp Ser Tyr Leu
                85                  90                  95

Gly Arg Phe Asn Val Ile Thr Ile Gly Ser Phe Ser Ser Leu Leu Gly
            100                 105                 110

Leu Thr Val Leu Trp Leu Thr Ala Met Ile Pro Val Leu Lys Pro Thr
        115                 120                 125

Cys Ala Ser Leu Phe Glu Ile Cys Asn Ser Ala Thr Ser Ser Gln Gln
    130                 135                 140

Ala Val Leu Phe Leu Ser Leu Gly Leu Ile Ser Ile Gly Ala Gly Cys
145                 150                 155                 160

Val Arg Pro Cys Ser Ile Ala Phe Gly Ala Lys Gln Leu Thr Ile Lys
                165                 170                 175

Gly Asn Ser Gly Asp Gly Asn Gly Arg Ile Leu Asp Ser Tyr Phe Asn
            180                 185                 190

Trp Tyr Tyr Thr Ser Ile Ser Val Ser Thr Ile Ile Ala Leu Ser Val
        195                 200                 205

Ile Ala Tyr Ile Gln Glu Asn Leu Gly Trp Lys Ile Gly Phe Gly Val
    210                 215                 220

Pro Ala Val Leu Met Leu Val Ser Val Ile Ser Phe Ile Ile Gly Ser
225                 230                 235                 240

Pro Leu Tyr Val Lys Val Lys Pro Ser Glu Ser Leu Leu Thr Asn Phe
                245                 250                 255

Ala Arg Val Val Val Val Ala Thr Lys Asn Arg Lys Leu Ser Leu Pro
            260                 265                 270

Asp His Asp Ser Asp Arg Tyr Cys Gln Gly His Asp Ser Lys Leu Lys
        275                 280                 285

Val Pro Thr Asp Ser Leu Arg Phe Leu Asn Lys Ala Cys Val Ile Arg
    290                 295                 300

Asn Pro Glu Thr Asp Leu Asn Arg Asp Gly Ser Ile Ser Asn Pro Trp
305                 310                 315                 320

Asn Leu Cys Thr Ile Glu Gln Val Glu Ser Leu Lys Ser Leu Leu Arg
                325                 330                 335

Val Ile Pro Met Trp Ser Thr Gly Ile Phe Met Met Ala Thr Gln Ser
            340                 345                 350

Ser Phe Ser Thr Leu Gln Ala Lys Thr Leu Asn Arg Thr Leu Phe Gly
        355                 360                 365

Asn Phe Asn Phe Pro Ala Gly Ser Phe Asn Leu Ile Leu Ile Phe Thr
    370                 375                 380

Leu Thr Ile Val Ile Pro Leu Tyr Asp Arg Val Gly Val Pro Leu Leu
385                 390                 395                 400

Ala Lys Tyr Ala Gly Arg Pro Arg Gly Phe Ser Phe Lys Val Arg Ile
                405                 410                 415

Gly Ile Gly Met Leu Phe Ala Ile Val Ala Lys Ala Val Ala Ala Ile
            420                 425                 430
```

-continued

```
Val Glu Thr Val Arg Arg Asn Ala Ala Ile Glu Gln Gly Phe Glu Asp
        435                 440                 445

Gln Pro Asn Ala Glu Ile Asn Met Ser Ala Leu Trp Leu Ala Pro Glu
    450                 455                 460

Phe Ile Leu Phe Gly Phe Ala Glu Ala Phe Thr Pro Val Gly Leu Val
465                 470                 475                 480

Glu Phe Phe Tyr Cys Phe Phe Pro Lys Ser Met Ser Ser Phe Ala Met
                485                 490                 495

Ala Met Phe Thr Leu Gly Leu Ala Cys Ser Asp Val Val Ser Gly Val
            500                 505                 510

Leu Val Ser Ile Val Asp Thr Val Thr Ser Ile Gly Gly Asn Glu Ser
        515                 520                 525

Trp Leu Ser Thr Asn Ile Asn Arg Gly His Leu Asn Tyr Tyr Tyr Gly
    530                 535                 540

Leu Leu Thr Phe Leu Gly Ile Leu Asn Tyr Phe Tyr Tyr Leu Val Ile
545                 550                 555                 560

Cys Trp Ala Tyr Gly Pro Ile Gln Gly Glu Lys His Glu Asp Ser Ala
                565                 570                 575

Arg Lys Lys Asp Asp Lys Phe Gly Tyr Arg Glu Leu Pro Thr Ser
            580                 585                 590
```

<210> SEQ ID NO 9
<211> LENGTH: 35
<212> TYPE: DNA
<213> ORGANISM: Artificial Sequence
<220> FEATURE:
<223> OTHER INFORMATION: Synthesized

<400> SEQUENCE: 9
tgaaccatgg agtacacaaa cagtgatgat gctac 35

<210> SEQ ID NO 10
<211> LENGTH: 34
<212> TYPE: DNA
<213> ORGANISM: Artificial Sequence
<220> FEATURE:
<223> OTHER INFORMATION: Synthesized

<400> SEQUENCE: 10
aaaaaggtca cctatgaagt aggcaactcc ctgt 34

<210> SEQ ID NO 11
<211> LENGTH: 38
<212> TYPE: DNA
<213> ORGANISM: Artificial Sequence
<220> FEATURE:
<223> OTHER INFORMATION: Synthesized

<400> SEQUENCE: 11
caagtcatga ctcttcctga aactaaatct gatgatat 38

<210> SEQ ID NO 12
<211> LENGTH: 39
<212> TYPE: DNA
<213> ORGANISM: Artificial Sequence
<220> FEATURE:
<223> OTHER INFORMATION: Synthesized

<400> SEQUENCE: 12
gagctggtca cctcaatgac ccattggaat actcggctc 39

-continued

<210> SEQ ID NO 13
<211> LENGTH: 38
<212> TYPE: DNA
<213> ORGANISM: Artificial Sequence
<220> FEATURE:
<223> OTHER INFORMATION: Synthesized

<400> SEQUENCE: 13
gctagctagc atggagtaca caaacagtga tgatgcta 38

<210> SEQ ID NO 14
<211> LENGTH: 34
<212> TYPE: DNA
<213> ORGANISM: Artificial Sequence
<220> FEATURE:
<223> OTHER INFORMATION: Synthesized

<400> SEQUENCE: 14
gtcggatcct atgaagtagg caactccctg taac 34

<210> SEQ ID NO 15
<211> LENGTH: 33
<212> TYPE: DNA
<213> ORGANISM: Artificial Sequence
<220> FEATURE:
<223> OTHER INFORMATION: Synthesized

<400> SEQUENCE: 15
cgaggatcca tggagtacac aaacagtgat gat 33

<210> SEQ ID NO 16
<211> LENGTH: 24
<212> TYPE: DNA
<213> ORGANISM: Artificial Sequence
<220> FEATURE:
<223> OTHER INFORMATION: Synthesized

<400> SEQUENCE: 16
gggtctgctt cagtaagcca gatg 24

<210> SEQ ID NO 17
<211> LENGTH: 24
<212> TYPE: DNA
<213> ORGANISM: Artificial Sequence
<220> FEATURE:
<223> OTHER INFORMATION: Synthesized

<400> SEQUENCE: 17
gatcctctag agtcgacctg cagg 24

<210> SEQ ID NO 18
<211> LENGTH: 30
<212> TYPE: DNA
<213> ORGANISM: Artificial Sequence
<220> FEATURE:
<223> OTHER INFORMATION: Synthesized

<400> SEQUENCE: 18
taaaatgaaa atctgatact agaattcaag 30

<210> SEQ ID NO 19
<211> LENGTH: 46
<212> TYPE: DNA
<213> ORGANISM: Artificial Sequence
<220> FEATURE:
<223> OTHER INFORMATION: Synthesized

<400> SEQUENCE: 19
cactgtttgt gtacttcatg attcactctt ctttggtagc ttcttc 46

<210> SEQ ID NO 20
<211> LENGTH: 35
<212> TYPE: DNA
<213> ORGANISM: Artificial Sequence
<220> FEATURE:
<223> OTHER INFORMATION: Synthesized

<400> SEQUENCE: 20
tcactagatc tatggaggaa agcaagaaga gttgc 35

<210> SEQ ID NO 21
<211> LENGTH: 34
<212> TYPE: DNA
<213> ORGANISM: Artificial Sequence
<220> FEATURE:
<223> OTHER INFORMATION: Synthesized

<400> SEQUENCE: 21
atgcgctagc tcacactttt tcttctttac catt 34

<210> SEQ ID NO 22
<211> LENGTH: 967
<212> TYPE: DNA
<213> ORGANISM: Artificial Sequence
<220> FEATURE:
<223> OTHER INFORMATION: Synthesized

<400> SEQUENCE: 22
ctagagaaga gtgtcatata gattgatggt ccacaatcaa tgaaattttt gggagacgaa 60
catgtataac catttgcttg aataacctta attaaaaggt gtgattaaat gatgtttgta 120
acatgtagta ctaaacattc ataaaacaca accaacccaa gaggtattga gtattcacgg 180
ctaaacaggg gcataatggt aatttaaaga atgatattat tttatgttaa accctaacat 240
tggtttcgga ttcaacgcta taaataaaac cactctcgtt gctgattcca tttatcgttc 300
ttattgaccc tagccgctac acacttttct gcgatatctc tgaggtaagc gttaacgtac 360
ccttagatcg ttctttttct ttttcgtctg ctgatcgttg ctcatattat ttcgatgatt 420
gttggattcg atgctctttg ttgattgatc gttctgaaaa ttctgatctg ttgtttagat 480
tttatcgatt gttaatatca acgtttcact gcttctaaac gataatttat tcatgaaact 540
attttcccat tctgatcgat cttgttttga gattttaatt tgttcgattg attgttggtt 600
ggtggatcta tatacgagtg aacttgttga tttgcgtatt taagatgtat gtcgatttga 660
attgtgattg ggtaattctg gagtagcata acaaatccag tgttcccttt ttctaagggt 720
aattctcgga ttgtttgctt tatatctctt gaaattgccg atttgattga atttagcgcg 780
cttagctcag atgatagagc accacaattt ttgtggtgag aaatcggttt gactccgata 840
gcggcttttt actatgattg ttttgtgtta aagatgattt tcataatggt tatatatgtc 900
tactgttttt tattgattca atatttgatt gttctttttt ttgcagattt gttgacagtc 960
tctaacc 967

<210> SEQ ID NO 23
<211> LENGTH: 2743
<212> TYPE: DNA
<213> ORGANISM: Artificial Sequence
<220> FEATURE:

<223> OTHER INFORMATION: Synthesized

<400> SEQUENCE: 23

```
ctagagaaga gtgtcatata gattgatggt ccacaatcaa tgaaattttt gggagacgaa     60
catgtataac catttgcttg aataacctta attaaaaggt gtgattaaat gatgtttgta    120
acatgtagta ctaaacattc ataaaacaca accaacccaa gaggtattga gtattcacgg    180
ctaaacaggg gcataatggt aatttaaaga atgatattat tttatgttaa accctaacat    240
tggtttcgga ttcaacgcta taaataaaac cactctcgtt gctgattcca tttatcgttc    300
ttattgaccc tagccgctac acacttttct gcgatatctc tgaggtaagc gttaacgtac    360
ccttagatcg ttcttttct ttttcgtctg ctgatcgttg ctcatattat ttcgatgatt    420
gttggattcg atgctctttg ttgattgatc gttctgaaaa ttctgatctg ttgtttagat    480
tttatcgatt gttaatatca acgtttcact gcttctaaac gataatttat tcatgaaact    540
attttcccat tctgatcgat cttgttttga gattttaatt tgttcgattg attgttggtt    600
ggtggatcta tatacgagtg aacttgttga tttgcgtatt taagatgtat gtcgatttga    660
attgtgattg ggtaattctg gagtagcata acaaatccag tgttcccttt ttctaagggt    720
aattctcgga ttgtttgctt tatatctctt gaaattgccg atttgattga atttagcgcg    780
cttagctcag atgatagagc accacaattt ttgtggtgag aaatcggttt gactccgata    840
gcggcttttt actatgattg ttttgtgtta aagatgattt tcataatggt tatatatgtc    900
tactgttttt tattgattca atatttgatt gttctttttt ttgcagattt gttgacagtc    960
tctaaccatg gagtacacaa acagtgatga tgctacaaat gaaaaactca ttgaaaatgg   1020
cagctcttca tcatcttctc aacccagaaa gggtggttta agaaccatgc cctttatcat   1080
agtgaatgag tgtcttgaga aagtggcaag ttatggaata atgccaaaca tgatattata   1140
cttgagggat gattataaca tgcctattgc taaggctagt tatgttcttt ctacttggtc   1200
tgctatgtcc aatgttttgt ccatctttgg tgcttttctc tctgattctt acttgggtcg   1260
cttcaatgtc atcactattg gctccttttc tagccttctt ggtttaaccg ttttgtggtt   1320
aactgccatg atcccggtgc taaaacctac ctgtgcatca ctctttgaaa tctgtaattc   1380
tgctacttca tcccaacaag cagttctgtt cctttcctta ggattaattt caattggagc   1440
tggttgtgtt agaccttgtt ccatagcctt tggagcagag caattgacta ttaagggaaa   1500
ttctggtgat gggaatggca ggatcttgga tagttacttt aattggtatt atacctcaat   1560
ttcagtttca accattatcg cgttgagtgt gattgcttac attcaagaaa accttggatg   1620
gaaaattggg tttggagtac ctgctgtgct aatgctcgta tcggtcatca gtttcattat   1680
tggttcaccg ttatatgtca aagtgaagcc aagtgaaagc ttactcacta attttgcaag   1740
agtagttgtg gtggcaacca agaacagaaa acttagtctt cctgatcacg actctgatcg   1800
ttactgtcaa ggtcatgatt caaagctgaa ggttcctacc gatagcctta ggtttttgaa   1860
caaagcttgc gtaataagaa atcctgagac agatcttaat cgagatgggt caatttcaaa   1920
tccgtggaac ctatgcacaa tagaacaggt ggagtcactg aagtctttgc tcagagtcat   1980
tcctatgtgg tcaacgggaa tctttatgat ggcgactcag agttcatttt ctactcttca   2040
agccaaaact ttgaaccgaa cgttattcgg caatttcaat tttcctgcag gatcgttcaa   2100
tcttatcttg atattcacct taacaatagt aattccttta tatgaccgtg taggagtacc   2160
tctactagct aaatacgcag gccggcctag aggattcagt tttaaagtcc gcatcgggat   2220
aggaatgctg tttgcaattg tagctaaagc agtagcagct attgttgaaa cggtgagacg   2280
```

-continued

```
aaatgcagcg attgaacaag ggtttgagga ccaacctaat gctgaaatta acatgtcggc   2340
tttatggctt gctccagagt ttattttgtt tggattcgcc gaagctttca caccagttgg   2400
actggttgag tttttctact gtttttttccc taagagtatg tctagttttg caatggctat   2460
gttcacattg ggactagctt gttctgacgt agtttcaggt gtgcttgtga gcattgtgga   2520
cacggtcact agtattggag ggaatgagag ctggttatcg actaacatca ataggggaca   2580
tttgaattac tactacgggc tactcacttt cttaggcatt cttaactact tctattatct   2640
tgttatttgt tgggcttatg gacccataca gggagagaaa catgaagatt cggccagaaa   2700
gaaagacgat aaatttggtt acagggagtt gcctacttca tag                     2743
```

```
<210> SEQ ID NO 24
<211> LENGTH: 2743
<212> TYPE: DNA
<213> ORGANISM: Artificial Sequence
<220> FEATURE:
<223> OTHER INFORMATION: Synthesized

<400> SEQUENCE: 24

ctagagaaga gtgtcatata gattgatggt ccacaatcaa tgaaattttt gggagacgaa     60
catgtataac catttgcttg aataacctta attaaaaggt gtgattaaat gatgtttgta    120
acatgtagta ctaaacattc ataaaacaca accaacccaa gaggtattga gtattcacgg    180
ctaaacaggg gcataatggt aatttaaaga atgatattat tttatgttaa accctaacat    240
tggtttcgga ttcaacgcta taaataaaac cactctcgtt gctgattcca tttatcgttc    300
ttattgaccc tagccgctac acacttttct gcgatatctc tgaggtaagc gttaacgtac    360
ccttagatcg ttctttttct ttttcgtctg ctgatcgttg ctcatattat ttcgatgatt    420
gttggattcg atgctctttg ttgattgatc gttctgaaaa ttctgatctg ttgtttagat    480
tttatcgatt gttaatatca acgtttcact gcttctaaac gataatttat tcatgaaact    540
attttcccat tctgatcgat cttgttttga gattttaatt tgttcgattg attgttggtt    600
ggtggatcta tatacgagtg aacttgttga tttgcgtatt taagatgtat gtcgatttga    660
attgtgattg ggtaattctg gagtagcata acaaatccag tgttcccttt ttctaagggt    720
aattctcgga ttgtttgctt tatatctctt gaaattgccg atttgattga atttagcgcg    780
cttagctcag atgatagagc accacaattt ttgtggtgag aaatcggttt gactccgata    840
gcggcttttt actatgattg ttttgtgtta aagatgattt tcataatggt tatatatgtc    900
tactgttttt tattgattca atatttgatt gttctttttt ttgcagattt gttgacagtc    960
tctaaccatg gagtacacaa acagtgatga tgctacaaat gaaaaactca ttgaaaatgg   1020
cagctcttca tcatcttctc aacccagaaa gggtggttta agaaccatgc cctttatcat   1080
agtgaatgag tgtcttgaga aagtggcaag ttatggaata atgccaaaca tgatattata   1140
cttgagggat gattataaca tgcctattgc taaggctagt tatgttcttt ctacttggtc   1200
tgctatgtcc aatgttttgt ccatctttgg tgcttttctc tctgattctt acttgggtcg   1260
cttcaatgtc atcactattg gctccttttc tagccttctt ggtttaaccg ttttgtggtt   1320
aactgccatg atcccggtgc taaaacctac ctgtgcatca ctctttgaaa tctgtaattc   1380
tgctacttca tcccaacaag cagttctgtt cctttcctta ggattaattt caattggagc   1440
tggttgtgtt agaccttgtt ccatagcctt tggagcagag caattgacta ttaagggaaa   1500
ttctggtgat gggaatggca ggatcttgga tagttacttt aattggtatt atacctcaat   1560
```

-continued

```
ttcagtttca accattatcg cgttgagtgt gattgcttac attcaagaaa accttggatg   1620

gaaaattggg tttggagtac ctgctgtgct aatgctcgta tcggtcatca gtttcattat   1680

tggttcaccg ttatatgtca aagtgaagcc aagtgaaagc ttactcacta attttgcaag   1740

agtagttgtg gtggcaacca agaacagaaa acttagtctt cctgatcacg actctgatcg   1800

ttactgtcaa ggtcatgatt caaagctgaa ggttcctacc gatagcctta ggtttttgaa   1860

caaagcttgc gtaataagaa atcctgagac agatcttaat cgagatgggt caatttcaaa   1920

tccgtggaac ctatgcacaa tagaacaggt ggagtcactg aagtctttgc tcagagtcat   1980

tcctatgtga tcaacgggaa tctttatgat ggcgactcag agttcatttt ctactcttca   2040

agccaaaact ttgaaccgaa cgttattcgg caatttcaat tttcctgcag gatcgttcaa   2100

tcttatcttg atattcacct taacaatagt aattccttta tatgaccgtg taggagtacc   2160

tctactagct aaatacgcag gccggcctag aggattcagt tttaaagtcc gcatcgggat   2220

aggaatgctg tttgcaattg tagctaaagc agtagcagct attgttgaaa cggtgagacg   2280

aaatgcagcg attgaacaag ggtttgagga ccaacctaat gctgaaatta acatgtcggc   2340

tttatggctt gctccagagt ttattttgtt tggattcgcc gaagctttca caccagttgg   2400

actggttgag tttttctact gtttttttccc taagagtatg tctagttttg caatggctat   2460

gttcacattg ggactagctt gttctgacgt agtttcaggt gtgcttgtga gcattgtgga   2520

cacggtcact agtattggag ggaatgagag ctggttatcg actaacatca atagggggaca   2580

tttgaattac tactacgggc tactcacttt cttaggcatt cttaactact tctattatct   2640

tgttatttgt tgggcttatg gacccataca gggagagaaa catgaagatt cggccagaaa   2700

gaaagacgat aaatttggtt acagggagtt gcctacttca tag                   2743
```

<210> SEQ ID NO 25
<211> LENGTH: 3325
<212> TYPE: DNA
<213> ORGANISM: Artificial Sequence
<220> FEATURE:
<223> OTHER INFORMATION: Synthesized

<400> SEQUENCE: 25

```
gttgtggttg gtgctttcct tacattctga gcctctttcc ttctaatcca ctcatctgca     60

tcttcttgtg tccttactaa tacctcattg gttccaaatt ccctcccttt aagcaccagc    120

tcgtttctgt tcttccacag cctcccaagt atccaaggga ctaaagcctc cacattcttc    180

agatcaggat attcttgttt aagatgttga actctatgga ggtttgtatg aactgatgat    240

ctaggaccgg ataagttccc ttcttcatag cgaacttatt caaagaatgt tttgtgtatc    300

attcttgtta cattgttatt aatgaaaaaa tattattggt cattggactg aacacgagtg    360

ttaaatatgg accaggcccc aaataagatc cattgatata tgaattaaat aacaagaata    420

aatcgagtca ccaaaccact tgcctttttt aacgagactt gttcaccaac ttgatacaaa    480

agtcattatc ctatgcaaat caataatcat acaaaaatat ccaataacac taaaaaaatt    540

aaaagaaatg gataatttca caatatgtta tacgataaag aagttacttt tccaagaaat    600

tcactgattt tataagccca cttgcattag ataaatggca aaaaaaaaca aaaaggaaaa    660

gaaataaagc acgaagaatt ctagaaaata cgaaatacgc ttcaatgcag tggggaccca    720

cggttcaatt attgccaatt tttcagctcc accgtatatt taaaaaaataa aacgataatg    780

ctaaaaaaat ataaatcgta acgatcgtta aatctcaacg gctggatctt atgacgaccg    840

ttaaggaaat tgtggttgtc ggacgaagtc cagtaataaa cggcgtcaaa gtggttgcag    900
```

```
ccggcacaca cgagtcgtgt ttatcaactc aaagcacaaa tacttttcct caacctaaaa    960
ataaggcaat tagccaaaaa caactttgcg tgtaaacaac gctcaataca cgtgtcattt   1020
tattattagc tattgcttca ccgccttagc tttctcgtga cctagtcgtc ctcgtctttt   1080
cttcttcttc ttctataaaa caatacccaa agagctcttc ttcttcacaa ttcagatttc   1140
aatttctcaa aatcttaaaa actttctctc aattctctct accgtgatca aggtaaattt   1200
ctgtgttcct tattctctca aaatcttcga ttttgttttc gttcgatccc aatttcgtat   1260
atgttctttg gtttagattc tgttaatctt agatcgaaga cgattttctg ggtttgatcg   1320
ttagatatca tcttaattct cgattagggt ttcatagata tcatccgatt tgttcaaata   1380
atttgagttt tgtcgaataa ttactcttcg atttgtgatt tctatctaga tctggtgtta   1440
gtttctagtt tgtgcgatcg aatttgtcga ttaatctgag tttttctgat taacagatgc   1500
agatctttgc catggcgcgc tcctccaaga acgtcatcaa ggagttcata tggagtacac   1560
aaacagtgat gatgctacaa atgaaaaact cattgaaaat ggcagctctt catcatcttc   1620
tcaacccaga aagggtggtt taagaaccat gccctttatc atagtgaatg agtgtcttga   1680
gaaagtggca agttatggaa taatgccaaa catgatatta tacttgaggg atgattataa   1740
catgcctatt gctaaggcta gttatgttct ttctacttgg tctgctatgt ccaatgtttt   1800
gtccatcttt ggtgcttttc tctctgattc ttacttgggt cgcttcaatg tcatcactat   1860
tggctccttt tctagccttc ttggtttaac cgttttgtgg ttaactgcca tgatcccggt   1920
gctaaaacct acctgtgcat cactctttga aatctgtaat tctgctactt catcccaaca   1980
agcagttctg ttcctttcct taggattaat ttcaattgga gctggttgtg ttagaccttg   2040
ttccatagcc tttggagcag agcaattgac tattaaggga aattctggtg atgggaatgg   2100
caggatcttg gatagttact ttaattggta ttatacctca atttcagttt caaccattat   2160
cgcgttgagt gtgattgctt acattcaaga aaaccttgga tggaaaattg ggtttggagt   2220
acctgctgtg ctaatgctcg tatcggtcat cagtttcatt attggttcac cgttatatgt   2280
caaagtgaag ccaagtgaaa gcttactcac taattttgca agagtagttg tggtggcaac   2340
caagaacaga aaacttagtc ttcctgatca cgactctgat cgttactgtc aaggtcatga   2400
ttcaaagctg aaggttccta ccgatagcct taggtttttg aacaaagctt gcgtaataag   2460
aaatcctgag acagatctta atcgagatgg gtcaatttca aatccgtgga acctatgcac   2520
aatagaacag gtggagtcac tgaagtcttt gctcagagtc attcctatgt ggtcaacggg   2580
aatctttatg atggcgactc agagttcatt ttctactctt caagccaaaa ctttgaaccg   2640
aacgttattc ggcaatttca attttcctgc aggatcgttc aatcttatct tgatattcac   2700
cttaacaata gtaattcctt tatatgaccg tgtaggagta cctctactag ctaaatacgc   2760
aggccggcct agaggattca gttttaaagt ccgcatcggg ataggaatgc tgtttgcaat   2820
tgtagctaaa gcagtagcag ctattgttga aacggtgaga cgaaatgcag cgattgaaca   2880
agggtttgag gaccaaccta atgctgaaat taacatgtcg gctttatggc ttgctccaga   2940
gtttattttg tttggattcg ccgaagcttt cacaccagtt ggactggttg agtttttcta   3000
ctgtttttc cctaagagta tgtctagttt tgcaatggct atgttcacat tgggactagc   3060
ttgttctgac gtagtttcag gtgtgcttgt gagcattgtg gacacggtca ctagtattgg   3120
agggaatgag agctggttat cgactaacat caatagggga catttgaatt actactacgg   3180
gctactcact ttcttaggca ttcttaacta cttctattat cttgttattt gttgggctta   3240
```

-continued

```
tggacccata cagggagaga aacatgaaga ttcggccaga aagaaagacg ataaatttgg   3300

ttacagggag ttgcctactt catag                                        3325


<210> SEQ ID NO 26
<211> LENGTH: 11810
<212> TYPE: DNA
<213> ORGANISM: Artificial Sequence
<220> FEATURE:
<223> OTHER INFORMATION: Synthesized

<400> SEQUENCE: 26

catgccaacc acagggttcc cctcgggatc aaagtacttt gatccaaccc ctccgctgct     60

atagtgcagt cggcttctga cgttcagtgc agccgtcttc tgaaaacgac atgtcgcaca    120

agtcctaagt tacgcgacag gctgccgccc tgccctttc ctggcgtttt cttgtcgcgt    180

gttttagtcg cataaagtag aatacttgcg actagaaccg gagacattac gccatgaaca    240

agagcgccgc cgctggcctg ctgggctatg cccgcgtcag caccgacgac caggacttga    300

ccaaccaacg ggccgaactg cacgcggccg gctgcaccaa gctgttttcc gagaagatca    360

ccggcaccag gcgcgaccgc ccggagctgg ccaggatgct tgaccaccta cgccctggcg    420

acgttgtgac agtgaccagg ctagaccgcc tggcccgcag cacccgcgac ctactggaca    480

ttgccgagcg catccaggag gccggcgcgg gcctgcgtag cctggcagag ccgtgggccg    540

acaccaccac gccggccggc cgcatggtgt tgaccgtgtt cgccggcatt gccgagttcg    600

agcgttccct aatcatcgac cgcacccgga gcgggcgcga ggccgccaag gcccgaggcg    660

tgaagtttgg cccccgccct accctcaccc cggcacagat cgcgcacgcc cgcgagctga    720

tcgaccagga aggccgcacc gtgaaagagg cggctgcact gcttggcgtg catcgctcga    780

ccctgtaccg cgcacttgag cgcagcgagg aagtgacgcc caccgaggcc aggcggcgcg    840

gtgccttccg tgaggacgca ttgaccgagg ccgacgccct ggcggccgcc gagaatgaac    900

gccaagagga acaagcatga aaccgcacca ggacggccag gacgaaccgt ttttcattac    960

cgaagagatc gaggcggaga tgatcgcggc cgggtacgtg ttcgagccgc ccgcgcacgt   1020

ctcaaccgtg cggctgcatg aaatcctggc cggtttgtct gatgccaagc tggcggcctg   1080

gccggccagc ttggccgctg aagaaaccga gcgccgccgt ctaaaaaggt gatgtgtatt   1140

tgagtaaaac agcttgcgtc atgcggtcgc tgcgtatatg atgcgatgag taaataaaca   1200

aatacgcaag gggaacgcat gaaggttatc gctgtactta accagaaagg cgggtcaggc   1260

aagacgacca tcgcaaccca tctagcccgc gccctgcaac tcgccggggc cgatgttctg   1320

ttagtcgatt ccgatcccca gggcagtgcc cgcgattggg cggccgtgcg ggaagatcaa   1380

ccgctaaccg ttgtcggcat cgaccgcccg acgattgacc gcgacgtgaa ggccatcggc   1440

cggcgcgact tcgtagtgat cgacggagcg ccccaggcgg cggacttggc tgtgtccgcg   1500

atcaaggcag ccgacttcgt gctgattccg gtgcagccaa gcccttacga catatgggcc   1560

accgccgacc tggtggagct ggttaagcag cgcattgagg tcacggatgg aaggctacaa   1620

gcggcctttg tcgtgtcgcg ggcgatcaaa ggcacgcgca tcggcggtga ggttgccgag   1680

gcgctggccg ggtacgagct gcccattctt gagtcccgta tcacgcagcg cgtgagctac   1740

ccaggcactg ccgccgccgg cacaaccgtt cttgaatcag aacccgaggg cgacgctgcc   1800

cgcgaggtcc aggcgctggc cgctgaaatt aaatcaaaac tcatttgagt taatgaggta   1860

aagagaaaat gagcaaaagc acaaacacgc taagtgccgg ccgtccgagc gcacgcagca   1920

gcaaggctgc aacgttggcc agcctggcag acacgccagc catgaagcgg gtcaactttc   1980
```

```
agttgccggc ggaggatcac accaagctga agatgtacgc ggtacgccaa ggcaagacca   2040
ttaccgagct gctatctgaa tacatcgcgc agctaccaga gtaaatgagc aaatgaataa   2100
atgagtagat gaattttagc ggctaaagga ggcggcatgg aaaatcaaga acaaccaggc   2160
accgacgccg tggaatgccc catgtgtgga ggaacgggcg gttggccagg cgtaagcggc   2220
tgggttgtct gccggccctg caatggcact ggaaccccca agcccgagga atcggcgtga   2280
cggtcgcaaa ccatccggcc cggtacaaat cggcgcggcg ctgggtgatg acctggtgga   2340
gaagttgaag gccgcgcagg ccgcccagcg gcaacgcatc gaggcagaag cacgccccgg   2400
tgaatcgtgg caagcggccg ctgatcgaat ccgcaaagaa tcccggcaac cgccggcagc   2460
cggtgcgccg tcgattagga agccgcccaa gggcgacgag caaccagatt ttttcgttcc   2520
gatgctctat gacgtgggca cccgcgatag tcgcagcatc atggacgtgg ccgttttccg   2580
tctgtcgaag cgtgaccgac gagctggcga ggtgatccgc tacgagcttc cagacgggca   2640
cgtagaggtt tccgcagggc cggccggcat ggccagtgtg tgggattacg acctggtact   2700
gatggcggtt tcccatctaa ccgaatccat gaaccgatac cgggaaggga agggagacaa   2760
gcccggccgc gtgttccgtc cacacgttgc ggacgtactc aagttctgcc ggcgagccga   2820
tggcggaaag cagaaagacg acctggtaga aacctgcatt cggttaaaca ccacgcacgt   2880
tgccatgcag cgtacgaaga aggccaagaa cggccgcctg gtgacggtat ccgagggtga   2940
agccttgatt agccgctaca agatcgtaaa gagcgaaacc gggcggccgg agtacatcga   3000
gatcgagcta gctgattgga tgtaccgcga gatcacagaa ggcaagaacc cggacgtgct   3060
gacggttcac cccgattact ttttgatcga tcccggcatc ggccgttttc tctaccgcct   3120
ggcacgccgc gccgcaggca aggcagaagc cagatggttg ttcaagacga tctacgaacg   3180
cagtggcagc gccggagagt tcaagaagtt ctgtttcacc gtgcgcaagc tgatcgggtc   3240
aaatgacctg ccggagtacg atttgaagga ggaggcgggg caggctggcc cgatcctagt   3300
catgcgctac cgcaacctga tcgagggcga agcatccgcc ggttcctaat gtacggagca   3360
gatgctaggg caaattgccc tagcagggga aaaaggtcga aaaggtctct ttcctgtgga   3420
tagcacgtac attgggaacc caaagccgta cattgggaac cggaacccgt acattgggaa   3480
cccaaagccg tacattggga accggtcaca catgtaagtg actgatataa aagagaaaaa   3540
aggcgatttt tccgcctaaa actctttaaa acttattaaa actcttaaaa cccgcctggc   3600
ctgtgcataa ctgtctggcc agcgcacagc cgaagagctg caaaaagcgc ctacccttcg   3660
gtcgctgcgc tccctacgcc ccgccgcttc gcgtcggcct atcgcggccg ctggccgctc   3720
aaaaatggct ggcctacggc caggcaatct accagggcgc ggacaagccg cgccgtcgcc   3780
actcgaccgc cggcgcccac atcaaggcac cctgcctcgc gcgtttcggt gatgacggtg   3840
aaaacctctg acacatgcag ctcccggaga cggtcacagc ttgtctgtaa gcggatgccg   3900
ggagcagaca agcccgtcag ggcgcgtcag cgggtgttgg cgggtgtcgg ggcgcagcca   3960
tgacccagtc acgtagcgat agcggagtgt atactggctt aactatgcgg catcagagca   4020
gattgtactg agagtgcacc atatgcggtg tgaaataccg cacagatgcg taaggagaaa   4080
ataccgcatc aggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
```

-continued acgctcaagt cagaggtggc gaaacccgac aggactataa agataccagg cgtttccccc 4380
tggaagctcc ctcgtgcgct ctcctgttcc gaccctgccg cttaccggat acctgtccgc 4440
ctttctccct tcgggaagcg tggcgctttc tcatagctca cgctgtaggt atctcagttc 4500
ggtgtaggtc gttcgctcca agctgggctg tgtgcacgaa ccccccgttc agcccgaccg 4560
ctgcgcctta tccggtaact atcgtcttga gtccaacccg gtaagacacg acttatcgcc 4620
actggcagca gccactggta acaggattag cagagcgagg tatgtaggcg gtgctacaga 4680
gttcttgaag tggtggccta actacggcta cactagaagg acagtatttg gtatctgcgc 4740
tctgctgaag ccagttacct tcggaaaaag agttggtagc tcttgatccg gcaaacaaac 4800
caccgctggt agcggtggtt tttttgtttg caagcagcag attacgcgca gaaaaaaagg 4860
atctcaagaa gatcctttga tcttttctac ggggtctgac gctcagtgga acgaaaactc 4920
acgttaaggg attttggtca tgcattctag gtactaaaac aattcatcca gtaaaatata 4980
atattttatt ttctcccaat caggcttgat ccccagtaag tcaaaaaata gctcgacata 5040
ctgttcttcc ccgatatcct ccctgatcga ccggacgcag aaggcaatgt cataccactt 5100
gtccgccctg ccgcttctcc caagatcaat aaagccactt actttgccat ctttcacaaa 5160
gatgttgctg tctcccaggt cgccgtggga aaagacaagt tcctcttcgg gcttttccgt 5220
ctttaaaaaa tcatacagct cgcgcggatc tttaaatgga gtgtcttctt cccagttttc 5280
gcaatccaca tcggccagat cgttattcag taagtaatcc aattcggcta agcggctgtc 5340
taagctattc gtatagggac aatccgatat gtcgatggag tgaaagagcc tgatgcactc 5400
cgcatacagc tcgataatct tttcagggct ttgttcatct tcatactctt ccgagcaaag 5460
gacgccatcg gcctcactca tgagcagatt gctccagcca tcatgccgtt caaagtgcag 5520
gacctttgga acaggcagct ttccttccag ccatagcatc atgtcctttt cccgttccac 5580
atcataggtg gtccctttat accggctgtc cgtcattttt aaatataggt tttcattttc 5640
tcccaccagc ttatatacct tagcaggaga cattccttcc gtatctttta cgcagcggta 5700
tttttcgatc agtttttca attccggtga tattctcatt ttagccattt attatttcct 5760
tcctcttttc tacagtattt aaagataccc caagaagcta attataacaa gacgaactcc 5820
aattcactgt tccttgcatt ctaaaacctt aaataccaga aaacagcttt ttcaaagttg 5880
ttttcaaagt tggcgtataa catagtatcg acggagccga ttttgaaacc gcggtgatca 5940
caggcagcaa cgctctgtca tcgttacaat caacatgcta ccctccgcga gatcatccgt 6000
gtttcaaacc cggcagctta gttgccgttc ttccgaatag catcggtaac atgagcaaag 6060
tctgccgcct tacaacggct ctcccgctga cgccgtcccg gactgatggg ctgcctgtat 6120
cgagtggtga ttttgtgccg agctgccggt cggggagctg ttggctggct ggtggcagga 6180
tatattgtgg tgtaaacaaa ttgacgctta gacaacttaa taacacattg cggacgtttt 6240
taatgtactg aattaacgcc gaattaattc gggggatctg gattttagta ctggattttg 6300
gttttaggaa ttagaaattt tattgataga agtattttac aaatacaaat acatactaag 6360
ggtttcttat atgctcaaca catgagcgaa accctatagg aaccctaatt cccttatctg 6420
ggaactactc acacattatt atggagaaac tcgagtcaaa tctcggtgac gggcaggacc 6480
ggacggggcg gtaccggcag gctgaagtcc agctgccaga aacccacgtc atgccagttc 6540
ccgtgcttga agccggccgc ccgcagcatg ccgcgggggg catatccgag cgcctcgtgc 6600
atgcgcacgc tcgggtcgtt gggcagcccg atgacagcga ccacgctctt gaagccctgt 6660
gcctccaggg acttcagcag gtgggtgtag agcgtggagc ccagtcccgt ccgctggtgg 6720
cggggggaga cgtacacggt cgactcggcc gtccagtcgt aggcgttgcg tgccttccag 6780
gggcccgcgt aggcgatgcc ggcgacctcg ccgtccacct cggcgacgag ccagggatag 6840
cgctcccgca gacggacgag gtcgtccgtc cactcctgcg gttcctgcgg ctcggtacgg 6900
aagttgaccg tgcttgtctc gatgtagtgg ttgacgatgg tgcagaccgc cggcatgtcc 6960
gcctcggtgg cacggcggat gtcggccggg cgtcgttctg ggctcatggt agactcgaga 7020
gagatagatt tgtagagaga gactggtgat ttcagcgtgt cctctccaaa tgaaatgaac 7080
ttccttatat agaggaaggt cttgcgaagg atagtgggat tgtgcgtcat cccttacgtc 7140
agtggagata tcacatcaat ccacttgctt tgaagacgtg gttggaacgt cttctttttc 7200
cacgatgctc ctcgtgggtg gggtccatc tttgggacca ctgtcggcag aggcatcttg 7260
aacgatagcc tttcctttat cgcaatgatg gcatttgtag gtgccacctt cctttctac 7320 tgtccttttg atgaagtgac agatagctgg gcaatggaat ccgaggaggt ttcccgatat 7380
taccctttgt tgaaaagtct caatagccct ttggtcttct gagactgtat ctttgatatt 7440
cttggagtag acgagagtgt cgtgctccac catgttatca catcaatcca cttgctttga 7500
agacgtggtt ggaacgtctt ctttttccac gatgctcctc gtgggtgggg gtccatcttt 7560
gggaccactg tcggcagagg catcttgaac gatagccttt cctttatcgc aatgatggca 7620
tttgtaggtg ccaccttcct tttctactgt ccttttgatg aagtgacaga tagctgggca 7680
atggaatccg aggaggtttc ccgatattac cctttgttga aaagtctcaa tagccctttg 7740
gtcttctgag actgtatctt tgatattctt ggagtagacg agagtgtcgt gctccaccat 7800
gttggcaagc tgctctagcc aatacgcaaa ccgcctctcc ccgcgcgttg gccgattcat 7860
taatgcagct ggcacgacag gtttcccgac tggaaagcgg gcagtgagcg caacgcaatt 7920
aatgtgagtt agctcactca ttaggcaccc caggctttac actttatgct tccggctcgt 7980
atgttgtgtg gaattgtgag cggataacaa tttcacacag gaaacagcta tgaccatgat 8040
tacgaattcg agctccaccg cggtggcggc cgctctagaa ctagttaatt aaggaattat 8100
cgaaccactt tgtacaagaa agctgaacga gaaacgtaaa atgatataaa tatcaatata 8160
ttaaattaga ttttgcataa aaaacagact acataatact gtaaaacaca acatatccag 8220
tcactatggt cgacctgcag ctagagaaga gtgtcatata gattgatggt ccacaatcaa 8280
tgaaattttt gggagacgaa catgtataac catttgcttg aataacctta attaaaaggt 8340
gtgattaaat gatgtttgta acatgtagta ctaaacattc ataaaacaca accaacccaa 8400
gaggtattga gtattcacgg ctaaacaggg gcataatggt aatttaaaga atgatattat 8460
tttatgttaa accctaacat tggtttcgga ttcaacgcta taaataaaac cactctcgtt 8520
gctgattcca tttatcgttc ttattgaccc tagccgctac acacttttct gcgatatctc 8580
tgaggtaagc gttaacgtac ccttagatcg ttcttttct ttttcgtctg ctgatcgttg 8640
ctcatattat ttcgatgatt gttggattcg atgctctttg ttgattgatc gttctgaaaa 8700
ttctgatctg ttgtttagat tttatcgatt gttaatatca acgtttcact gcttctaaac 8760
gataatttat tcatgaaact attttcccat tctgatcgat cttgttttga gattttaatt 8820
tgttcgattg attgttggtt ggtggatcta tatacgagtg aacttgttga tttgcgtatt 8880
taagatgtat gtcgatttga attgtgattg ggtaattctg gagtagcata acaaatccag 8940
tgttcccttt ttctaagggt aattctcgga ttgtttgctt tatatctctt gaaattgccg 9000
atttgattga atttagcgcg cttagctcag atgatagagc accacaattt ttgtggtgag 9060

-continued

```
aaatcggttt gactccgata gcggcttttt actatgattg ttttgtgtta aagatgattt   9120
tcataatggt tatatatgtc tactgttttt tattgattca atatttgatt gttctttttt   9180
ttgcagattt gttgacagtc tctaaccatg gagtacacaa acagtgatga tgctacaaat   9240
gaaaaactca ttgaaaatgg cagctcttca tcatcttctc aacccagaaa gggtggttta   9300
agaaccatgc cctttatcat agtgaatgag tgtcttgaga aagtggcaag ttatggaata   9360
atgccaaaca tgatattata cttgagggat gattataaca tgcctattgc taaggctagt   9420
tatgttcttt ctacttggtc tgctatgtcc aatgttttgt ccatctttgg tgcttttctc   9480
tctgattctt acttgggtcg cttcaatgtc atcactattg gctccttttc tagccttctt   9540
ggtttaaccg ttttgtggtt aactgccatg atcccggtgc taaaacctac ctgtgcatca   9600
ctctttgaaa tctgtaattc tgctacttca tcccaacaag cagttctgtt cctttcctta   9660
ggattaattt caattggagc tggttgtgtt agaccttgtt ccatagcctt tggagcaaag   9720
caattgacta ttaagggaaa ttctggtgat gggaatggca ggatcttgga tagttacttt   9780
aattggtatt atacctcaat ttcagtttca accattatcg cgttgagtgt gattgcttac   9840
attcaagaaa accttggatg gaaaattggg tttggagtac ctgctgtgct aatgctcgta   9900
tcggtcatca gtttcattat tggttcaccg ttatatgtca aagtgaagcc aagtgaaagc   9960
ttactcacta attttgcaag agtagttgtg gtggcaacca agaacagaaa acttagtctt  10020
cctgatcacg actctgatcg ttactgtcaa ggtcatgatt caaagctgaa ggttcctacc  10080
gatagcctta ggtttttgaa caaagcttgc gtaataagaa atcctgagac agatcttaat  10140
cgagatgggt caatttcaaa tccgtggaac ctatgcacaa tagaacaggt ggagtcactg  10200
aagtctttgc tcagagtcat tcctatgtgg tcaacgggaa tctttatgat ggcgactcag  10260
agttcatttt ctactcttca agccaaaact ttgaaccgaa cgttattcgg caatttcaat  10320
tttcctgcag gatcgttcaa tcttatcttg atattcacct taacaatagt aattccttta  10380
tatgaccgtg taggagtacc tctactagct aaatacgcag gccggcctag aggattcagt  10440
tttaaagtcc gcatcgggat aggaatgctg tttgcaattg tagctaaagc agtagcagct  10500
attgttgaaa cggtgagacg aaatgcagcg attgaacaag ggtttgagga ccaacctaat  10560
gctgaaatta acatgtcggc tttatggctt gctccagagt ttattttgtt tggattcgcc  10620
gaagctttca caccagttgg actggttgag tttttctact gtttttttccc taagagtatg  10680
tctagttttg caatggctat gttcacattg ggactagctt gttctgacgt agtttcaggt  10740
gtgcttgtga gcattgtgga cacggtcact agtattggag ggaatgagag ctggttatcg  10800
actaacatca ataggggaca tttgaattac tactacgggc tactcacttt cttaggcatt  10860
cttaactact tctattatct tgttatttgt tgggcttatg gacccataca gggagagaaa  10920
catgaagatt cggccagaaa gaaagacgat aaatttggtt acagggagtt gcctacttca  10980
taggttctta agattgaatc ctgttgccgg tcttgcgatg attatcatat aatttctgtt  11040
gaattacgtt aagcatgtaa taattaacat gtaatgcatg acgttattta tgagatgggt  11100
ttttatgatt agagtcccgc aattatacat ttaatacgcg atagaaaaca aaatatagcg  11160
cgcaaactag gataaattat cgcgcgcggt gtcatctatg ttactagatc gggcctaact  11220
caaaatccac acattatacg agccggaagc ataaagtgta aagcctgggg tgcctaatgc  11280
ggccgccata gtgactggat atgttgtgtt ttacagtatt atgtagtctg tttttttatgc  11340
aaaatctaat ttaatatatt gatatttata tcattttacg tttctcgttc agcttttttg  11400
tacaaacttg tttgatagct tggcgcgcct cgaggggggg cccggtaccc ggggatcctc  11460
```

tagagtcgac ctgcaggcat gcggcactgg ccgtcgtttt acaacgtcgt gactgggaaa 11520
accctggcgt tacccaactt aatcgccttg cagcacatcc ccctttcgcc agctggcgta 11580
atagcgaaga ggcccgcacc gatcgccctt cccaacagtt gcgcagcctg aatggcgaat 11640
gctagagcag cttgagcttg gatcagattg tcgtttcccg ccttcagttt aaactatcag 11700
tgtttgacag gatatattgg cgggtaaacc taagagaaaa gagcgtttat tagaataacg 11760
gatatttaaa agggcgtgaa aaggtttatc cgttcgtcca tttgtatgtg 11810

<210> SEQ ID NO 27
<211> LENGTH: 13036
<212> TYPE: DNA
<213> ORGANISM: Artificial Sequence
<220> FEATURE:
<223> OTHER INFORMATION: Synthesized

<400> SEQUENCE: 27
catgccaacc acagggttcc cctcgggatc aaagtacttt gatccaaccc ctccgctgct 60
atagtgcagt cggcttctga cgttcagtgc agccgtcttc tgaaaacgac atgtcgcaca 120
agtcctaagt tacgcgacag gctgccgccc tgcccttttc ctggcgtttt cttgtcgcgt 180
gttttagtcg cataaagtag aatacttgcg actagaaccg gagacattac gccatgaaca 240
agagcgccgc cgctggcctg ctgggctatg cccgcgtcag caccgacgac caggacttga 300
ccaaccaacg ggccgaactg cacgcggccg gctgcaccaa gctgttttcc gagaagatca 360
ccggcaccag gcgcgaccgc ccggagctgg ccaggatgct tgaccaccta cgccctggcg 420
acgttgtgac agtgaccagg ctagaccgcc tggcccgcag cacccgcgac ctactggaca 480
ttgccgagcg catccaggag gccggcgcgg gcctgcgtag cctggcagag ccgtgggccg 540
acaccaccac gccggccggc cgcatggtgt tgaccgtgtt cgccggcatt gccgagttcg 600
agcgttccct aatcatcgac cgcacccgga gcgggcgcga ggccgccaag gcccgaggcg 660
tgaagtttgg cccccgccct accctcaccc cggcacagat cgcgcacgcc cgcgagctga 720
tcgaccagga aggccgcacc gtgaaagagg cggctgcact gcttggcgtg catcgctcga 780
ccctgtaccg cgcacttgag cgcagcgagg aagtgacgcc caccgaggcc aggcggcgcg 840
gtgccttccg tgaggacgca ttgaccgagg ccgacgccct ggcggccgcc gagaatgaac 900
gccaagagga acaagcatga aaccgcacca ggacggccag gacgaaccgt ttttcattac 960
cgaagagatc gaggcggaga tgatcgcggc cgggtacgtg ttcgagccgc ccgcgcacgt 1020
ctcaaccgtg cggctgcatg aaatcctggc cggtttgtct gatgccaagc tggcggcctg 1080
gccggccagc ttggccgctg aagaaaccga gcgccgccgt ctaaaaaggt gatgtgtatt 1140
tgagtaaaac agcttgcgtc atgcggtcgc tgcgtatatg atgcgatgag taaataaaca 1200
aatacgcaag gggaacgcat gaaggttatc gctgtactta accagaaagg cgggtcaggc 1260
aagacgacca tcgcaaccca tctagcccgc gccctgcaac tcgccggggc cgatgttctg 1320
ttagtcgatt ccgatcccca gggcagtgcc cgcgattggg cggccgtgcg ggaagatcaa 1380
ccgctaaccg ttgtcggcat cgaccgcccg acgattgacc gcgacgtgaa ggccatcggc 1440
cggcgcgact tcgtagtgat cgacggagcg ccccaggcgg cggacttggc tgtgtccgcg 1500
atcaaggcag ccgacttcgt gctgattccg gtgcagccaa gcccttacga catatgggcc 1560
accgccgacc tggtggagct ggttaagcag cgcattgagg tcacggatgg aaggctacaa 1620
gcggcctttg tcgtgtcgcg ggcgatcaaa ggcacgcgca tcggcggtga ggttgccgag 1680

```
gcgctggccg ggtacgagct gcccattctt gagtcccgta tcacgcagcg cgtgagctac   1740
ccaggcactg ccgccgccgg cacaaccgtt cttgaatcag aacccgaggg cgacgctgcc   1800
cgcgaggtcc aggcgctggc cgctgaaatt aaatcaaaac tcatttgagt taatgaggta   1860
aagagaaaat gagcaaaagc acaaacacgc taagtgccgg ccgtccgagc gcacgcagca   1920
gcaaggctgc aacgttggcc agcctggcag acacgccagc catgaagcgg gtcaactttc   1980
agttgccggc ggaggatcac accaagctga agatgtacgc ggtacgccaa ggcaagacca   2040
ttaccgagct gctatctgaa tacatcgcgc agctaccaga gtaaatgagc aaatgaataa   2100
atgagtagat gaattttagc ggctaaagga ggcggcatgg aaaatcaaga acaaccaggc   2160
accgacgccg tggaatgccc catgtgtgga ggaacgggcg gttggccagg cgtaagcggc   2220
tgggttgtct gccggccctg caatggcact ggaaccccca agcccgagga atcggcgtga   2280
cggtcgcaaa ccatccggcc cggtacaaat cggcgcggcg ctgggtgatg acctggtgga   2340
gaagttgaag gccgcgcagg ccgcccagcg gcaacgcatc gaggcagaag cacgccccgg   2400
tgaatcgtgg caagcggccg ctgatcgaat ccgcaaagaa tcccggcaac cgccggcagc   2460
cggtgcgccg tcgattagga agccgcccaa gggcgacgag caaccagatt ttttcgttcc   2520
gatgctctat gacgtgggca cccgcgatag tcgcagcatc atggacgtgg ccgttttccg   2580
tctgtcgaag cgtgaccgac gagctggcga ggtgatccgc tacgagcttc cagacgggca   2640
cgtagaggtt tccgcagggc cggccggcat ggccagtgtg tgggattacg acctggtact   2700
gatggcggtt tcccatctaa ccgaatccat gaaccgatac cgggaaggga agggagacaa   2760
gcccggccgc gtgttccgtc cacacgttgc ggacgtactc aagttctgcc ggcgagccga   2820
tggcggaaag cagaaagacg acctggtaga aacctgcatt cggttaaaca ccacgcacgt   2880
tgccatgcag cgtacgaaga aggccaagaa cggccgcctg gtgacggtat ccgagggtga   2940
agccttgatt agccgctaca agatcgtaaa gagcgaaacc gggcggccgg agtacatcga   3000
gatcgagcta gctgattgga tgtaccgcga gatcacagaa ggcaagaacc cggacgtgct   3060
gacggttcac cccgattact ttttgatcga tcccggcatc ggccgttttc tctaccgcct   3120
ggcacgccgc gccgcaggca aggcagaagc cagatggttg ttcaagacga tctacgaacg   3180
cagtggcagc gccggagagt tcaagaagtt ctgtttcacc gtgcgcaagc tgatcgggtc   3240
aaatgacctg ccggagtacg atttgaagga ggaggcgggg caggctggcc cgatcctagt   3300
catgcgctac cgcaacctga tcgagggcga agcatccgcc ggttcctaat gtacggagca   3360
gatgctaggg caaattgccc tagcagggga aaaaggtcga aaaggtctct ttcctgtgga   3420
tagcacgtac attgggaacc caaagccgta cattgggaac cggaacccgt acattgggaa   3480
cccaaagccg tacattggga accggtcaca catgtaagtg actgatataa aagagaaaaa   3540
aggcgatttt tccgcctaaa actctttaaa acttattaaa actcttaaaa cccgcctggc   3600
ctgtgcataa ctgtctggcc agcgcacagc cgaagagctg caaaaagcgc ctacccttcg   3660
gtcgctgcgc tccctacgcc ccgccgcttc gcgtcggcct atcgcggccg ctggccgctc   3720
aaaaatggct ggcctacggc caggcaatct accagggcgc ggacaagccg cgccgtcgcc   3780
actcgaccgc cggcgcccac atcaaggcac cctgcctcgc gcgtttcggt gatgacggtg   3840
aaaacctctg acacatgcag ctcccggaga cggtcacagc ttgtctgtaa gcggatgccg   3900
ggagcagaca agcccgtcag ggcgcgtcag cgggtgttgg cgggtgtcgg ggcgcagcca   3960
tgacccagtc acgtagcgat agcggagtgt atactggctt aactatgcgg catcagagca   4020
gattgtactg agagtgcacc atatgcggtg tgaaataccg cacagatgcg taaggagaaa   4080
```

-continued

```
ataccgcatc aggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcatagctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
acgttaaggg attttggtca tgcattctag gtactaaaac aattcatcca gtaaaatata   4980
atattttatt ttctcccaat caggcttgat ccccagtaag tcaaaaaata gctcgacata   5040
ctgttcttcc ccgatatcct ccctgatcga ccggacgcag aaggcaatgt cataccactt   5100
gtccgccctg ccgcttctcc caagatcaat aaagccactt actttgccat ctttcacaaa   5160
gatgttgctg tctcccaggt cgccgtggga aaagacaagt tcctcttcgg gcttttccgt   5220
ctttaaaaaa tcatacagct cgcgcggatc tttaaatgga gtgtcttctt cccagttttc   5280
gcaatccaca tcggccagat cgttattcag taagtaatcc aattcggcta agcggctgtc   5340
taagctattc gtatagggac aatccgatat gtcgatggag tgaaagagcc tgatgcactc   5400
cgcatacagc tcgataatct tttcagggct ttgttcatct tcatactctt ccgagcaaag   5460
gacgccatcg gcctcactca tgagcagatt gctccagcca tcatgccgtt caaagtgcag   5520
gacctttgga acaggcagct ttccttccag ccatagcatc atgtcctttt cccgttccac   5580
atcataggtg gtccctttat accggctgtc cgtcattttt aaatataggt tttcattttc   5640
tcccaccagc ttatatacct tagcaggaga cattccttcc gtatctttta cgcagcggta   5700
tttttcgatc agtttttca attccggtga tattctcatt ttagccattt attatttcct   5760
tcctcttttc tacagtattt aaagataccc caagaagcta attataacaa gacgaactcc   5820
aattcactgt tccttgcatt ctaaaacctt aaataccaga aaacagcttt ttcaaagttg   5880
ttttcaaagt tggcgtataa catagtatcg acggagccga ttttgaaacc gcggtgatca   5940
caggcagcaa cgctctgtca tcgttacaat caacatgcta ccctccgcga gatcatccgt   6000
gtttcaaacc cggcagctta gttgccgttc ttccgaatag catcggtaac atgagcaaag   6060
tctgccgcct tacaacggct ctcccgctga cgccgtcccg gactgatggg ctgcctgtat   6120
cgagtggtga ttttgtgccg agctgccggt cggggagctg ttggctggct ggtggcagga   6180
tatattgtgg tgtaaacaaa ttgacgctta gacaacttaa taacacattg cggacgtttt   6240
taatgtactg aattaacgcc gaattaattc gggggatctg gattttagta ctggattttg   6300
gttttaggaa ttagaaattt tattgataga agtattttac aaatacaaat acatactaag   6360
ggtttcttat atgctcaaca catgagcgaa accctatagg aaccctaatt cccttatctg   6420
```

```
ggaactactc acacattatt atggagaaac tcgagtcaaa tctcggtgac gggcaggacc   6480
ggacggggcg gtaccggcag gctgaagtcc agctgccaga aacccacgtc atgccagttc   6540
ccgtgcttga agccggccgc ccgcagcatg ccgcgggggg catatccgag cgcctcgtgc   6600
atgcgcacgc tcgggtcgtt gggcagcccg atgacagcga ccacgctctt gaagccctgt   6660
gcctccaggg acttcagcag gtgggtgtag agcgtggagc ccagtcccgt ccgctggtgg   6720
cggggggaga cgtacacggt cgactcggcc gtccagtcgt aggcgttgcg tgccttccag   6780
gggcccgcgt aggcgatgcc ggcgacctcg ccgtccacct cggcgacgag ccagggatag   6840
cgctcccgca gacggacgag gtcgtccgtc cactcctgcg gttcctgcgg ctcggtacgg   6900
aagttgaccg tgcttgtctc gatgtagtgg ttgacgatgg tgcagaccgc cggcatgtcc   6960
gcctcggtgg cacggcggat gtcggccggg cgtcgttctg ggctcatggt agactcgaga   7020
gagatagatt tgtagagaga gactggtgat ttcagcgtgt cctctccaaa tgaaatgaac   7080
ttccttatat agaggaaggt cttgcgaagg atagtgggat tgtgcgtcat cccttacgtc   7140
agtggagata tcacatcaat ccacttgctt tgaagacgtg gttggaacgt cttctttttc   7200
cacgatgctc ctcgtgggtg ggggtccatc tttgggacca ctgtcggcag aggcatcttg   7260
aacgatagcc tttcctttat cgcaatgatg gcatttgtag gtgccacctt cctttctac    7320
tgtccttttg atgaagtgac agatagctgg gcaatggaat ccgaggaggt ttcccgatat   7380
taccctttgt tgaaaagtct caatagccct ttggtcttct gagactgtat ctttgatatt   7440
cttggagtag acgagagtgt cgtgctccac catgttatca catcaatcca cttgctttga   7500
agacgtggtt ggaacgtctt ctttttccac gatgctcctc gtgggtgggg gtccatcttt   7560
gggaccactg tcggcagagg catcttgaac gatagccttt cctttatcgc aatgatggca   7620
tttgtaggtg ccaccttcct tttctactgt ccttttgatg aagtgacaga tagctgggca   7680
atggaatccg aggaggtttc ccgatattac cctttgttga aaagtctcaa tagccctttg   7740
gtcttctgag actgtatctt tgatattctt ggagtagacg agagtgtcgt gctccaccat   7800
gttggcaagc tgctctagcc aatacgcaaa ccgcctctcc ccgcgcgttg gccgattcat   7860
taatgcagct ggcacgacag gtttcccgac tggaaagcgg gcagtgagcg caacgcaatt   7920
aatgtgagtt agctcactca ttaggcaccc caggctttac actttatgct tccggctcgt   7980
atgttgtgtg gaattgtgag cggataacaa tttcacacag gaaacagcta tgaccatgat   8040
tacgaattcg agctccaccg cggtggcggc cgctctagaa ctagttaatt aaggaattat   8100
cgaaccactt tgtacaagaa agctgaacga gaaacgtaaa atgatataaa tatcaatata   8160
ttaaattaga ttttgcataa aaaacagact acataatact gtaaaacaca acatatccag   8220
tcactatggt cgacctgcag gttgtggttg gtgctttcct tacattctga gcctctttcc   8280
ttctaatcca ctcatctgca tcttcttgtg tccttactaa tacctcattg gttccaaatt   8340
ccctcccttt aagcaccagc tcgtttctgt tcttccacag cctcccaagt atccaaggga   8400
ctaaagcctc cacattcttc agatcaggat attcttgttt aagatgttga actctatgga   8460
ggtttgtatg aactgatgat ctaggaccgg ataagttccc ttcttcatag cgaacttatt   8520
caaagaatgt tttgtgtatc attcttgtta cattgttatt aatgaaaaaa tattattggt   8580
cattggactg aacacgagtg ttaaatatgg accaggcccc aaataagatc cattgatata   8640
tgaattaaat aacaagaata aatcgagtca ccaaaccact tgcctttttt aacgagactt   8700
gttcaccaac ttgatacaaa agtcattatc ctatgcaaat caataatcat acaaaaatat   8760
ccaataacac taaaaaaatt aaaagaaatg gataatttca caatatgtta tacgataaag   8820
```

-continued

```
aagttacttt tccaagaaat tcactgattt tataagccca cttgcattag ataaatggca   8880
aaaaaaaaca aaaaggaaaa gaaataaagc acgaagaatt ctagaaaata cgaaatacgc   8940
ttcaatgcag tggggaccca cggttcaatt attgccaatt tttcagctcc accgtatatt   9000
taaaaaataa aacgataatg ctaaaaaaat ataaatcgta acgatcgtta aatctcaacg   9060
gctggatctt atgacgaccg ttaaggaaat tgtggttgtc ggacgaagtc cagtaataaa   9120
cggcgtcaaa gtggttgcag ccggcacaca cgagtcgtgt ttatcaactc aaagcacaaa   9180
tacttttcct caacctaaaa ataaggcaat tagccaaaaa caactttgcg tgtaaacaac   9240
gctcaataca cgtgtcattt tattattagc tattgcttca ccgccttagc tttctcgtga   9300
cctagtcgtc ctcgtctttt cttcttcttc ttctataaaa caatacccaa agagctcttc   9360
ttcttcacaa ttcagatttc aatttctcaa aatcttaaaa actttctctc aattctctct   9420
accgtgatca aggtaaattt ctgtgttcct tattctctca aaatcttcga ttttgttttc   9480
gttcgatccc aatttcgtat atgttctttg gtttagattc tgttaatctt agatcgaaga   9540
cgattttctg ggtttgatcg ttagatatca tcttaattct cgattagggt ttcatagata   9600
tcatccgatt tgttcaaata atttgagttt tgtcgaataa ttactcttcg atttgtgatt   9660
tctatctaga tctggtgtta gtttctagtt tgtgcgatcg aatttgtcga ttaatctgag   9720
tttttctgat taacagatgc agatctttgc catggcgcgc tcctccaaga acgtcatcaa   9780
ggagttcatg cgcttcaagg tgcgcatgga gggcaccgtg aacggccacg agttcgagat   9840
cgagggcgag ggcgagggcc gcccctacga gggccacaac accgtgaagc tgaaggtgac   9900
caagggcggc cccctgccct tcgcctggga catcctgtcc ccccagttcc agtacggctc   9960
caaggtgtac gtgaagcacc ccgccgacat ccccgactac aagaagctgt ccttccccga  10020
gggcttcaag tgggagcgcg tgatgaactt cgaggacggc ggcgtggtga ccgtgaccca  10080
ggactcctcc ctgcaggacg gctgcttcat ctacaaggtg aagttcatcg gcgtgaactt  10140
cccctccgac ggccccgtaa tgcagaagaa gaccatgggc tgggaggcct ccaccgagcg  10200
cctgtacccc cgcgacggcg tgctgaaggg cgagatccac aaggccctga agctgaagga  10260
cggcggccac tacctggtgg agttcaagtc catctacatg gccaagaagc ccgtgcagct  10320
gcccggctac tactacgtgg actccaagct ggacatcacc tcccacaaac gaggactaca  10380
ccatcgtgga gcagtacgag cgcaccgagg gccgccacca cctgttcctg tagatggagt  10440
acacaaacag tgatgatgct acaaatgaaa aactcattga aaatggcagc tcttcatcat  10500
cttctcaacc cagaaagggt ggtttaagaa ccatgccctt tatcatagtg aatgagtgtc  10560
ttgagaaagt ggcaagttat ggaataatgc caaacatgat attatacttg agggatgatt  10620
ataacatgcc tattgctaag gctagttatg ttctttctac ttggtctgct atgtccaatg  10680
ttttgtccat ctttggtgct tttctctctg attcttactt gggtcgcttc aatgtcatca  10740
ctattggctc cttttctagc cttcttggtt taaccgtttt gtggttaact gccatgatcc  10800
cggtgctaaa acctacctgt gcatcactct ttgaaatctg taattctgct acttcatccc  10860
aacaagcagt tctgttcctt tccttaggat taatttcaat tggagctggt tgtgttagac  10920
cttgttccat agcctttgga gcaaagcaat tgactattaa gggaaattct ggtgatggga  10980
atggcaggat cttggatagt tactttaatt ggtattatac ctcaatttca gtttcaacca  11040
ttatcgcgtt gagtgtgatt gcttacattc aagaaaacct tggatggaaa attgggtttg  11100
gagtacctgc tgtgctaatg ctcgtatcgg tcatcagttt cattattggt tcaccgttat  11160
```

-continued atgtcaaagt gaagccaagt gaaagcttac tcactaattt tgcaagagta gttgtggtgg 11220
caaccaagaa cagaaaactt agtcttcctg atcacgactc tgatcgttac tgtcaaggtc 11280
atgattcaaa gctgaaggtt cctaccgata gccttaggtt tttgaacaaa gcttgcgtaa 11340
taagaaatcc tgagacagat cttaatcgag atgggtcaat ttcaaatccg tggaacctat 11400
gcacaataga acaggtggag tcactgaagt ctttgctcag agtcattcct atgtggtcaa 11460
cgggaatctt tatgatggcg actcagagtt cattttctac tcttcaagcc aaaactttga 11520
accgaacgtt attcggcaat ttcaattttc ctgcaggatc gttcaatctt atcttgatat 11580
tcaccttaac aatagtaatt cctttatatg accgtgtagg agtacctcta ctagctaaat 11640
acgcaggccg gcctagagga ttcagtttta aagtccgcat cgggatagga atgctgtttg 11700
caattgtagc taaagcagta gcagctattg ttgaaacggt gagacgaaat gcagcgattg 11760
aacaagggtt tgaggaccaa cctaatgctg aaattaacat gtcggcttta tggcttgctc 11820
cagagtttat tttgtttgga ttcgccgaag ctttcacacc agttggactg gttgagtttt 11880
tctactgttt tttccctaag agtatgtcta gttttgcaat ggctatgttc acattgggac 11940
tagcttgttc tgacgtagtt tcaggtgtgc ttgtgagcat tgtggacacg gtcactagta 12000
ttggagggaa tgagagctgg ttatcgacta acatcaatag gggacatttg aattactact 12060
acgggctact cactttctta ggcattctta actacttcta ttatcttgtt atttgttggg 12120
cttatggacc catacaggga gagaaacatg aagattcggc cagaaagaaa gacgataaat 12180
ttggttacag ggagttgcct acttcatagg ttcttaagat tgaatcctgt tgccggtctt 12240
gcgatgatta tcatataatt tctgttgaat tacgttaagc atgtaataat taacatgtaa 12300
tgcatgacgt tatttatgag atgggttttt atgattagag tcccgcaatt atacatttaa 12360
tacgcgatag aaaacaaaat atagcgcgca aactaggata aattatcgcg cgcggtgtca 12420
tctatgttac tagatcgggc ctaactcaaa atccacacat tatacgagcc ggaagcataa 12480
agtgtaaagc ctggggtgcc taatgcggcc gccatagtga ctggatatgt tgtgttttac 12540
agtattatgt agtctgtttt ttatgcaaaa tctaatttaa tatattgata tttatatcat 12600
tttacgtttc tcgttcagct tttttgtaca aacttgtttg atagcttggc gcgcctcgag 12660
ggggggcccg gtacccgggg atcctctaga gtcgacctgc aggcatgcgg cactggccgt 12720
cgttttacaa cgtcgtgact gggaaaaccc tggcgttacc caacttaatc gccttgcagc 12780
acatccccct ttcgccagct ggcgtaatag cgaagaggcc cgcaccgatc gcccttccca 12840
acagttgcgc agcctgaatg gcgaatgcta gagcagcttg agcttggatc agattgtcgt 12900
ttcccgcctt cagtttaaac tatcagtgtt tgacaggata tattggcggg taaacctaag 12960
agaaaagagc gtttattaga ataacggata tttaaaaggg cgtgaaaagg tttatccgtt 13020
cgtccatttg tatgtg 13036

<210> SEQ ID NO 28
<211> LENGTH: 13036
<212> TYPE: DNA
<213> ORGANISM: Artificial Sequence
<220> FEATURE:
<223> OTHER INFORMATION: Synthesized

<400> SEQUENCE: 28
catgccaacc acagggttcc cctcgggatc aaagtacttt gatccaaccc ctccgctgct 60
atagtgcagt cggcttctga cgttcagtgc agccgtcttc tgaaaacgac atgtcgcaca 120
agtcctaagt tacgcgacag gctgccgccc tgccctttc ctggcgtttt cttgtcgcgt 180

```
gttttagtcg cataaagtag aatacttgcg actagaaccg gagacattac gccatgaaca    240
agagcgccgc cgctggcctg ctgggctatg cccgcgtcag caccgacgac caggacttga    300
ccaaccaacg ggccgaactg cacgcggccg gctgcaccaa gctgttttcc gagaagatca    360
ccggcaccag gcgcgaccgc ccggagctgg ccaggatgct tgaccaccta cgccctggcg    420
acgttgtgac agtgaccagg ctagaccgcc tggcccgcag cacccgcgac ctactggaca    480
ttgccgagcg catccaggag gccggcgcgg gcctgcgtag cctggcagag ccgtgggccg    540
acaccaccac gccggccggc cgcatggtgt tgaccgtgtt cgccggcatt gccgagttcg    600
agcgttccct aatcatcgac cgcacccgga gcgggcgcga ggccgccaag gcccgaggcg    660
tgaagtttgg cccccgccct accctcaccc cggcacagat cgcgcacgcc cgcgagctga    720
tcgaccagga aggccgcacc gtgaaagagg cggctgcact gcttggcgtg catcgctcga    780
ccctgtaccg cgcacttgag cgcagcgagg aagtgacgcc caccgaggcc aggcggcgcg    840
gtgccttccg tgaggacgca ttgaccgagg ccgacgccct ggcggccgcc gagaatgaac    900
gccaagagga acaagcatga aaccgcacca ggacggccag gacgaaccgt ttttcattac    960
cgaagagatc gaggcggaga tgatcgcggc cgggtacgtg ttcgagccgc ccgcgcacgt   1020
ctcaaccgtg cggctgcatg aaatcctggc cggtttgtct gatgccaagc tggcggcctg   1080
gccggccagc ttggccgctg aagaaaccga gcgccgccgt ctaaaaaggt gatgtgtatt   1140
tgagtaaaac agcttgcgtc atgcggtcgc tgcgtatatg atgcgatgag taaataaaca   1200
aatacgcaag gggaacgcat gaaggttatc gctgtactta accagaaagg cgggtcaggc   1260
aagacgacca tcgcaaccca tctagcccgc gccctgcaac tcgccggggc cgatgttctg   1320
ttagtcgatt ccgatcccca gggcagtgcc cgcgattggg cggccgtgcg ggaagatcaa   1380
ccgctaaccg ttgtcggcat cgaccgcccg acgattgacc gcgacgtgaa ggccatcggc   1440
cggcgcgact tcgtagtgat cgacggagcg ccccaggcgg cggacttggc tgtgtccgcg   1500
atcaaggcag ccgacttcgt gctgattccg gtgcagccaa gcccttacga catatgggcc   1560
accgccgacc tggtggagct ggttaagcag cgcattgagg tcacggatgg aaggctacaa   1620
gcggcctttg tcgtgtcgcg ggcgatcaaa ggcacgcgca tcggcggtga ggttgccgag   1680
gcgctggccg ggtacgagct gcccattctt gagtcccgta tcacgcagcg cgtgagctac   1740
ccaggcactg ccgccgccgg cacaaccgtt cttgaatcag aacccgaggg cgacgctgcc   1800
cgcgaggtcc aggcgctggc cgctgaaatt aaatcaaaac tcatttgagt taatgaggta   1860
aagagaaaat gagcaaaagc acaaacacgc taagtgccgg ccgtccgagc gcacgcagca   1920
gcaaggctgc aacgttggcc agcctggcag acacgccagc catgaagcgg gtcaactttc   1980
agttgccggc ggaggatcac accaagctga agatgtacgc ggtacgccaa ggcaagacca   2040
ttaccgagct gctatctgaa tacatcgcgc agctaccaga gtaaatgagc aaatgaataa   2100
atgagtagat gaattttagc ggctaaagga ggcggcatgg aaaatcaaga acaaccaggc   2160
accgacgccg tggaatgccc catgtgtgga ggaacgggcg gttggccagg cgtaagcggc   2220
tgggttgtct gccggccctg caatggcact ggaaccccca agcccgagga atcggcgtga   2280
cggtcgcaaa ccatccggcc cggtacaaat cggcgcggcg ctgggtgatg acctggtgga   2340
gaagttgaag gccgcgcagg ccgcccagcg gcaacgcatc gaggcagaag cacgccccgg   2400
tgaatcgtgg caagcggccg ctgatcgaat ccgcaaagaa tcccggcaac cgccggcagc   2460
cggtgcgccg tcgattagga agccgcccaa gggcgacgag caaccagatt ttttcgttcc   2520
```

-continued

```
gatgctctat gacgtgggca cccgcgatag tcgcagcatc atggacgtgg ccgttttccg   2580
tctgtcgaag cgtgaccgac gagctggcga ggtgatccgc tacgagcttc cagacgggca   2640
cgtagaggtt tccgcagggc cggccggcat ggccagtgtg tgggattacg acctggtact   2700
gatggcggtt tcccatctaa ccgaatccat gaaccgatac cgggaaggga agggagacaa   2760
gcccggccgc gtgttccgtc cacacgttgc ggacgtactc aagttctgcc ggcgagccga   2820
tggcggaaag cagaaagacg acctggtaga aacctgcatt cggttaaaca ccacgcacgt   2880
tgccatgcag cgtacgaaga aggccaagaa cggccgcctg gtgacggtat ccgagggtga   2940
agccttgatt agccgctaca agatcgtaaa gagcgaaacc gggcggccgg agtacatcga   3000
gatcgagcta gctgattgga tgtaccgcga gatcacagaa ggcaagaacc cggacgtgct   3060
gacggttcac cccgattact ttttgatcga tcccggcatc ggccgttttc tctaccgcct   3120
ggcacgccgc gccgcaggca aggcagaagc cagatggttg ttcaagacga tctacgaacg   3180
cagtggcagc gccggagagt tcaagaagtt ctgtttcacc gtgcgcaagc tgatcgggtc   3240
aaatgacctg ccggagtacg atttgaagga ggaggcgggg caggctggcc cgatcctagt   3300
catgcgctac cgcaacctga tcgagggcga agcatccgcc ggttcctaat gtacggagca   3360
gatgctaggg caaattgccc tagcagggga aaaaggtcga aaaggtctct ttcctgtgga   3420
tagcacgtac attgggaacc caaagccgta cattgggaac cggaacccgt acattgggaa   3480
cccaaagccg tacattggga accggtcaca catgtaagtg actgatataa aagagaaaaa   3540
aggcgatttt tccgcctaaa actctttaaa acttattaaa actcttaaaa cccgcctggc   3600
ctgtgcataa ctgtctggcc agcgcacagc cgaagagctg caaaaagcgc ctacccttcg   3660
gtcgctgcgc tccctacgcc ccgccgcttc gcgtcggcct atcgcggccg ctggccgctc   3720
aaaaatggct ggcctacggc caggcaatct accagggcgc ggacaagccg cgccgtcgcc   3780
actcgaccgc cggcgcccac atcaaggcac cctgcctcgc gcgtttcggt gatgacggtg   3840
aaaacctctg acacatgcag ctcccggaga cggtcacagc ttgtctgtaa gcggatgccg   3900
ggagcagaca agcccgtcag ggcgcgtcag cgggtgttgg cgggtgtcgg ggcgcagcca   3960
tgacccagtc acgtagcgat agcggagtgt atactggctt aactatgcgg catcagagca   4020
gattgtactg agagtgcacc atatgcggtg tgaaataccg cacagatgcg taaggagaaa   4080
ataccgcatc aggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcatagctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
```

-continued

```
acgttaaggg attttggtca tgcattctag gtactaaaac aattcatcca gtaaaatata   4980
atattttatt ttctcccaat caggcttgat ccccagtaag tcaaaaaata gctcgacata   5040
ctgttcttcc ccgatatcct ccctgatcga ccggacgcag aaggcaatgt cataccactt   5100
gtccgccctg ccgcttctcc caagatcaat aaagccactt actttgccat ctttcacaaa   5160
gatgttgctg tctcccaggt cgccgtggga aaagacaagt tcctcttcgg gcttttccgt   5220
ctttaaaaaa tcatacagct cgcgcggatc tttaaatgga gtgtcttctt cccagttttc   5280
gcaatccaca tcggccagat cgttattcag taagtaatcc aattcggcta agcggctgtc   5340
taagctattc gtatagggac aatccgatat gtcgatggag tgaaagagcc tgatgcactc   5400
cgcatacagc tcgataatct tttcagggct ttgttcatct tcatactctt ccgagcaaag   5460
gacgccatcg gcctcactca tgagcagatt gctccagcca tcatgccgtt caaagtgcag   5520
gacctttgga acaggcagct ttccttccag ccatagcatc atgtcctttt cccgttccac   5580
atcataggtg gtccctttat accggctgtc cgtcattttt aaatataggt tttcattttc   5640
tcccaccagc ttatatacct tagcaggaga cattccttcc gtatctttta cgcagcggta   5700
tttttcgatc agtttttca attccggtga tattctcatt ttagccattt attatttcct   5760
tcctcttttc tacagtattt aaagataccc caagaagcta attataacaa gacgaactcc   5820
aattcactgt tccttgcatt ctaaaacctt aaataccaga aaacagcttt ttcaaagttg   5880
ttttcaaagt tggcgtataa catagtatcg acggagccga ttttgaaacc gcggtgatca   5940
caggcagcaa cgctctgtca tcgttacaat caacatgcta ccctccgcga gatcatccgt   6000
gtttcaaacc cggcagctta gttgccgttc ttccgaatag catcggtaac atgagcaaag   6060
tctgccgcct tacaacggct ctcccgctga cgccgtcccg gactgatggg ctgcctgtat   6120
cgagtggtga ttttgtgccg agctgccggt cggggagctg ttggctggct ggtggcagga   6180
tatattgtgg tgtaaacaaa ttgacgctta gacaacttaa taacacattg cggacgtttt   6240
taatgtactg aattaacgcc gaattaattc gggggatctg gattttagta ctggattttg   6300
gttttaggaa ttagaaattt tattgataga agtattttac aaatacaaat acatactaag   6360
ggtttcttat atgctcaaca catgagcgaa accctatagg aaccctaatt cccttatctg   6420
ggaactactc acacattatt atggagaaac tcgagtcaaa tctcggtgac gggcaggacc   6480
ggacggggcg gtaccggcag gctgaagtcc agctgccaga aacccacgtc atgccagttc   6540
ccgtgcttga agccggccgc ccgcagcatg ccgcgggggg catatccgag cgcctcgtgc   6600
atgcgcacgc tcgggtcgtt gggcagcccg atgacagcga ccacgctctt gaagccctgt   6660
gcctccaggg acttcagcag gtgggtgtag agcgtggagc ccagtcccgt ccgctggtgg   6720
cggggggaga cgtacacggt cgactcggcc gtccagtcgt aggcgttgcg tgccttccag   6780
gggcccgcgt aggcgatgcc ggcgacctcg ccgtccacct cggcgacgag ccagggatag   6840
cgctcccgca gacggacgag gtcgtccgtc cactcctgcg gttcctgcgg ctcggtacgg   6900
aagttgaccg tgcttgtctc gatgtagtgg ttgacgatgg tgcagaccgc cggcatgtcc   6960
gcctcggtgg cacggcggat gtcggccggg cgtcgttctg ggctcatggt agactcgaga   7020
gagatagatt tgtagagaga gactggtgat ttcagcgtgt cctctccaaa tgaaatgaac   7080
ttccttatat agaggaaggt cttgcgaagg atagtgggat tgtgcgtcat cccttacgtc   7140
agtggagata tcacatcaat ccacttgctt tgaagacgtg gttggaacgt cttcttttc    7200
cacgatgctc ctcgtgggtg ggggtccatc tttgggacca ctgtcggcag aggcatcttg   7260
```

-continued

```
aacgatagcc tttcctttat cgcaatgatg gcatttgtag gtgccacctt ccttttctac   7320
tgtccttttg atgaagtgac agatagctgg gcaatggaat ccgaggaggt ttcccgatat   7380
taccctttgt tgaaaagtct caatagccct ttggtcttct gagactgtat ctttgatatt   7440
cttggagtag acgagagtgt cgtgctccac catgttatca catcaatcca cttgctttga   7500
agacgtggtt ggaacgtctt ctttttccac gatgctcctc gtgggtgggg gtccatcttt   7560
gggaccactg tcggcagagg catcttgaac gatagccttt cctttatcgc aatgatggca   7620
tttgtaggtg ccaccttcct tttctactgt ccttttgatg aagtgacaga tagctgggca   7680
atggaatccg aggaggtttc ccgatattac cctttgttga aaagtctcaa tagccctttg   7740
gtcttctgag actgtatctt tgatattctt ggagtagacg agagtgtcgt gctccaccat   7800
gttggcaagc tgctctagcc aatacgcaaa ccgcctctcc ccgcgcgttg gccgattcat   7860
taatgcagct ggcacgacag gtttcccgac tggaaagcgg gcagtgagcg caacgcaatt   7920
aatgtgagtt agctcactca ttaggcaccc caggctttac actttatgct tccggctcgt   7980
atgttgtgtg gaattgtgag cggataacaa tttcacacag gaaacagcta tgaccatgat   8040
tacgaattcg agctccaccg cggtggcggc cgctctagaa ctagttaatt aaggaattat   8100
cgaaccactt tgtacaagaa agctgaacga gaaacgtaaa atgatataaa tatcaatata   8160
ttaaattaga ttttgcataa aaaacagact acataatact gtaaaacaca acatatccag   8220
tcactatggt cgacctgcag gttgtggttg gtgctttcct tacattctga gcctctttcc   8280
ttctaatcca ctcatctgca tcttcttgtg tccttactaa tacctcattg gttccaaatt   8340
ccctcccttt aagcaccagc tcgtttctgt tcttccacag cctcccaagt atccaaggga   8400
ctaaagcctc cacattcttc agatcaggat attcttgttt aagatgttga actctatgga   8460
ggtttgtatg aactgatgat ctaggaccgg ataagttccc ttcttcatag cgaacttatt   8520
caaagaatgt tttgtgtatc attcttgtta cattgttatt aatgaaaaaa tattattggt   8580
cattggactg aacacgagtg ttaaatatgg accaggcccc aaataagatc cattgatata   8640
tgaattaaat aacaagaata aatcgagtca ccaaaccact tgcctttttt aacgagactt   8700
gttcaccaac ttgatacaaa agtcattatc ctatgcaaat caataatcat acaaaaatat   8760
ccaataacac taaaaaaatt aaaagaaatg gataatttca caatatgtta tacgataaag   8820
aagttacttt tccaagaaat tcactgattt tataagccca cttgcattag ataaatggca   8880
aaaaaaaaca aaaaggaaaa gaaataaagc acgaagaatt ctagaaaata cgaaatacgc   8940
ttcaatgcag tggggaccca cggttcaatt attgccaatt tttcagctcc accgtatatt   9000
taaaaaataa aacgataatg ctaaaaaaat ataaatcgta acgatcgtta aatctcaacg   9060
gctggatctt atgacgaccg ttaaggaaat tgtggttgtc ggacgaagtc cagtaataaa   9120
cggcgtcaaa gtggttgcag ccggcacaca cgagtcgtgt ttatcaactc aaagcacaaa   9180
tacttttcct caacctaaaa ataaggcaat tagccaaaaa caactttgcg tgtaaacaac   9240
gctcaataca cgtgtcattt tattattagc tattgcttca ccgccttagc tttctcgtga   9300
cctagtcgtc ctcgtctttt cttcttcttc ttctataaaa caatacccaa agagctcttc   9360
ttcttcacaa ttcagatttc aatttctcaa aatcttaaaa actttctctc aattctctct   9420
accgtgatca aggtaaattt ctgtgttcct tattctctca aaatcttcga ttttgttttc   9480
gttcgatccc aatttcgtat atgttctttg gtttagattc tgttaatctt agatcgaaga   9540
cgattttctg ggtttgatcg ttagatatca tcttaattct cgattagggt ttcatagata   9600
tcatccgatt tgttcaaata atttgagttt tgtcgaataa ttactcttcg atttgtgatt   9660
```

```
tctatctaga tctggtgtta gtttctagtt tgtgcgatcg aatttgtcga ttaatctgag   9720
tttttctgat taacagatgc agatctttgc catggcgcgc tcctccaaga acgtcatcaa   9780
ggagttcatg cgcttcaagg tgcgcatgga gggcaccgtg aacggccacg agttcgagat   9840
cgagggcgag ggcgagggcc gcccctacga gggccacaac accgtgaagc tgaaggtgac   9900
caagggcggc cccctgccct tcgcctggga catcctgtcc ccccagttcc agtacggctc   9960
caaggtgtac gtgaagcacc ccgccgacat ccccgactac aagaagctgt ccttccccga  10020
gggcttcaag tgggagcgcg tgatgaactt cgaggacggc ggcgtggtga ccgtgaccca  10080
ggactcctcc ctgcaggacg gctgcttcat ctacaaggtg aagttcatcg gcgtgaactt  10140
cccctccgac ggccccgtaa tgcagaagaa gaccatgggc tgggaggcct ccaccgagcg  10200
cctgtacccc cgcgacggcg tgctgaaggg cgagatccac aaggccctga agctgaagga  10260
cggcggccac tacctggtgg agttcaagtc catctacatg gccaagaagc ccgtgcagct  10320
gcccggctac tactacgtgg actccaagct ggacatcacc tcccacaaac gaggactaca  10380
ccatcgtgga gcagtacgag cgcaccgagg gccgccacca cctgttcctg tagatggagt  10440
acacaaacag tgatgatgct acaaatgaaa aactcattga aaatggcagc tcttcatcat  10500
cttctcaacc cagaaagggt ggtttaagaa ccatgccctt tatcatagtg aatgagtgtc  10560
ttgagaaagt ggcaagttat ggaataatgc caaacatgat attatacttg agggatgatt  10620
ataacatgcc tattgctaag gctagttatg ttctttctac ttggtctgct atgtccaatg  10680
ttttgtccat ctttggtgct tttctctctg attcttactt gggtcgcttc aatgtcatca  10740
ctattggctc cttttctagc cttcttggtt taaccgtttt gtggttaact gccatgatcc  10800
cggtgctaaa acctacctgt gcatcactct ttgaaatctg taattctgct acttcatccc  10860
aacaagcagt tctgttcctt tccttaggat taatttcaat tggagctggt tgtgttagac  10920
cttgttccat agcctttgga gcagagcaat tgactattaa gggaaattct ggtgatggga  10980
atggcaggat cttggatagt tactttaatt ggtattatac ctcaatttca gtttcaacca  11040
ttatcgcgtt gagtgtgatt gcttacattc aagaaaacct tggatggaaa attgggtttg  11100
gagtacctgc tgtgctaatg ctcgtatcgg tcatcagttt cattattggt tcaccgttat  11160
atgtcaaagt gaagccaagt gaaagcttac tcactaattt tgcaagagta gttgtggtgg  11220
caaccaagaa cagaaaactt agtcttcctg atcacgactc tgatcgttac tgtcaaggtc  11280
atgattcaaa gctgaaggtt cctaccgata gccttaggtt tttgaacaaa gcttgcgtaa  11340
taagaaatcc tgagacagat cttaatcgag atgggtcaat ttcaaatccg tggaacctat  11400
gcacaataga acaggtggag tcactgaagt ctttgctcag agtcattcct atgtgatcaa  11460
cgggaatctt tatgatggcg actcagagtt catttctac tcttcaagcc aaaactttga  11520
accgaacgtt attcggcaat ttcaattttc ctgcaggatc gttcaatctt atcttgatat  11580
tcaccttaac aatagtaatt cctttatatg accgtgtagg agtacctcta ctagctaaat  11640
acgcaggccg gcctagagga ttcagtttta aagtccgcat cgggatagga atgctgtttg  11700
caattgtagc taaagcagta gcagctattg ttgaaacggt gagacgaaat gcagcgattg  11760
aacaagggtt tgaggaccaa cctaatgctg aaattaacat gtcggcttta tggcttgctc  11820
cagagtttat tttgtttgga ttcgccgaag ctttcacacc agttggactg gttgagtttt  11880
tctactgttt tttccctaag agtatgtcta gttttgcaat ggctatgttc acattgggac  11940
tagcttgttc tgacgtagtt tcaggtgtgc ttgtgagcat tgtggacacg gtcactagta  12000
```

-continued

```
ttggagggaa tgagagctgg ttatcgacta acatcaatag gggacatttg aattactact  12060
acgggctact cactttctta ggcattctta actacttcta ttatcttgtt atttgttggg  12120
cttatggacc catacaggga gagaaacatg aagattcggc cagaaagaaa gacgataaat  12180
ttggttacag ggagttgcct acttcatagg ttcttaagat tgaatcctgt tgccggtctt  12240
gcgatgatta tcatataatt tctgttgaat tacgttaagc atgtaataat taacatgtaa  12300
tgcatgacgt tatttatgag atgggttttt atgattagag tcccgcaatt atacatttaa  12360
tacgcgatag aaaacaaaat atagcgcgca aactaggata aattatcgcg cgcggtgtca  12420
tctatgttac tagatcgggc ctaactcaaa atccacacat tatacgagcc ggaagcataa  12480
agtgtaaagc ctggggtgcc taatgcggcc gccatagtga ctggatatgt tgtgttttac  12540
agtattatgt agtctgtttt ttatgcaaaa tctaatttaa tatattgata tttatatcat  12600
tttacgtttc tcgttcagct tttttgtaca aacttgtttg atagcttggc gcgcctcgag  12660
ggggggcccg gtacccgggg atcctctaga gtcgacctgc aggcatgcgg cactggccgt  12720
cgttttacaa cgtcgtgact gggaaaaccc tggcgttacc caacttaatc gccttgcagc  12780
acatccccct ttcgccagct ggcgtaatag cgaagaggcc cgcaccgatc gcccttccca  12840
acagttgcgc agcctgaatg gcgaatgcta gagcagcttg agcttggatc agattgtcgt  12900
ttcccgcctt cagtttaaac tatcagtgtt tgacaggata tattggcggg taaacctaag  12960
agaaaagagc gtttattaga ataacggata tttaaaaggg cgtgaaaagg tttatccgtt  13020
cgtccatttg tatgtg                                                  13036
```

<210> SEQ ID NO 29
<211> LENGTH: 1511
<212> TYPE: DNA
<213> ORGANISM: Artificial Sequence
<220> FEATURE:
<223> OTHER INFORMATION: Synthesized

<400> SEQUENCE: 29

```
gttgtggttg gtgctttcct tacattctga gcctctttcc ttctaatcca ctcatctgca     60
tcttcttgtg tccttactaa tacctcattg gttccaaatt ccctcccttt aagcaccagc    120
tcgtttctgt tcttccacag cctcccaagt atccaaggga ctaaagcctc cacattcttc    180
agatcaggat attcttgttt aagatgttga actctatgga ggtttgtatg aactgatgat    240
ctaggaccgg ataagttccc ttcttcatag cgaacttatt caaagaatgt tttgtgtatc    300
attcttgtta cattgttatt aatgaaaaaa tattattggt cattggactg aacacgagtg    360
ttaaatatgg accaggcccc aaataagatc cattgatata tgaattaaat aacaagaata    420
aatcgagtca ccaaaccact tgcctttttt aacgagactt gttcaccaac ttgatacaaa    480
agtcattatc ctatgcaaat caataatcat acaaaaatat ccaataacac taaaaaaatt    540
aaaagaaatg gataatttca caatatgtta tacgataaag aagttacttt tccaagaaat    600
tcactgattt tataagccca cttgcattag ataaatggca aaaaaaaaca aaaaggaaaa    660
gaaataaagc acgaagaatt ctagaaaata cgaaatacgc ttcaatgcag tggggaccca    720
cggttcaatt attgccaatt tttcagctcc accgtatatt taaaaaataa aacgataatg    780
ctaaaaaaat ataaatcgta acgatcgtta aatctcaacg gctggatctt atgacgaccg    840
ttaaggaaat tgtggttgtc ggacgaagtc cagtaataaa cggcgtcaaa gtggttgcag    900
ccggcacaca cgagtcgtgt ttatcaactc aaagcacaaa tacttttcct caacctaaaa    960
ataaggcaat tagccaaaaa caactttgcg tgtaaacaac gctcaataca cgtgtcattt   1020
```

-continued

```
tattattagc tattgcttca ccgccttagc tttctcgtga cctagtcgtc ctcgtctttt   1080

cttcttcttc ttctataaaa caatacccaa agagctcttc ttcttcacaa ttcagatttc   1140

aatttctcaa aatcttaaaa actttctctc aattctctct accgtgatca aggtaaattt   1200

ctgtgttcct tattctctca aaatcttcga ttttgttttc gttcgatccc aatttcgtat   1260

atgttctttg gtttagattc tgttaatctt agatcgaaga cgattttctg ggtttgatcg   1320

ttagatatca tcttaattct cgattagggt ttcatagata tcatccgatt tgttcaaata   1380

atttgagttt tgtcgaataa ttactcttcg atttgtgatt tctatctaga tctggtgtta   1440

gtttctagtt tgtgcgatcg aatttgtcga ttaatctgag tttttctgat taacagatgc   1500

agatctttgc c                                                        1511
```